(12) United States Patent
Jain et al.

(10) Patent No.: US 11,151,462 B2
(45) Date of Patent: Oct. 19, 2021

(54) SYSTEMS AND METHODS FOR USING MACHINE LEARNING TO IMPROVE PROCESSES FOR ACHIEVING READINESS

(71) Applicant: Vignet Incorporated, Fairfax, VA (US)

(72) Inventors: Praduman Jain, Fairfax, VA (US); Dave Klein, Oakton, VA (US); Josh Schilling, Salem, OR (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 16/781,793

(22) Filed: Feb. 4, 2020

(65) Prior Publication Data
US 2021/0241139 A1 Aug. 5, 2021

(51) Int. Cl.
*G06N 5/04* (2006.01)
*G06N 20/00* (2019.01)
*A63B 24/00* (2006.01)

(52) U.S. Cl.
CPC ............. *G06N 5/04* (2013.01); *G06N 20/00* (2019.01); *A63B 24/00* (2013.01)

(58) Field of Classification Search
None
See application file for complete search history.

(56) References Cited

U.S. PATENT DOCUMENTS

| | | | |
|---|---|---|---|
| 5,625,706 A | 4/1997 | Lee et al. | |
| 6,419,629 B1 | 7/2002 | Balkin et al. | |
| 6,527,715 B2 | 3/2003 | Balkin et al. | |
| 6,807,535 B2 | 10/2004 | Goodkovsky | |
| 6,973,622 B1 | 12/2005 | Rappaport et al. | |
| 7,717,827 B2 | 5/2010 | Kurunmaki et al. | |
| 7,766,827 B2 | 8/2010 | Balkin et al. | |
| 8,010,337 B2 | 8/2011 | Narayanan et al. | |
| 8,052,580 B2 | 11/2011 | Saalasti et al. | |
| 8,398,546 B2 | 3/2013 | Pacione et al. | |
| 8,533,001 B2 | 9/2013 | Skiba | |
| 8,583,453 B2 | 11/2013 | Plummer et al. | |

(Continued)

OTHER PUBLICATIONS

Gondek, D.C. et al., "A framework for merging and ranking answers in DeepQA," IBM J. Res. & Dev, vol. 56, No. 3/4 (May/Jul. 2012) 12 pp. (Year: 2012).*

(Continued)

*Primary Examiner* — Brian M Smith
(74) *Attorney, Agent, or Firm* — Fish & Richardson P.C.

(57) ABSTRACT

Methods, systems, and apparatus, including computer programs encoded on a computer storage medium, for using machine learning to improve processes for achieving readiness. In some implementations, a database is accessed to obtain status data that indicates activities or attributes of a subject. One or more readiness scores indicating a level of capability of the subject to satisfy one or more readiness criteria are generated. Data is accessed indicating multiple candidate actions for improving capability of the subject to satisfy one or more readiness criteria. A subset of the candidate actions for the subject are selected based on the one or more readiness scores generated using the one or more models. Output is provided to cause one or more of the actions in the selected subset to be performed or cause an indication one or more of the actions in the selected subset to be presented on a user interface.

26 Claims, 22 Drawing Sheets

(56) References Cited

U.S. PATENT DOCUMENTS

| | | | |
|---|---|---|---|
| 8,684,922 B2 | 4/2014 | Tran | |
| 8,707,392 B2 | 4/2014 | Birtwhistle et al. | |
| 8,892,219 B2 | 11/2014 | Pryor | |
| 9,084,937 B2 | 7/2015 | Gadher et al. | |
| 9,286,442 B2 | 3/2016 | Csoma et al. | |
| 9,390,501 B2 | 7/2016 | Marty et al. | |
| 9,413,619 B2 | 8/2016 | Akolkar et al. | |
| 9,489,630 B2 | 11/2016 | Achin et al. | |
| 9,514,655 B1 | 12/2016 | Nusbaum et al. | |
| 10,231,622 B2 | 3/2019 | Soyao et al. | |
| 10,290,221 B2 | 5/2019 | Stacy et al. | |
| 10,304,000 B2 | 5/2019 | Birnbaum et al. | |
| 10,318,671 B2 | 6/2019 | Schmedlen | |
| 10,318,877 B2 | 6/2019 | Byrne et al. | |
| 10,380,147 B1 | 8/2019 | Omland | |
| 10,452,816 B2 | 10/2019 | Kidd et al. | |
| 10,546,339 B2 | 1/2020 | Jiao et al. | |
| 10,580,531 B2 | 3/2020 | Jiao et al. | |
| 10,636,525 B2 | 4/2020 | Jiao et al. | |
| 10,650,474 B2 | 5/2020 | Jiao et al. | |
| 10,672,519 B2 | 6/2020 | Jiao et al. | |
| 2002/0107784 A1 | 10/2002 | Hancock et al. | |
| 2004/0210661 A1 | 10/2004 | Thompson | |
| 2004/0225200 A1 | 11/2004 | Edmundson et al. | |
| 2005/0216426 A1 | 9/2005 | Weston et al. | |
| 2005/0273350 A1 | 12/2005 | Scarborough et al. | |
| 2006/0032315 A1 | 2/2006 | Saalastic et al. | |
| 2006/0074823 A1 | 4/2006 | Heumann et al. | |
| 2006/0074828 A1 | 4/2006 | Heumann et al. | |
| 2006/0282306 A1 | 12/2006 | Thissen-Roe | |
| 2008/0004835 A1 | 1/2008 | Srinivasan et al. | |
| 2008/0261776 A1* | 10/2008 | Skiba | A63B 24/0062 482/8 |
| 2008/0294459 A1 | 11/2008 | Angell et al. | |
| 2009/0187402 A1 | 7/2009 | Scholl | |
| 2010/0303225 A1 | 12/2010 | Shashkov et al. | |
| 2011/0119212 A1 | 5/2011 | De Bruin et al. | |
| 2011/0281248 A1 | 11/2011 | Feenstra et al. | |
| 2013/0096892 A1 | 4/2013 | Essa et al. | |
| 2013/0262140 A1 | 10/2013 | Friedlander et al. | |
| 2014/0221790 A1 | 8/2014 | Pacione et al. | |
| 2014/0278474 A1 | 9/2014 | McClure et al. | |
| 2014/0342328 A1 | 11/2014 | Pacione et al. | |
| 2015/0050637 A1 | 2/2015 | James-Hatter et al. | |
| 2015/0193588 A1 | 7/2015 | Nemoto et al. | |
| 2015/0242707 A1 | 8/2015 | Wilf et al. | |
| 2015/0294574 A1 | 10/2015 | Pacione et al. | |
| 2015/0339946 A1 | 11/2015 | Pacione et al. | |
| 2016/0086505 A1 | 3/2016 | Hanlon | |
| 2016/0098541 A1 | 4/2016 | Haskell et al. | |
| 2016/0140322 A1 | 5/2016 | Menon et al. | |
| 2016/0196758 A1 | 7/2016 | Causevic et al. | |
| 2017/0061817 A1 | 3/2017 | May | |
| 2017/0120107 A1 | 5/2017 | Wisbey | |
| 2017/0235912 A1 | 8/2017 | Moturu et al. | |
| 2017/0266501 A1* | 9/2017 | Sanders | A43B 5/00 |
| 2018/0025125 A1 | 1/2018 | Crane et al. | |
| 2018/0042540 A1 | 2/2018 | Kinnuhen | |
| 2018/0056130 A1 | 3/2018 | Bitran et al. | |
| 2018/0068083 A1 | 3/2018 | Cohen et al. | |
| 2018/0147493 A1 | 5/2018 | Cohen et al. | |
| 2018/0247178 A1 | 8/2018 | Ide et al. | |
| 2018/0249944 A1 | 9/2018 | Poutiatine et al. | |
| 2019/0122266 A1 | 4/2019 | Ramer et al. | |
| 2019/0140892 A1 | 5/2019 | Jain et al. | |
| 2019/0244540 A1 | 8/2019 | Errante et al. | |
| 2020/0008725 A1* | 1/2020 | Bach | A61B 5/369 |
| 2020/0058382 A1 | 2/2020 | Birnbaum et al. | |
| 2020/0118678 A1* | 4/2020 | Hardee | A63B 24/0075 |
| 2020/0129808 A1* | 4/2020 | Fomin | A63B 24/0006 |

OTHER PUBLICATIONS

American Cancer Society, "Living as a Laryngeal or Hypopharyngeal Cancer Survivor," last revised Nov. 27, 2017, retrieved on Jul. 8, 2020, retrieved from URL<https://www.cancer.org/cancer/laryngeal-and-hypopharyngeal-cancer/after-treatment/follow-up.html>, 4 pages.

Johns Hopkins Medicine, "Dysphagia Treatment: Swallowing Therapy," retrieved on Jul. 8, 2020, retrieved from URL<https://www.hopkinsmedicine.org/otolaryngology/specialty_areas/voice_center/dysphagia-treatment.html>, 3 pages.

Pauloski, "Rehabilitation of Dysphagia Following Head and Neck Cancer," Phys. Med. Rehabil. Clin. N. Am., Nov. 2008, 19(4):889-928.

Tidball, "The Eight Domains of Total Force Fitness—Military Families, Lethality, and Resilience," Military Families Learning Network, Mar. 15, 2019, retrieved from URL<https://militaryfamilieslearningnetwork.org/2019/03/15/the-eight-domains-of-total-force-fitness-military-families-lethality-and-resilience/>, 10 pages.

U.S. Non-Final Office Action in U.S. Appl. No. 16/800,933, dated May 20, 2020, 27 pages.

Wikipedia.org [online], "Machine learning," last edited Feb. 10, 2020, retrieved on Feb. 10, 2020, retrieved from URL<https://en.wikipedia.org/wiki/Machine_learning>, 23 pages.

Rauter, S. et al., "How to Deal with Sports Activity Datasets for Data Mining and Analysis," Intl. Journal of Advanced Pervasive and Ubiquitous Computing (Apr. 2015) 13 pp. (Year: 2015).

U.S. Final Office Action in U.S. Appl. No. 16/781,582, dated Jan. 28, 2021, 23 pages.

U.S. Non-Final Office Action in U.S. Appl. No. 16/781,582, dated Sep. 24, 2020, 21 pages.

* cited by examiner

400

| Type | Gene | Description | Conditional Positive Effect | Negative | Conditional Negative Effect (U) |
|---|---|---|---|---|---|
| S | LRP5 | Extra Strong Bones | +2 | Low Buoyancy | -1 |
| S | MSTN | Lean Muscles | +1 | | 0 |
| S | SCN9A | Insensitivity to Pain | +1 | Unnoticed Harm | -1 |
| S | FAAH-OUT | Insensitivity to Pain | +1 | Unnoticed Harm | -1 |
| R | BDKRB2 | Deep Diving | +2 | | 0 |
| R | EGLN1 | High Altitude | +1 | | 0 |
| R | EPAS1 | High Altitude | +1 | | 0 |
| R | MTHFR | High Altitude | +1 | | 0 |
| B | BHLHE41 = DEC2 | Less Sleep | +2 | | 0 |
| B | GLUK4 | High Cognitive | +1 | | 0 |
| R | PDE10A | Breath hold Diving | +1 | | 0 |
| C | HBB | Malaria Resistant | +2 | Sickle Cell Trait* Linked to sudden death during training | -1 |

S = Strength
C = Cardiovascular
R = Respiratory
U = Undesirable
B = Brain

FIG. 4

Scoring Table 500

| Criteria | Information | Equation | Min X | Max X | Target 1 | Target 2 |
|---|---|---|---|---|---|---|
| 1 | VO2Max | 15.3 x (MHR/RHR) | 38 | 96 | 46 | 52 |
| 2 | Deadlift | (1/5)x+32 | 160 | 340 | 200 | 270 |
| 3 | Power Throw | (40/8.9)x+(350/8.9) | 4.6 | 13.5 | 9.2 | 10.9 |
| 4 | Pushup | (2/3)x+(160/3) | 10 | 70 | 41 | 60 |
| 5 | Sprint | (-8/23)x+(3100/23) | 3:35 | 1:40 | 2:50 | 2:25 |
| 6 | Pull-up | (40/19)x+(1100/19) | 1 | 20 | 7 | 14 |
| 7 | 2 mile run | (-20/251)x+(40400/251) | 21:07 | 12:45 | 16:20 | 14:55 |

PRIMARY
- Dashboards ▾

SECONDARY
- Settings
- < Collapse Menu

Highlights | List View | Post Study | App Content

All Participants 902

All the participants enrolled in the program

| Patient ID | ↑Name | ↓Completion % | ↑Pain Levels | ↑Intensity | ↑Day of Program | ↑Readiness Score |
|---|---|---|---|---|---|---|
| 00578647 | Johnny Cage | ● 0% | 5 | Low | 10 | 1/10 ⌄ |
| 5456775 | Liu Kang | ● 0% | 5 | Medium | 7 | 2/10 ⌄ |
| 3463721 | Sonya Blade | ● 25% | 5 | Low | 12 | 3/10 ⌄ |
| 3234567 | Mileena P. | ● 25% | 4 | High | 15 | 4/10 ⌄ |
| 0987980 | Kurtis Stryker | ○ 50% | 4 | Medium | 20 | 4/10 ⌄ |
| 1242312 | Jaxx Briggs | ○ 50% | 4 | High | 10 | 5/10 ⌄ |

🔍 Search by name, ID, etc.   904a   Adherence ⇵

906
● Study Levels
☑ Standard
☑ Maintenance
☑ Finished

908
☐ > 2 days active
☐ ≥ 2 days inactive
☐ >5 days inactive
☑ ≥2 days adherent

---

All the participants enrolled in the program 904b

| Patient ID | ↑Name | ↓Completion % | ↑Pain Levels | ↑Intensity | ↑Day of Program | ↑Readiness Score |
|---|---|---|---|---|---|---|
| 00578647 | Johnny Cage | ● 0% | 5 | Low | 10 | 1/10 ⌄ |
| 5456775 | Liu Kang | ● 0% | 5 | Medium | 7 | 2/10 ⌄ |
| 3463721 | Sonya Blade | ● 25% | 5 | Low | 12 | 3/10 ⌄ |
| 3234567 | Mileena P. | ● 25% | 4 | High | 15 | 4/10 ⌄ |
| 0987980 | Kurtis Stryker | ○ 50% | 4 | Medium | 20 | 4/10 ⌄ |
| 1242312 | Jaxx Briggs | ○ 50% | 4 | High | 10 | 5/10 ⌄ |

🔍 Search by name, ID, etc.   Adherence ⇵

Week 5 Assessment 1104

Prior Assessment Data 1106

Likely to Reach 8/10 Readiness Score? Yes — 1110

Expected date to reach 8/10 Readiness Score? Week 8 day 3 — 1112, 1114

| Week: | 1 | 2 | 3 | 4 |
|---|---|---|---|---|
| Prior Readiness Scores | 4/10 | 5/10 | 5/10 | 6/10 |
| Performance Trend | N/A | 1 | 0.5 | 0.67 |
| Prior Risk Scores | 4/10 | 4/10 | 5/10 | 4/10 |
| Weekly Exercise Completion | 80% | 85% | 70% | 90% |
| Pain Levels | 4/5 | 4/5 | 3/5 | 3/5 |
| Feeling | Bad | Bad | Bad | Good |

Current Metrics 1108

Exercise Completion % Week 5: 88% — 1116

Average Pain Level Week 5: 3/5 — 1118

Average Feeling Week 5: Good — 1120

(SEE RESULTS) — 1122

---

Week 5 Assessment Results

Hi John,

Your current predictive readiness is 7/10 and your current risk score is 3/5. You are on track to reach a readiness of 8/10 by the beginning of Week 8. If you want to reach a readiness of 8/10 by Week 7, please consider adding one of the recommended options below to your program. — 1124

Option A: modify daily run from 3:00 min run to 1 mile run
  - New Date: Week 7, Day 3  — 1126

Option B: replace Deadlift exercise with (i) front squat exercise and (ii) back extension exercise
  - New Date: Week 7, Day 5  — 1128

FIG. 11

SYSTEMS AND METHODS FOR USING MACHINE LEARNING TO IMPROVE PROCESSES FOR ACHIEVING READINESS

GOVERNMENT LICENSE RIGHTS

This invention was made with government support under SBIR grant HHSN261201700003C awarded by the National Cancer Institute. The government has certain rights in the invention.

BACKGROUND

Some computer systems make estimates or predictions about the expected duration of a process, such as an application installation or file transfer. Some systems may estimate when a subject will reach a certain state, such as a state of operability or completion of a task. In practice, however, the accuracy of these estimates is often low, and performance varies widely from one task to the next, even for estimates regarding short, simple tasks.

SUMMARY

In some implementations, a computer system is configured to use machine learning techniques to predict when and if a subject will reach a desired level of readiness, e.g., a desired state or degree of ability needed to perform a task or achieve an objective. In general, the desired level of readiness may involve the subject acquiring a capability to perform certain actions or functions. The desired level of readiness may represent the completion of a specific task, and thus readiness to perform another activity. As another example, separate from any individual task, the desired level of readiness may refer to acquiring the capability to perform a task, even if one has not been attempted or initiated. In addition, or as an alternative, the desired level of readiness may involve the subject reaching a certain physical state or configuration (e.g., some predetermined status or condition of the subject).

The computer system can use various techniques, including machine learning techniques, to generate a variety of predictions regarding readiness of a subject. For example, the computer system can use a machine learning model to predict when a subject will reach a certain level of capability to be able to perform a task or will achieve another result (e.g., to complete a task in progress). Similarly, the computer system can use a machine learning model to predict whether a subject will reach the level of capability under certain conditions, such as within a defined time period, within an amount of time, or given a certain amount of resources. As another example, the computer system can use a machine learning model to predict whether a subject will ever be able to achieve the level of capability given various factors, which may include resources allocated to the subject and/or activities (e.g., current or planned) designed to enhance the capabilities of the subject. As another example, the computer system can use a machine learning model to predict how long a subject will maintain readiness, with or without activities planned to assist in maintaining the desired capabilities. The computer system can also use machine learning techniques to provide other outputs, such as scores that indicate a predicted measure of readiness (e.g., level of capability) of the subject at the current time or at a future time. As the system collects information and makes predictions, it can update its models to learn from the additional examples and feedback received.

In some implementations, the computer system can use machine learning techniques to evaluate and recommend actions for enhancing the readiness of a subject. This can include, for example, recommending actions to take to improve readiness, indicating the impact of specific actions on readiness of the subject, identifying factors that support or hinder readiness of the subject, evaluating different options for building capabilities of the subject, predicting the progression or trend of readiness for the subject under different conditions, and so on. Thus, besides predicting when and if a subject will achieve readiness, the computer system can assess and recommend options to improve the process of achieving readiness, e.g., to allow the subject to reach readiness faster or to reach a higher level of capability.

The system is capable of providing predictions regarding readiness, as well as recommendations for improving readiness, for many types of subjects and for many different types of readiness. For example, the subject may be a computer system, a phone, a mobile device, software, a vehicle, a robot, an item being fabricated, a factory, an organization, a person, a team of people, and so on.

In general, the system can be applied in many fields, in order to predict when a subject will achieve a desired state of readiness or capability. The desired state may be defined in terms of physical structure or composition, such as a physical arrangement of a mechanical system, a physiological and/or psychological state of a person, etc. In addition, or as an alternative, the desired state may be defined in terms of functional ability, such as the ability of a device to perform a task, a result of generating a file or data output, a capability of a person to perform a task, etc.

Readiness can be different for different subjects, and can refer to a subject achieving a physical state and/or functional state. Readiness may be defined and measured in different ways, for example, with respect to physical attributes of a subject, functional capabilities of a subject, levels of experience or prior activities performed by the subject, and so on. In the example of a computer system as the subject, readiness may represent the computer system achieving a certain level of processing capability (e.g., acquiring the capability to be able to perform tasks of a predetermined type, or to perform the tasks with a desired level of speed or efficiency). As another example of a person as the subject, readiness may represent the person reaching a certain level of health or physical fitness, obtaining a level of proficiency at a skill, etc. Readiness may span many different dimensions, such as the case of readiness to take on a particular job role, where readiness may have components of level of experience, physical capabilities, knowledge level, skills acquired, and so on.

For each of various applications, one or more models can be generated based on example data sets. The data sets can provide examples describing the process by which other subjects achieved readiness. For example, the data sets may describe the progression of various individual subjects toward achieving a capability or state. The data sets can show examples that were successful in achieving readiness, as well as examples that were not successful. A computer system can use the patterns and characteristics of the various examples to generate models that can be used to predict the readiness of other subjects based on various factors. Examples of factors that can be used for prediction are current and former attributes of the subject, current and former capabilities of the subject, time-series data indicating data points showing a pattern or trend of attributes or capability levels over time, current and previous activities of the subject, attempts or actions by the subject to perform tasks as well as corresponding outcomes, future activities of the subject (e.g., actions inferred, planned, and/or scheduled) which can include potential future training of the subject, future physical changes to the subject (e.g., a hardware upgrade for a device, a maintenance action for a vehicle, a surgical intervention for a person, etc.). These techniques, and others discussed below, allow the system to make predictions high accuracy and high precision, with the versatility to predict many types of subjects and types of readiness.

The one or more models can be machine learning models, for example, a neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used.

The techniques discussed herein are useful in many different industries and technical fields. For example, computer systems may use the techniques to predict completion of a complex task, such as compiling and linking a large software application. Rather than using milestones or an equation to predict when the task will be complete, models can be trained to predict completion times using training data examples indicating the steps needed for similar tasks (e.g., compiling other software applications) and their actual completion times. This allows the system to model many other factors, such as the likelihood of errors, severity of errors, the contributions of delays when user input may be needed in the process, and so on. Because the model(s) can take into account these and other factors, as observed over a range of different actual examples, predictions from the models regarding computing tasks can be much more accurate and precise than using typical techniques.

The techniques are also applicable to industrial settings. For example, the system may be used to predict when a factory under construction will be achieve a level of capability, such as being fully functional to produce a component or to reach production at a desired volume or rate. Models can be trained based on examples of other actual factory construction projects, including not only the final time of completion but the progressions of progress and the events during the construction process (e.g., involving change requests, variability in completion timing, differing amounts of resources available for different projects, etc.). As a result, the models can be used to generate accurate predictions about the current and future state of a project, as well as show how a project's progression relates to other prior projects, and what steps can be taken to improve readiness to achieve its purpose.

The system is also applicable to the medical field, where information about many different patients can be used to determine when a patient is ready to begin or discontinue a treatment (e.g., physical therapy, surgery, medication, digital therapeutics, etc.). For example, information about many individuals health progression over time can be captured, along with information about the patients and their lifestyle. Treatments and other activities can also be identified. This information can be used, for example, to model the progression of recovery from a health condition to predict when the patient will be ready to discontinue or lessen treatment, or to model the progression of a disease (e.g., a degenerative or progressive disease) to predict when the patient will be ready for further intervention (e.g., surgery, higher dose of medication, a change in medication, etc.). More generally, the techniques may be used to model and predict when an individual will, for example, achieve capability to perform a physical task (e.g., a task being trained through occupational therapy or rehabilitation), reach a desired level of proficiency at an activity (e.g., be able to run a mile within a target time duration), a reach a certain state of health (e.g., to lower blood pressure to a target level), change a behavior (e.g., to reduce or stop smoking), be ready for a treatment (e.g., be ready to begin swallow therapy after throat cancer surgery), and so on. Beyond the medical field, the techniques can be used for modeling and predictions of training individuals to acquire skills, abilities, health, wellness, etc. along any of various dimensions (e.g., physiological, psychological, mental, intellectual, emotional, financial, spiritual, etc.).

The system is applicable to research efforts, as a tool to assist researchers and facilitate scientific discovery. In this case, the system may be leveraged to benefit researchers in designing, monitoring, and enhancing a study such as a clinical trial, a cohort study, or other research endeavor. For example, the subject whose readiness is monitored may be a research study that is ongoing or is under development. For example, the system may be used to predict the likelihood of completion of the study by individual participants (e.g., compliance with study requirements or adherence to a plan). As another example, the system may be used to predict the likelihood that a study having certain parameters will to reach a desired outcome or progress to a desired level (e.g., have a minimum number of participants reporting a target level of data for a target amount of time, or acquire an amount of data to provide a statistically significant result, etc.). The system may be used to predict whether a study specification and/or proposed cohort will likely achieve study objectives. In other words, the readiness criteria for a research study can be, among other options, a readiness of a study to acquire a desired set of data or a readiness to be able to answer a research question. For example, the models can be used to predict when parameters for a study being designed and/or composition of a cohort being defined are ready so that, if used, are predicted to achieve at least a minimum level of confidence that the study requirements will be successfully completed by at least a minimum number of participants.

The system can be made available through various different methods. For example, the functionality to track and enhance readiness, as well as to obtain and implement interventions, may be initiated or managed by different parties. One example is a consumer-driven approach, where individual users can seek access to the system to obtain support in improving their health, athletic performance, skills, or other capabilities. The data collection, predictions, and recommendations of the system can be provided through a web page, a web application, a computer application, a mobile device application, etc. For example, a user may download an application for a mobile device, e.g., from an application store, and the application can provide the functionality for setting goals of target capability, predictions for achieving that capability, and interventions over time to help the user reach the target. Another example for providing the features of the application is through an invitational model. For example, the system can be made available in a business-to-business offering, so that employees can be invited to participate as part of an employee wellness program. As another example, a doctor may invite or instruct a patient to use the system through a clinical prescription or recommendation.

There are many ways that the system can be used to provide advantages to different parties. For example, precision predictions can be useful for a subject (e.g., an individual or participant whose readiness is monitored and predicted) and for an observer (e.g., a coach, employer, insurer, doctor, researcher, etc.). Different parties may use the system in different ways to obtain different outcomes. An individual may desire to use the system to improve his or her health or skill. An employer may desire to use the system to increase the wellness of employees, to build teams with desired capabilities, or qualify for affordable insurance. A researcher may be interested in obtaining highly accurate predictive models, with interventions for individuals being of less importance.

For example, the system may be selected by an individual to produce benefits for the individual, e.g., improved predictability and assistance in reaching a better state of health, wellness, or capability. When the focus is the individual, the key outcome of the system may be interventions that can assist the user to improve, including by personalizing and tailoring the individual's training plan, progression, or goals according to the values the individual holds. For instance, some users may select to increase human performance traits (e.g., increased strength, decreased weight, increase muscle to fat ratios). Other users may select to obtain an improved life span and quality of life.

As another example, the system can be used by a coach, doctor, physical therapist, or other person as an aid to help others improve their capabilities. The system's ability to predict capability levels, as well as predict a personalized progression of capability over time, can be particularly valuable. Similarly, the system can evaluate plans to predict the likely effects, enabling a coach or other person to simulate how different plans are likely to affect the progression of different individuals. The system can also provide value by indicating specific recommendations that are individually tailored to each individual whose capability is being assessed.

As another example, the system can be used by a business or other organization to achieve benefits for the organization. For a sports team, the key outcome may be to adjust components across a group of individuals, to create the best team as a whole. For a business, the outcome or readiness that is sought may be to qualify for an affordable insurance plan when considering a representative group model, by achieving favorable averages across certain traits.

As another example, the system can be used in research as a tool used in order to achieve scientific discovery gains. When the focus is the research, the outcome may be the creation of a highly accurate model and the relationships that the model highlights, and not necessarily the interventions that could be created for individuals. With a research focus, models may suggest changes to a particular study, such as a difference in cohort, demographics, or other aspects, that lead to expanding the research study to obtain improved accuracy and precision in the model. The improved models generated in this manner, or the relationships identified in this way, may in turn be used to better provide predictions to individuals, organizations, and others.

In general, the techniques in this document can compare measurement data, for example, self-reported data or data captured by a sensor or device, and then select an algorithm or model in order to score an individual or group for their effective performance readiness. When the subject is a person, the model or algorithm can be used to score or predict human performance readiness. The precision readiness scoring provides the ability then to perform an intervention either automatically or through manual review in order to bolster adherence and outcomes and further improve readiness. The system optionally supports a bring-your-own-algorithm (BYOA) option, in which third-party models and systems can be connected or integrated to enhance or extend the capabilities of the system.

In general, a computer system receives data indicating attributes and/or activities of a subject and uses this data to determine a prediction with respect to the subject. The prediction may be made with respect to one or more readiness criteria, which specify a target level of readiness that the subject is progressing toward. The prediction may be provided in the form of a readiness score indicating of a subject's current readiness with respect to the criteria or the subject's future readiness (e.g., at a future date, or after the passage of a predetermined time such as one month in the future). Estimates of current capability of a subject are still considered to be a prediction, for example, because the current level of capability is often not directly measurable or verifiable based the input data, and so the level is inferred based on contextual and historical factors, for example, by trained machine learning models. The system may predict, for example, (i) whether the subject is likely to reach a threshold level of readiness or other outcome, (ii) whether the subject is likely to reach the target outcome (e.g., if the subject is capable of reaching the target, potentially given some constraints or conditions), and/or (iii) a time when the subject will reach the threshold readiness score or other performance criteria.

In some implementations, the system may use the data about the subject generate a trend or progression of capability of the subject toward reaching the one or more readiness criteria. The system may use the generated trend in determining a readiness score, a likelihood of reaching a threshold readiness score or other performance criteria, whether the threshold readiness score or other performance criteria will be reached by a certain time, whether the threshold readiness score or other performance criteria is likely to be reached at all, and/or a time to reach the threshold readiness score or other performance criteria. For example, the system may compare the trend (e.g., curve or progression of readiness) for a subject with the trends of other subjects to determine how the subject compares. From this comparison, the system can determine how to change a plan for the user to reach readiness, such as by adding, altering, or removing training activities, changing communication patterns, suggesting physical changes to a subject (e.g., altering device configuration, supporting behavior changes for diet and exercise for a person, etc.), etc.

In one general aspect, a method performed by one or more computers includes: accessing, by the one or more computers, a database to obtain status data that indicates activities or attributes of a subject, the status data comprising data provided from by an electronic device to the one or more computers over a communication network; deriving, by the one or more computers, a set of feature scores from the status data for the subject, the set of feature scores including values indicative of attributes or activities of the subject; providing, by the one or more computers, the set of feature scores to one or more models that have been configured to predict readiness of subjects to satisfy one or more readiness criteria; generating, by the one or more computers and based on processing performed using the one or more models and the set of feature scores, a prediction indicating (i) a predicted time that the subject will achieve readiness to satisfy the one or more readiness criteria or (ii) whether the subject will achieve readiness to satisfy the one or more readiness criteria; and based on the prediction, providing, by the one or more computers, output data that is configured to alter a user interface of a device or to alter interaction of a device with the subject.

In some implementations, the one or more models comprise one or more machine learning models.

In some implementations, the readiness criteria comprise at least one of: a physical state of the subject; a functional state of the subject; or a level of capability of the subject to perform a task.

In some implementations, the one or more models comprise at least one of a neural network, a support vector machine, a classifier, a regression model, a clustering model, a decision tree, a random forest model, a genetic algorithm, a Bayesian model, or a Gaussian mixture model.

In some implementations, the one or more models have been trained based on training data indicating (i) activities or attributes of other subjects and (ii) outcomes for the other subjects with respect to the readiness criteria, and the training uses the respective progressions of readiness of the other subjects over time to configure the one or more models to predict readiness of subjects to satisfy one or more readiness criteria.

In some implementations, the database comprises data generated for the subject over a period of time, the status data comprising information about activities or attributes of the subject at multiple points in time. The set of feature scores derived from the status data comprise measures of the activities or attributes of the subject at each of the multiple points in time.

In some implementations, the subject is a device, a system, a model, a research study, a hardware component, a software module, an organization, a team, or an individual.

In some implementations, the set of feature scores is based on sensor data that is acquired by one or more sensors during one or more activities of the subject or that indicates one or more attributes of the subject.

In some implementations, the subject is an individual, and wherein receiving status data comprises receiving at least one of heart rate data for the subject, oxygen saturation data for the subject, data indicating an exercise distance for the subject, data indicating an exercise intensity for the subject, or data indicating a duration of an exercise for the subject.

In some implementations, generating the prediction comprises generating output indicating a predicted time that the subject will achieve readiness to satisfy the one or more readiness criteria.

In some implementations, generating the prediction comprises generating output indicating whether the subject will achieve readiness to satisfy the one or more readiness criteria.

In some implementations, generating the output indicating whether the subject will achieve readiness to satisfy the one or more readiness criteria comprises: generating output indicating whether the subject will achieve readiness to satisfy the one or more readiness criteria, the output being generated to predict an outcome based on one or more constraints that comprise a limit on at least one of: a time to achieve readiness; resources available to the subject; or a training plan for the subject.

In some implementations, providing the output data comprises providing at least one of: a score indicative of the prediction for display on a user interface; an indicator of the prediction for display on a user interface; visualization data, generated using the prediction, for illustrating a timeline or trend of predicted readiness of the subject over time; a recommendation, determined based on the prediction, of an action to improve or accelerate acquisition of readiness of the subject to satisfy the one or more readiness criteria; one or more interactive user interface controls to alter one or more planned actions for assisting the subject to achieve readiness to satisfy the one or more readiness criteria; one or more interactive user interface controls to select from among multiple options for assisting the subject to achieve readiness to satisfy the one or more readiness criteria; or an indication of a predicted change in readiness of the subject, relative to a level of readiness indicated by the prediction, for each of one or more actions with respect to the subject.

In some implementations, the method includes: tracking, by the one or more computers, (i) attributes or activities of each of multiple subjects over a period of time and (ii) changes in levels of capability of the multiple subjects over the period of time; and training, by the one or more computers, the one or more models based on the tracked data.

In some implementations, the subject is a group of individual subjects, wherein the one or more readiness criteria comprises one or more group readiness criteria, and wherein receiving status data comprises receiving activity data indicating activities of individual subjects in the group. The method further includes: generating, based on the activity data, a readiness score for each of the individual subjects in the group, the readiness scores indicating predictions of the respective capabilities of the individual subjects in the group; and generating a group readiness measure that indicates a predicted ability of the group of individual subjects to collectively satisfy the one or more group readiness criteria.

In some implementations, providing output comprises providing, based on the group readiness measure, output indicating (i) a predicted time that the group will achieve readiness to satisfy the one or more group readiness criteria or (ii) a likelihood or prediction whether the group will achieve readiness to satisfy the one or more group readiness criteria given one or more constraints.

In some implementations, the method includes: receiving new activity data indicating activities of the subjects in the group; generating, based on the new activity data, a new readiness score for each of the subjects in the group; generating a new group readiness measure; and providing, based on the new group readiness measure, new output indicating (i) a new predicted time that the group will achieve readiness to satisfy the one or more group readiness criteria or (ii) a new likelihood or prediction whether the group will achieve readiness to satisfy the one or more group readiness criteria given one or more constraints.

In some implementations, the method includes determining that the new output indicates that (i) the new predicted time is less than the predicted time, or (ii) that the new likelihood is higher than the likelihood.

In some implementations, the method includes determining that the group readiness measure does not satisfy a threshold; and in response to determining that the group readiness measure does not satisfy the threshold, performing at least one of: removing from the group one or more subjects determined to have individual readiness scores that are less than an average of individual readiness scores for subject in the group; or adding to the group one or more subjects having individual readiness scores that are greater than an average of individual readiness scores for subject in the group.

In another general aspect, a method performed by one or more computers includes: accessing, by the one or more computers, a database to obtain status data that indicates activities or attributes of a subject, the status data comprising data provided by an electronic device to the one or more computers over a communication network; generating, by the one or more computers, one or more readiness scores indicating a level of capability of the subject to satisfy one or more readiness criteria, the one or more readiness scores being generated using one or more models trained based on data indicating patterns of acquiring readiness by other subjects; accessing, by the one or more computers, data indicating multiple candidate actions for improving capability of the subject to satisfy one or more readiness criteria; selecting, by the one or more computers, a subset of the candidate actions for the subject based on the one or more readiness scores generated using the one or more models; and providing, by the one or more computers, output configured to (i) cause one or more of the actions in the selected subset to be performed by the one or more computers or another system or (ii) cause an indication one or more of the actions in the selected subset to be presented on a user interface of the one or more computers or another system.

In some implementations, the one or more models comprise one or more machine learning models.

In some implementations, the one or more readiness criteria comprise at least one of: a physical state of the subject; a functional state of the subject; or a level of capability of the subject to perform a task.

In some implementations, the one or more models comprise at least one of a neural network, a support vector machine, a classifier, a regression model, a clustering model, a decision tree, a random forest model, a genetic algorithm, a Bayesian model, or a Gaussian mixture model.

In some implementations, the one or more models have been trained based on training data indicating (i) activities or attributes of other subjects and (ii) outcomes for the other subjects with respect to the readiness criteria. The training uses the respective progressions of readiness of the other subjects over time to configure the one or more models to predict readiness of subjects to satisfy one or more readiness criteria.

In some implementations, the database includes data generated for the subject over a period of time, the status data comprising information about activities or attributes of the subject at multiple points in time; and the one or more readiness scores are generated using the one or more machine learning by providing, to the one or more models, a set of feature scores, derived from the status data, that includes measures of the activities or attributes of the subject at each of the multiple points in time.

In some implementations, the subject is a device, a system, a model, a research study, a hardware component, a software module, an organization, a team, or an individual.

In some implementations, the set of feature scores is based on sensor data that is acquired by one or more sensors during one or more activities of the subject or that indicates one or more attributes of the subject.

In some implementations, accessing the data indicating the multiple candidate actions includes: accessing data indicating (i) a plurality of training options for the subject and (ii) indications of how the respective training options are predicted to affect the readiness of the subject to satisfy the one or more readiness criteria.

In some implementations, accessing the data indicating the multiple candidate actions includes accessing data indicating candidate actions comprising at least one of: changing a frequency, number, or intensity of planned training activities for the subject; changing an allocation of resources for the subject; changing a type of training for the subject; changing an assignment of an individual to assist the subject in achieving readiness; or providing, for output by a client device, a notification indicating the level of capability of the subject to satisfy one or more readiness criteria that is indicated by the one or more readiness scores.

In some implementations, accessing the data indicating the multiple candidate actions includes: generating one or more candidate actions based on information indicating available resources for training the subject and at least one of: information about the subject from the database; data indicating actions taken to improve readiness of the subject; or data indicating one or more planned future actions to improve readiness of the subject.

In some implementations, selecting the subset of the candidate actions includes: determining a score for each of the candidate actions, the scores being indicative of a predicted effect of the respective candidate actions on readiness of the subject to satisfy the one or more readiness criteria; and selecting the subset based on the scores for the candidate actions.

In some implementations, the scores for the candidate actions are determined based on data indicating changes in attributes or capabilities of one or more other subjects after actions corresponding to the candidate actions are performed for the one or more other subjects.

In some implementations, the scores for the candidate actions are determined based on data indicating previous activities of the subject and changes in attributes or capabilities of the subject after the previous activities.

In some implementations, the scores for the candidate actions are determined based on current attributes of the subject.

In some implementations, the scores for the candidate actions are determined based on planned or scheduled activities of the subject.

In some implementations, providing the output includes using the selected one or more actions in the selected subset to change a plan of future activities to increase readiness of the subject to satisfy the one or more readiness criteria.

In some implementations, providing the output includes: providing a recommendation, for presentation on a user interface of a client device, of one or more of the actions in the selected subset.

In some implementations, the method includes providing, for presentation on the user interface of the client device, at least one of: one or more interactive user interface controls configured to initiate one or more of the actions in the subset in response to user interaction with the one or more interactive user interface controls; one or more scores indicative of a predicted change to the readiness of the subject to satisfy the one or more readiness criteria; or visualization data to illustrate a timeline or trend indicating a progression of readiness of the subject to satisfy the one or more readiness criteria if one or more of the selected actions are performed.

In another general aspect, a method performed by one or more computers includes: accessing, by the one or more computers, data designating a group comprising multiple individual subjects; receiving, by the one or more computers, status data indicating attributes or activities of each of the subjects in the group, where at least some of the status data includes information provided to the one or more computers over a communication network by the subjects or from electronic devices associated with the subjects; generating, by the one or more computers, a group readiness measure based on the status data using one or more models, where the group readiness measure indicates a predicted ability of the group to satisfy one or more group readiness criteria; and based on the group readiness measure, providing, by the one or more computers, output data that is configured to alter a user interface of a device or to alter interaction of a device with one or more of the subjects in the group.

In some implementations, generating the group readiness measure includes: generating an individual readiness score for each of the multiple subjects. The individual readiness scores indicate predictions of the respective capabilities of the subjects in the group; and generating the group readiness measure based on the individual readiness scores for the subjects in the group.

In some implementations, the individual readiness scores respectively indicate predicted readiness of individual subjects to satisfy one or more individual readiness criteria, and the individual readiness criteria are different from the group readiness criteria.

In some implementations, generating the individual readiness score for each of the multiple subjects includes: for each of the multiple subjects: providing, to one or more models, a set of feature scores for the subject derived from status data for the subject obtained from a database of attributes or activities of subjects; and receiving an output that is generated for the subject in response to the one or more models receiving the set of feature scores for the subject, where the individual readiness score for the subject is based on the output.

In some implementations, generating the group readiness measure based on the individual readiness scores for the subjects in the group includes: providing the individual readiness scores to one or more models trained to generate a group readiness measure based on examples of group readiness measures and corresponding individual readiness scores for members of the group; and determining the group readiness measure based on the processing of the one or more models performed in response to receiving the individual readiness scores.

In some implementations, the group readiness measure is an average of individual readiness scores for each of the subjects in the group.

In some implementations, the group readiness measure indicates a predicted current readiness of the group to satisfy the one or more group readiness criteria.

In some implementations, the group readiness measure indicates a predicted readiness of the group to satisfy the one or more group readiness criteria at a future time.

In some implementations, the method includes adding or removing one or more subjects from the group based on the prediction or based on individual readiness scores for the subjects in the group.

In some implementations, the method includes reassigning a particular subject from the group to a different group based on the prediction or based on an individual readiness score for the particular subject.

In some implementations, the group readiness criteria correspond to at least one of: a physical state of the subjects; a functional state of the subjects; or a level of capability of the subjects to perform a task.

In some implementations, the one or more models comprise at least one of a neural network, a support vector machine, a classifier, a regression model, a clustering model, a decision tree, a random forest model, a genetic algorithm, a Bayesian model, or a Gaussian mixture model.

In some implementations, the one or more models have been trained based on training data indicating (i) activities or attributes of other subjects and (ii) outcomes for the other subjects with respect to corresponding readiness criteria. The training can use the respective progressions of readiness of the other subjects over time to configure the one or more models to predict readiness of subjects to satisfy one or more readiness criteria.

In some implementations, the subjects comprise a device, a system, a network, a model, a research study, a hardware component, a software module, an organization, a team, or an individual; and the status data is based on sensor data that is acquired by one or more sensors during one or more activities of the subjects or that indicates one or more attributes of the subjects.

In some implementations, generating the group readiness measure includes generating output indicating a predicted time that the group will achieve readiness to satisfy the one or more group readiness criteria.

In some implementations, generating the group readiness measure includes generating output indicating whether the group will achieve readiness to satisfy the one or more group readiness criteria.

In some implementations, generating the output indicating whether the group will achieve readiness to satisfy the one or more readiness criteria includes: generating output indicating whether the group will achieve readiness to satisfy the one or more group readiness criteria, the output being generated to predict an outcome based on one or more constraints that comprise a limit on at least one of: a time to achieve readiness; resources available; or a training plan for the group or one or more subjects in the group.

In some implementations, providing the output data includes providing at least one of: a score indicative of the prediction for display on a user interface; an indicator of the prediction for display on a user interface; visualization data, generated using the prediction, for illustrating a timeline or trend of predicted readiness of the group or one or more subjects in the group over time; a recommendation, determined based on the prediction, of an action to improve or accelerate acquisition of readiness of the group to satisfy the one or more group readiness criteria; a recommendation, determined based on the prediction, of an action to improve or accelerate acquisition of readiness of one or more subjects in the group to satisfy one or more individual readiness criteria; one or more interactive user interface controls to alter one or more planned actions for assisting the group to achieve readiness to satisfy the one or more group readiness criteria; one or more interactive user interface controls to select from among multiple options for assisting the group to achieve readiness to satisfy the one or more readiness criteria; or an indication of a predicted change in readiness of the group, relative to a level of readiness indicated by the prediction, for each of one or more actions with respect to the subject.

In another general aspect, a method performed by one or more computers includes: receiving, by the one or more computers, status data indicating attributes or activities of a subject, the status data comprising sensor data acquired by one or more devices associated with the subject; accessing, by the one or more computers, data indicating multiple different analysis techniques to assess readiness with respect to one or more readiness criteria; selecting, by the one or more computers, one of the multiple different analysis techniques based on data received by the one or more computers that indicates a user input to a user interface; using, by the one or more computers, feature data derived from the status data to generate, according to the selected analysis technique, a measure of predicted readiness of the subject to satisfy one or more readiness criteria; and providing, by the one or more computers, output data that updates the user interface based on the measure of predicted readiness of the subject or causes an interaction with one or more devices based on the measure of predicted readiness of the subject.

In some implementations, the multiple different analysis techniques comprise multiple different models.

In some implementations, the multiple different models comprise models trained based on different sets of training data or using different training parameters.

In some implementations, the multiple different models comprise models of different types, and at least two of the different types are selected from the group consisting of a neural network, a support vector machine, a classifier, a regression model, a reinforcement learning model, a clustering model, a decision tree, a random forest model, a genetic algorithm, a Bayesian model, and a Gaussian mixture model.

In some implementations, at least some of the multiple models have been trained to make predictions of readiness with different levels of variance.

In some implementations, at least some of the multiple models have been trained to make predictions based on differing combinations of input features representing different sets of information about the subject.

In some implementations, the method includes: based on the accessed data indicating the multiple different analysis techniques, providing, for display on a user interface, an indication of each of the multiple different analysis techniques; and receiving data indicating user interaction with the user interface that selects one of the multiple different analysis techniques. Selecting one of the multiple different analysis techniques includes selecting the analysis technique indicated by the user interaction with the user interface.

In some implementations, the method includes comprising providing, for display on a user interface, data indicating different predictions of readiness for a subject. The different predictions can each be generated using a different one of the multiple different analysis techniques.

In some implementations, the measure of predicted readiness of the subject is generated based on data indicating planned or scheduled activities to increase a capability of the subject.

In some implementations, the measure of predicted readiness of the subject is generated based on data indicating previous activities performed by the subject that were assigned to the subject to increase a capability of the subject.

In some implementations, each of the multiple analysis techniques uses example data indicating (i) activities or attributes of other subjects and (ii) outcomes for the other subjects with respect to at least one of the one or more readiness criteria. The analysis techniques can predict readiness of subjects to satisfy one or more readiness criteria based on progressions of readiness of the other subjects over time as indicated in the example data.

In some implementations, providing the output data includes providing at least one of: a score indicative of the measure of predicted readiness for display on a user interface; an indicator of the measure of predicted readiness for display on a user interface; visualization data, generated using the measure of predicted readiness, for illustrating a timeline or trend of predicted readiness of the subject over time; a recommendation, determined based on the measure of predicted readiness, of an action to improve or accelerate acquisition of readiness of the subject to satisfy the one or more readiness criteria; one or more interactive user interface controls to alter one or more planned actions for assisting the subject to achieve readiness to satisfy the one or more readiness criteria; one or more interactive user interface controls to select from among multiple options for assisting the subject to achieve readiness to satisfy the one or more readiness criteria; or an indication of a predicted change in readiness of the subject, relative to a level of readiness indicated by the measure of predicted readiness, for each of one or more actions with respect to the subject.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIGS. 4 and 5 are diagrams that illustrates examples of tables of data that can be used for predicting or assessing readiness.

FIGS. 9A-9E are diagrams that illustrate example interfaces.

FIGS. 10-11 is a diagram that illustrates example interfaces.

Like reference numbers and designations in the various drawings indicate like elements.

DETAILED DESCRIPTION

Figure 1A:
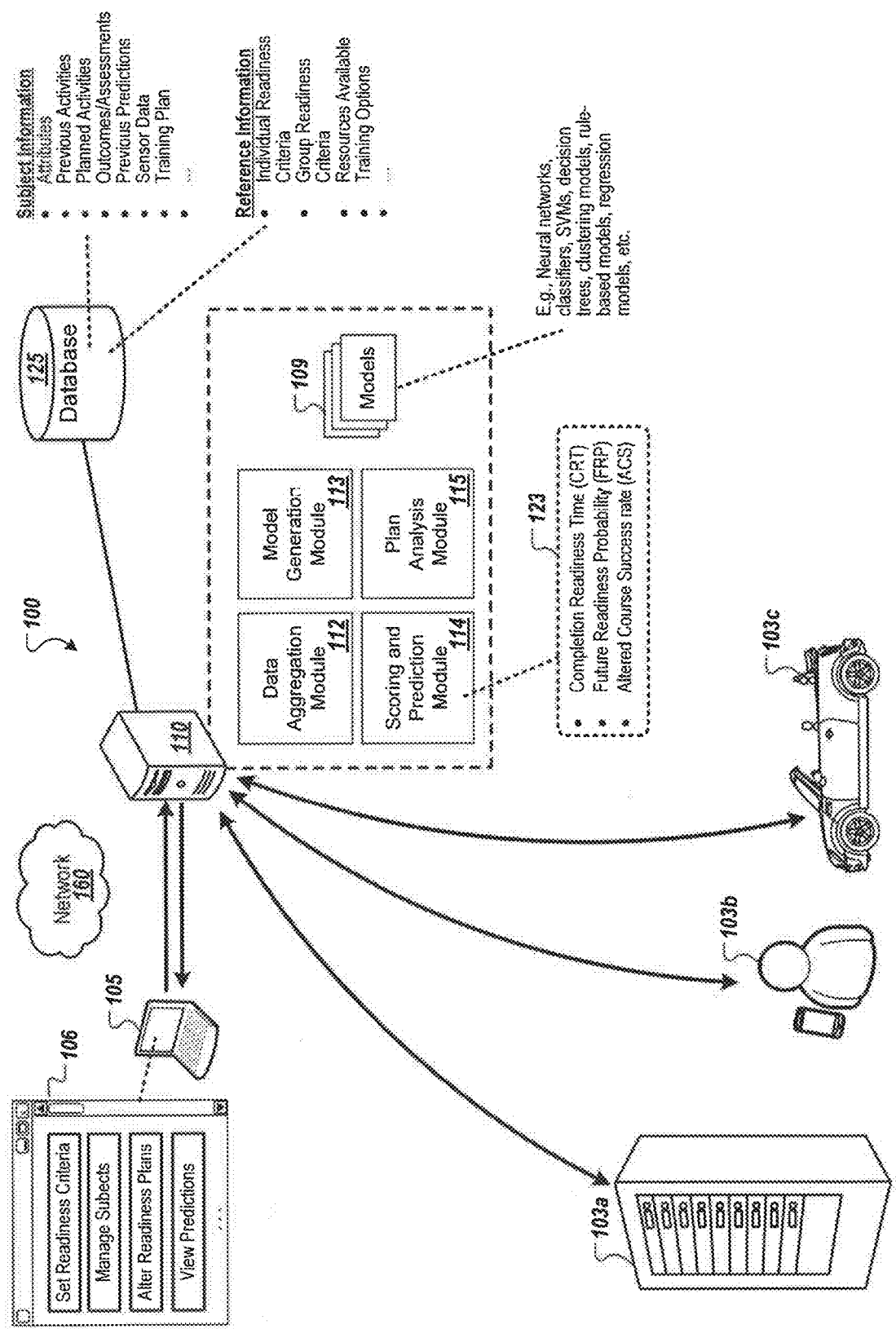
FIGS. 1A-1C are diagrams that illustrate an example system for generating precision predictions of readiness.

In some implementations, a system provides the ability to predict and improve the readiness of a subject for a task or activity. In general, readiness refers to a state in which a subject has an ability to perform an action or function.

Readiness can thus refer to a capability of a subject, e.g., the power or ability to perform an action, operation, function, task, etc. Readiness may additionally or alternatively refer to the physical and/or functional state of a subject that permits the subject to perform in a certain way or at a certain level. Readiness can be assessed with respect to one or more readiness criteria, e.g., a predetermined specification of capabilities that can be used as a reference. As used herein, the use of the term "readiness" can refer to a state of satisfying applicable readiness criteria, such as by a subject possessing the capability to prospectively perform a predetermined task or activity.

Many types of subjects have varying states and varying capabilities over time. For example, computers experience hardware configuration changes and software updates that may increase or decrease capability to perform certain types of operations. As another example, a building under construction undergoes many actions over time in order to reach full capability for its purpose, whether for housing, office space, industrial use, and so on. As another example, individual people vary in their capabilities over time, especially as they are involved in processes intended to improve their capabilities, for example, physical training, medical treatment, acquisition of a skill, etc. As another example, organizations and teams often involve combinations of people and equipment, where the group of people and equipment available changes and the capabilities of each person or device may also vary over time, resulting in different levels of capability of the organization or team as a whole.

To provide precision predictions of readiness of a subject, a computer system can collect data about various subjects and how their readiness (e.g., capabilities) vary over time. This data can include attributes of subjects and activities of the subjects over time, as well as other information indicating contextual information and other circumstances. With the data, the computer system can generate models, e.g., machine learning models or rule-based models, that model the progression of readiness of subjects (e.g., the acquisition of capabilities by the subjects) over time and the factors that enhance and detract from readiness. With these models, the computer system can use status data about a subject, e.g., attributes and/or activities of the subject, to make predictions about the current and future readiness (e.g., capabilities) of the subject. These predictions cam be made with respect to one or more readiness criteria, which specify a target level of capability for the subject to achieve. For example, the predictions can indicate a current level of readiness of the subject, a future level of readiness of the subject, a time (e.g., a date) that the subject is expected to achieve readiness, an estimated trajectory of readiness improvement by the subject, and whether the subject is likely to ever satisfy the readiness criteria. Other predictions can include how long a subject will maintain readiness after achieving readiness, a likelihood that readiness will be maintained (e.g., for a certain duration of time or to a certain time), whether certain actions will improve the maintenance of readiness, and so on.

Predictions may be made based on certain constraints or assumptions used for purpose of the analysis, such as the subject following a current training plan or having availability of certain limited resources (e.g., time, equipment, power, materials, etc.). The computer system can use readiness predictions and stored data to identify and recommend changes to enhance the readiness of a subject. For example, if the computer system identifies that a subject is not predicted to achieve applicable readiness criteria by a target time, the computer system may identify interventions to increase readiness. These interventions can be, at least in some cases, activities, resources, communications, plan changes, and other actions that are personalized for the subject based on the analysis of or models learned from data about the progression of other subjects in acquiring readiness.

As an example, if a particular subject is predicted to lack readiness, the computer system can identify resources that were used by other subjects that (i) achieved the same or similar readiness criteria applicable for the particular subject and (ii) had similar attributes and/or past activities as the particular subject. The computer system can then select and initiate actions that the computer system predicts will improve the readiness of the particular subject. These actions may include changing resources available to the subject, recommending an action to the subject or another person, initiating communications with devices, causing changes to user interfaces, and so on. The computer system can thus leverage a machine learning techniques to provide recommendations or interventions that are calculated to, for example, reduce the predicted time for the subject to meet the readiness criteria and/or to increase the likelihood of the subject meeting the readiness criteria.

Figure 1B:
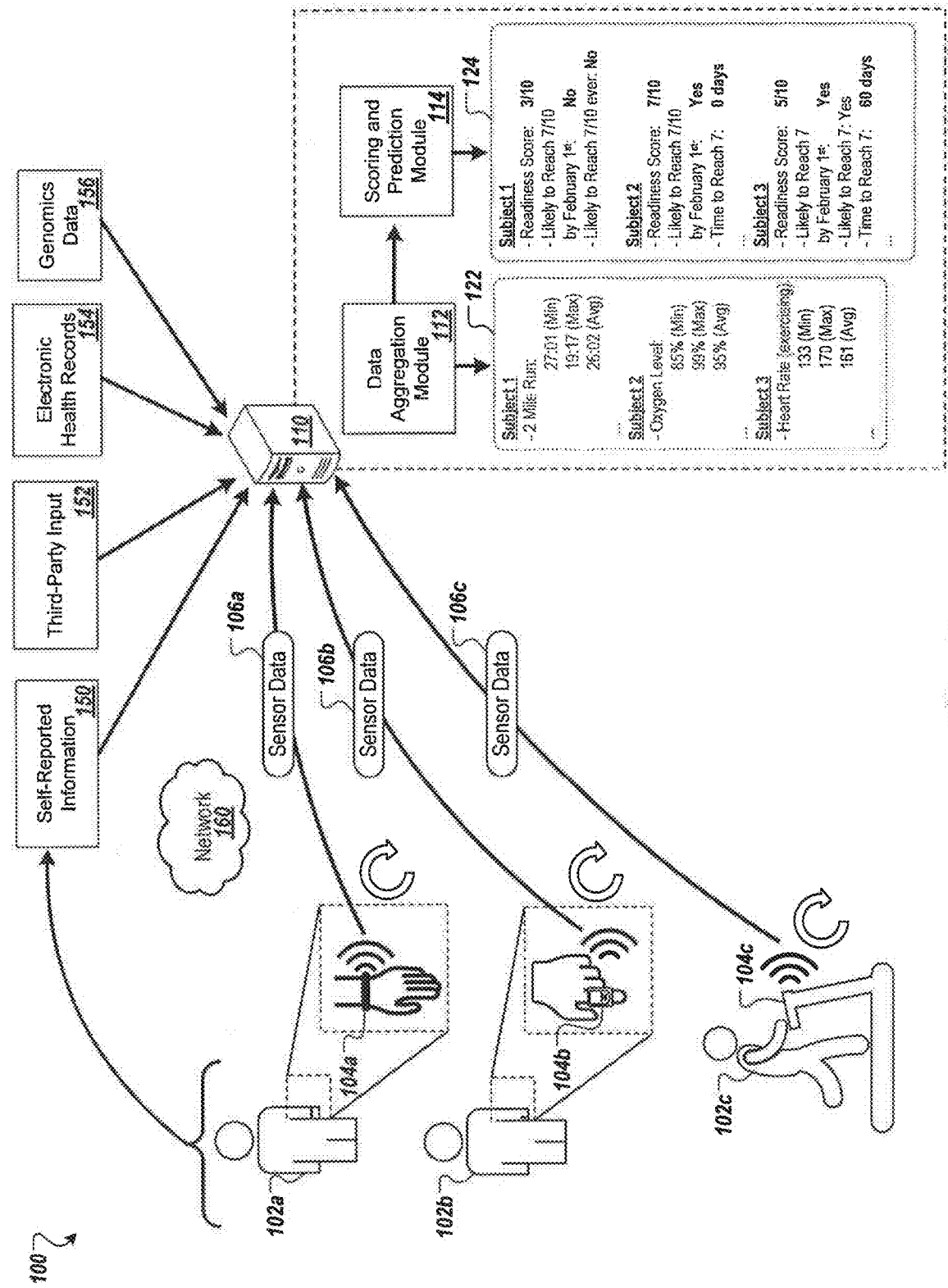
Figure 1C:
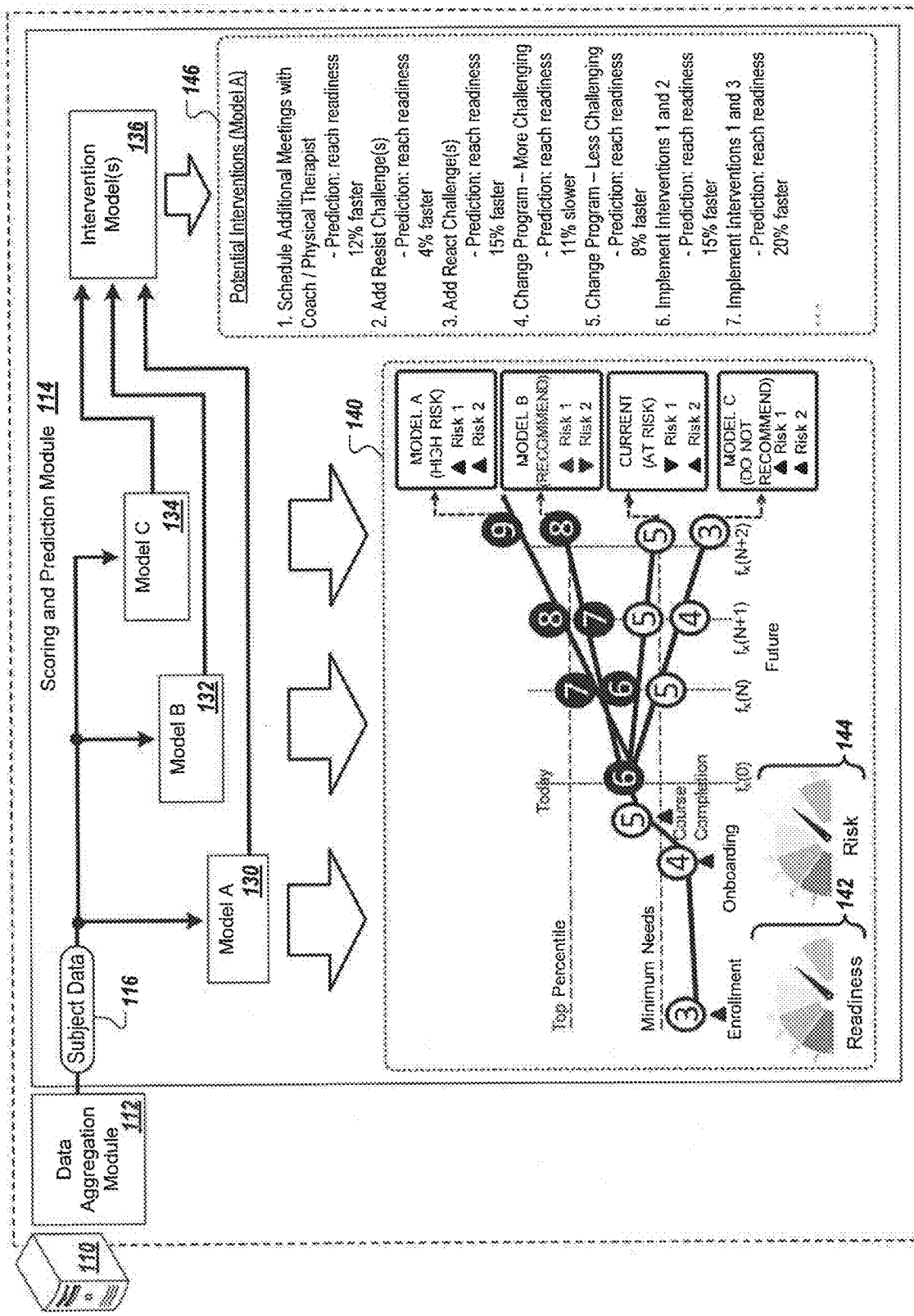

FIGS. 1A-1C are diagrams that illustrate an example system 100 for generating precision predictions of readiness. FIG. 1 shows a computer system 110 that includes functionality to predict readiness and provide information and adjustments to improve readiness. FIG. 1A shows various functions of the computer system 110 and interactions to predict and enhance a diverse set of subjects 103a-103c. FIG. 1B shows an additional example, in which the computer system collects data for and generates predictions for subjects 102a-102c that are people being trained. FIG. 1C shows functionality of the computer system 110 to generate various types of predictions using different models, as well as to identify candidate actions and select actions to improve readiness of subjects.

As illustrated in FIG. 1, the computer system 110 has access to a database 125 and also communicates with a client device 105 over a network 160. The computer system 110 provides data to the client device 105 to enable a user to set readiness criteria, manage subjects, alter readiness plans (e.g., training plans, maintenance plans, etc.), view predictions, and otherwise interface with the computer system 110.

The system can be used to predict and enhance readiness of many types of subjects. Examples of subjects include, a device, a system, a network, a fleet, a model (e.g., such as a machine learning model being trained), a research study (e.g., a research study being designed or is ongoing), a hardware component, a software module, an organization, a team, or a person. In some implementations, the subject can be a computing device, a machine learning model, a robot, or other device that can expand its capabilities (e.g., through hardware configuration changes, software updates and configuration changes, machine learning training, etc.). In some implementations, the subject is a person, a group of people, a team or group of people, and so on who can improve their capabilities (e.g., health, capabilities, skills, etc.) through various activities. In some implementations, the subject may be a combination of various individual subjects, such as a group of people along with various items of equipment that collectively form a team or unit.

In the example of FIG. 1A, the subject 103a is a computer system, the subject 103b is a person that uses a mobile device, and the subject 103c is a vehicle. Each of these different subjects can have a different set of capabilities to be acquired or developed. For example, for the computer system 103a, the readiness criteria may specify a target level of capacity and throughput for data processing. For the person 103b, the readiness criteria may specify achieving certain health indicators (e.g., weight, blood pressure, etc.) and/or abilities (e.g., ability to run a mile in less than a maximum time limit). For the vehicle 103c, the readiness criteria may specify achieving a target emissions level or reaching full function over the course of repair work. The computer system 110 can collect data about each of the subjects 103a-103c over time and provide predictions and assistance for the subjects to reach their respective desired states or functional capabilities.

Some or all of the functions of the computer system 110 can be performed by a server system. In some implementations, functions of the computer system 110 may be implemented on a cloud computing platform (e.g., Amazon Web Services (AWS), Microsoft Azure, and so on).

The network 160 can include public and/or private networks and can include the Internet. The network 160 may include wired networks, wireless networks, cellular networks, local area networks, wide area networks, etc.

The database 125 provides data storage and retrieval capabilities to the computer system 110. The database 125 may include, but is not required to include, one or more of a relational database, a centralized database, a distributed database, a data warehouse, a noSQL database, an object-oriented database, a graph database, a cloud-computing database, a data repository, a data lake, etc.

The computer system 110 is configured to receive data about subjects from a variety of sources and store the data in the database 125. The computer system 110 can monitor subjects and their progress in achieving readiness and collect the data in the database 125. The collected data may come from the subjects themselves, or from devices associated with the subjects. The collected data may come from a variety of sensors, e.g., temperature sensors, cameras, microphones, accelerometers, pressure sensors, optical sensors, and so on. Some data about the subject may be provided manually by a user, for example, through a user interface, a text message, an email message, a voice input, etc.

Some data collected in the database 125 is obtained as devices automatically send reports of conditions detected, for example, in response to detecting certain conditions or periodically (e.g., with consistent updates at a defined interval). Some data collected in the database 125 can be obtained in response to interactions initiated by the computer system 110, for example, to request sensor data, to provide a form or survey to a user, to initiate a test or evaluation of a subject, and so on. As the computer system 110 obtains data about subjects and learns the factors that are predictive of readiness, the computer system 110 may adjust the types of data that are collected for different subjects. For example, the computer system 110 may identify certain types of data or certain survey questions as relevant to a particular capability based on the collected data for some subjects, and in response may instruct devices to collect those types of data for other subjects for which the capability is also monitored.

The system 100 allows for the accurate and efficient evaluation of subjects. For example, by collecting sensor data from a variety of sensing devices, the system 100 can obtain wide range of data that more accurately represents the performance of the subject. Accuracy is also increased by collecting data repeatedly over a period of time, which allows a more accurate view of the progression of readiness than single observations. This can allow for determining a current performance of a subject with higher accuracy, and the more accurate tracking of the subject's performance over time, which can be used in developing historical trends.

Using the data in the database 125, the computer system can generate models 109 that can be used to make predictions about the current and future readiness of subjects. For example, a model generation module 113 can generate and train machine learning models, statistical models, rule-based models, and other types of models. Examples include neural networks, support vector machines, classifiers, reinforcement learning models, regression models, clustering models, decision trees, random forest models, genetic algorithms, Bayesian models, and Gaussian mixture models. The models 109 can be generated for the readiness criteria that a user provides, allowing the types of predictions and criteria for assessing readiness to be customized for each application.

The readiness criteria can be predetermined standards that indicate a target state or level of capability to be achieved. For example, the readiness criteria may specify a physical or functional state that a subject should achieve. As another example, the readiness criteria may specify a task or activity that the subject should be able to perform. Thus, the readiness criteria can serve as a reference level or threshold level of capability against which the abilities of the subject are measured.

Once the models 109 have been generated, the computer system 110 uses the models 109 to generate predictions 123 of readiness for subjects. For example, the computer system 110 includes a scoring and prediction module 114 that can generate various types of predictions. One example, is a predicted completion readiness time (CRT), which can represent a predicted time that the subject will reach readiness with respect to predefined readiness criteria. Another example is a future readiness probability (FRP), which can represent a likelihood or probability that the subject will reach readiness at a time in the future (e.g., a specific date or time in the future, or after a particular amount of time has passed), potentially according to some constraints or assumptions factored in. Another example is an altered course success rate (ACS), which can indicate a likelihood that a change in the training or development of the subject will succeed in allowing the subject to reach a desired level of readiness by a certain time.

Beyond predicting readiness, the system 100 can improve the likelihood of subjects reaching particular goals and/or the time it takes for subjects to reach those goals. Based on sensor data collected for a subject and the leveraging of historical trends and/or machine learning models, the system 100 can determine the likelihood of the subject reaching their goal(s) and/or the time it will take to reach their goal(s). The system 100 can further identify one or more recommendations to improve the likelihood of success and/or to reduce the time to reach the goal(s), and may provide one or more of these recommendations to the subject and/or may automatically implement one or more of these recommendations into a program for the subject.

As an example, a plan analysis module 115 can be used to evaluate a training or development plan for a subject and select interventions that are predicted to improve readiness of the subject. For example, the database 125 may indicate available resources, training options, and other actions that can improve readiness. The computer system 110 can use data characterizing the available candidate options, as well as the information about the subject in the database, to select interventions that are customized for the subject and the subject's unique progression in acquiring readiness to satisfy the applicable readiness criteria.

The system 100 can further improve the likelihood of subjects reaching their goals and/or the time it takes for subjects to reach their goals by evaluating multiple subjects and grouping the subjects based on their evaluations. When grouping subjects, the system 100 may group subjects into teams in order to maximize the number of teams that meet a group criteria, ensure that all teams meet a group criteria, and/or to generate teams that are likely to perform similarly (e.g., thereby avoiding the creation of teams that are likely to underperform). The system 100 may do this by organizing subjects into teams such that the average readiness score each of the teams is the same or similar, that the average readiness score of each of the teams is meets a threshold amount as indicated by group criteria, and/or that the majority of the teams have an average readiness score that meets a threshold amount as indicated by group criteria. However, the system 100 may organize subjects in more thoughtful ways, such as looking at specific weaknesses and strengths of subject subjects and coupling those subjects weak in a particular area with subjects who are strong in that same area.

Referring to FIG. 1B, the system 100 includes various sensing devices 104a-104c that collect sensor data 106a-106c from multiple subjects or subjects 102a-102c, and a computer system 110. One or more of the sensing devices 104a-104c may communicate with the computer system 110 over a network 160. One or more of the sensing devices 104a-104c may communicate with the computer system 110 through an intermediary device, e.g., a smart phone, a laptop computer, a desktop computer, or the like.

The sensing devices 104a-104c can include can include computing and/or wearable devices having one or more sensors. The sensing devices 104a-104c can include equipment having one or more sensors, such as workout equipment. The sensing devices 104a-104c may include, for example, a smart phone (e.g., having one or more of a GPS unit, a heart rate sensor, a clock, etc.), a smart watch or band (e.g., having one or more of a GPS unit, an optical heart/PPG rate sensor, an electrical heart rate/EKG sensor, a temperature sensor, a biochemical sensor, a clock, etc.), a chest strap (e.g., having a heart rate sensor), an ear sensor (e.g., having an oxygen sensor), a wrist sensor (e.g., having one or more of an oxygen sensor, a heart rate sensor, etc.), a finger sensor (e.g., having one or more of an oxygen sensor, a heart rate sensor, etc.), a treadmill (e.g., having a heart rate sensor, one or more sensors to track the minimum, maximum, and/or average speed during a session, one or more sensors to track the minimum, maximum, and/or average incline during a session, a clock, etc.), an elliptical or bike (e.g., having a heart rate sensor, one or more sensors to track the minimum, maximum, and/or average RPM, one or more sensors to track the minimum, maximum, and/or average resistance, a clock, etc.), etc.

In the example of FIG. 1B, the system 100 is evaluating three subjects 102a-102c. The subjects 102a-102c may be, for example, persons such as consumers, recruits, employees, potential employees, patients, trainees, etc.

The first subject 102a is wearing the sensing device 104a that is collecting sensor data 106a from the subject 102a. Here, the sensing device 104a is a smart band and collects data such as, for example, the subject 102a's current, minimum, maximum, and/or average heart rate (e.g., resting heart rate, heart rate while exercising, etc.); the minimum, maximum, and/or average time and distance that the subject 102a runs for in a given exercise session; the frequency that the subject 102a runs/exercises; etc.

The sensing device 104a may send the sensor data 106a that it collects to the computer system 110 over the network 160. The sensor data 106a may represent the sensor data that the sensing device 104a collects over a particular time period (e.g., an hour, six hours, twelve hours, a day, a week, etc.). The sensor data 106a may be sent to the computer system 110 as a single packet of information. Alternatively, portions of the sensor data 106a may be sent to the computer system 110 as they are acquired. For example, each heart rate reading taken by the sensing device 104a may be sent to the computer system 110 as soon as a result is acquired. Accordingly, a first portion of the sensor data 106a may be sent to the computer system 110 prior to a different portion of the sensor data 106a.

The second subject 102b is wearing the sensing device 104b that is collecting sensor data 106b from the subject 102b. Here, the sensing device 104a is a finger sensor and collects data such as, for example, the subject 102b's current, minimum, maximum, and/or average heart rate (e.g., resting heart rate, heart rate while exercising, etc.); the subject 102b's current, minimum, maximum, and/or average oxygen saturation (e.g., through an oxygen sensor on the sensing device 104b such as an oximeter); etc.

The sensing device 104b may send the sensor data 106b that it collects to the computer system 110 over the network 160. The sensor data 106b may represent the sensor data that the sensing device 104b collects over a particular time period (e.g., an hour, six hours, twelve hours, a day, a week, etc.). The sensor data 106b may be sent to the computer system 110 as a single packet of information. Alternatively, portions of the sensor data 106b may be sent to the computer system 110 as they are acquired. Accordingly, a first portion of the sensor data 106b may be sent to the computer system 110 prior to a different portion of the sensor data 106b.

The third subject 102c is using the sensing device 104c that is collecting sensor data 106c from the subject 102c. Here, the sensing device 104c is a piece of exercise equipment, e.g., a treadmill. The sensing device 104c collects data such as, for example, the subject 102c's current, minimum, maximum, and/or average heart rate (e.g., heart rate while exercising); the minimum, maximum, and/or average time, distance, speed, and/or incline that the subject 102a runs for in a given exercise session; the frequency that the subject 102a runs and/or walks; etc.

The sensing device 104c may send the sensor data 106c that it collects to the computer system 110 over the network 160. The sensor data 106c may represent the sensor data that the sensing device 104c collects over a particular time period (e.g., an hour, six hours, twelve hours, a day, a week, etc.). The sensor data 106c may be sent to the computer system 110 as a single packet of information. Alternatively, portions of the sensor data 106c may be sent to the computer system 110 as they are acquired. Accordingly, a first portion of the sensor data 106c may be sent to the computer system 110 prior to a different portion of the sensor data 106c.

In some implementations, data other than the sensor data 106a-106c is sent to the computer system 110. This data may include self-reported information 150 provided by the one or more of the subjects 102a-102c, third-party input 152, electronic health records 154, and genomic data 156.

The self-reported information 150 may include mental performance data. For example, this data may include results of a test administered to the subjects 102a-102c through one or more devices (e.g., smart phones, laptop computers, desktop computers, etc.). The self-reported information 150 may include an indication of completed challenges or tasks, or an indication of a failure to complete challenges or tasks for challenges or tasks that have been assigned to the subjects 102*a*-102*c*. The self-reported information 150 may include an indication of pain levels and intensities felt by the subjects 102*a*-102*c*, e.g., after exercising, after taking medication, after completing a challenge, or the like. The self-reported information 150 may be sent to the computer system 110 over the network 160.

The third-party input 152 may include data submitted by a coach, counselor, caregiver, care provider, specialist, employer, potential employer, supervisor of one or more of the subjects 102*a*-102*c* (e.g., a coach assigned to one or more of the subjects 102*a*-102*c*). The third-party input 152 may include indications of how the coach, counselor, caregiver, care provider, specialist, employer, potential employer, or supervisor believes a corresponding subject is performing, e.g., they are top of their group or class, they are an over-performer, they are an under-performer, etc. As an example, the third-party input 152 include feedback from a counselor on the mental fitness of one or more of the subjects 102*a*-102*c* based on a most recent counseling session. The third-party input 152 may be sent to the computer system 110 over the network 160.

The electronic health records 154 may include health records that are stored on an EMR system or those that are stored on personal devices, e.g., smartphones, of the subjects 102*a*-102*c*. The electronic health records 154 may be transferred to the computer system 110, e.g., over the network 160, after the corresponding subject of the subjects 102*a*-102*c* gives permission for the electronic health records 154 be transferred. In some implementations, the electronic health records 154 include health information shown the table 500 of FIG. 5 such as, for example, VO2Max. In some implementations, the electronic health records 154 includes all or part of the genomics data 156.

The genomics data 156 may include data relating to the genes of the subjects 102*a*-102*c*. The genomics data 156 may indicate whether any of the subjects 102*a*-102*c* suffer from any genetic diseases or other issues, or whether they actually are likely to benefit from their genetic makeup. As an example, the genomics data 156 may include all or part the table 400 of FIG. 4 such as, for example, the gene column.

When the computer system 110 receives the sensor data 106*a*-106*c*, the computer system 110 may provide the sensor data 106*a*-106*c* to a data aggregation module 112. The data aggregation module 112 may organize the received sensor data 106*a*-106*c*. The data aggregation module 112 may extract performance data from the received sensor data 106*a*-106*c*, and may organize the extracted performance data. For example, the data aggregation module 112 may organize the received sensor data 106*a*-106*c* and/or the extracted performance data by subject, by group of subjects (e.g., those that are applying for the same position, those that are being evaluated at the same time, those that have been assigned the same coach or counselor, etc.), by time (e.g., may aggregate the data for a subject for a given week and separate it from data collected from previous weeks), by session, and/or by the type of performance data (e.g., mental vs. physical performance, heart rate data, run data, oxygen saturation data, etc.). For example, as shown, the data aggregation module 112 has extracted performance data for each of the subjects 102*a*-102*c* and has organized the performance data by subject and by type of performance data, resulting in aggregated data 122.

The data aggregation module 112 may provide data (e.g., the aggregated data 122, the sensor data 106*a*-106*c*, self-reported information provided by the subjects 102*a*-102*c*, etc.) to the scoring and prediction module 114. The scoring and prediction module 114 may determine one or more readiness scores for each of the subjects 102*a*-102*c* based on received data. In determining a readiness score, the scoring and prediction module 114 may leverage one or more static algorithms. For example, the scoring and prediction module 114 may use a formula to calculate a readiness score for a person based on their performance or based on their performance with respect to their peers in one or more categories. In determining a readiness score, the scoring and prediction module 114 may leverage one or more machine learning models as will be discussed in more detail below with respect to FIG. 1B. For example, the scoring and prediction module 114 may use a formula and/or a first machine learning model for determining a current performance score for each of the subjects 102*a*-102*c*.

In calculating a readiness score for each of the subjects 102*a*-102*c*, the scoring and prediction module 114 may take into account the past readiness scores of the respective subject, the performance trends of respective subject, the frequency that the respective subject is meeting their respective challenges or goals, the amount of challenges or goals the respective subject has missed (e.g., may be used to determine whether or not the subject is complying with their program), self-reported information 150 corresponding to the respective subject, third-party input 152 corresponding to the respective subject, electronic health records 154 corresponding to the respective subject, genomics data 156 corresponding to the respective subject, and/or the like.

A readiness score may indicate a subject's mental performance or fitness, e.g., intelligence, mental fortitude, etc. For example, a readiness score may indicate a subject's ability to react, e.g., an ability to push-through a particular challenge and stay on the current pathway (e.g., which indicates mental fortitude of the subject), ability to work around a particular challenge and continue the original training design (e.g., which indicates intelligence and performance of the subject under pressure), ability to create an alternate an alternate pathway that results in the same performance testing outcome or objective (e.g., which indicates intelligence and creativity of the subject).

A readiness score may indicate a subject's physical performance or fitness. As an example, a readiness score may indicate a subject's ability to resist physical strain, e.g., the subject's physical endurance.

In some implementations, the scoring and prediction module 114 calculates a first readiness score that indicates that the physical performance of each of the subjects 102*a*-102*c*, and a second readiness score that indicates the mental performance of each of the subjects 102*a*-102*c*.

In some implementations, the scoring and prediction module 114 calculates an overall readiness score for each of the subjects 102*a*-102*c*. The overall score may be calculated using a physical performance score and a mental performance score, e.g., by averaging the two scores.

In some implementations, in generating one or more scores for a given subject, the scoring and prediction module 114 takes into account the readiness criteria required of the subject and/or any other goals assigned to the subject. The readiness criteria may require a particular level of mental performance, a particular level of physical performance, a particular overall level of performance, and/or a particular performance in a particular performance category (e.g., must have a resting heart rate of no more than 70 BPM, must be able to run a 6:00 min mile, must have scored greater than 85% in all math assessments, etc.). A goal may require the successful completion of a task or challenge (e.g., running ten miles every week for a month, becoming a top 20% mental performer, etc.). The readiness criteria and/or goals assigned to the subject may be provided by a coach, counselor, caregiver, care provider, specialist, employer, or potential employer.

In some implementations, the readiness criteria required of a subject is automatically assigned by the computer system 110, e.g., based on the type of subject (e.g., consumers, recruits, employees, potential employees, patients, trainees, etc.), based on the position that the subject is applying for if a potential employee, based on the position of the subject if an employee, etc.

In some implementations, one or more goals are automatically assigned to the subject by the computer system 110, e.g., based on their past or current readiness scores, based on the type of subject, etc.

The scoring and prediction module 114 may also predict one or more future readiness scores for each of the subjects 102a-102c. In predicting one or more future readiness scores, the scoring and prediction module 114 may leverage one or more machine learning models. The scoring and prediction module 114 may also make multiple predictions for each of the subjects 102a-102c corresponding to multiple future times. For example, for a given subject, the scoring and prediction module 114 may predict a first readiness score at N time in the future (e.g., one week, one month, two months, one year, etc.), a second readiness score at N+1 time in the future, a third readiness score at N+2 time in the future, etc.

In some implementations, the scoring and prediction module 114 uses multiple machine learning models to predict readiness scores. For example, as shown in the output 124 of the scoring and prediction module 114, the scoring and prediction module 114 determines a current readiness score and a number of predictions for each of the subjects 102a-102c. For example, for subject 102a, the scoring and prediction module 114 determines a readiness score of 3/10, that the they are not likely to reach set performance criteria (threshold readiness score of 7/10) by February $1^{st}$, and that they are not likely to ever reach the set performance criteria. For subject 102b, the scoring and prediction module 114 determines a readiness score of 7/10, that the they are likely to reach set performance criteria (threshold readiness score of 7/10) by February 1st, and that it will take no time for them to do so because they have already reached the set performance criteria. For subject 102c, the scoring and prediction module 114 determines a readiness score of 5/10, that the they are likely to reach set performance criteria (threshold readiness score of 7/10) by February 1st, and that it will take them about sixty days to do so based.

In some implementations, in calculating an overall readiness score, the scoring and predication module 114 takes into account predicted scores as well as the current and/or past readiness scores. For example, if a subject receives a score of 5/10 and the models predict an eventual score of 7/10, the scoring and prediction module 114 may determine an overall readiness score for the subject of 6/10.

In some implementations, the scoring and prediction module 114 calculates a performance trend for each of the subjects 102a-102c. In calculating a performance trend for each of the subjects 102a-102c, the scoring and prediction module 114 may leverage one or more static algorithms and/or one or more machine learning models. The performance trend for a subject may indicate whether the subject is likely to reach a readiness by a particular time, whether the subject is likely ever to reach readiness, an expected time when the subject is likely to reach readiness, and/or whether an intervention, e.g., a change, to the subject's program is recommended.

In some implementations, the scoring and prediction module 114 calculates a risk score in addition to a readiness score for each of the subjects 102a-102c. In calculating a risk score for each of the subjects 102a-102c, the scoring and prediction module 114 may leverage one or more static algorithms and/or one or more machine learning models. In calculating risk scores for the subjects 102a-102c, the scoring and prediction module 114 may take into account the current readiness score of the respective subject, the past readiness scores of the respective subject, the performance trends of respective subject, the frequency that the respective subject is meeting their respective challenges or goals, the amount of challenges or goals the respective subject has missed (e.g., may be used to determine whether or not the subject is complying with their program), self-reported information 150 corresponding to the respective subject, third-party input 152 corresponding to the respective subject, electronic health records 154 corresponding to the respective subject, genomics data 156 corresponding to the to the respective subject, and/or the like.

In some implementations, the computer system 110 groups the subjects 102a-102c based on the output 124 of the scoring and prediction module 114. The computer system 110 may group subjects into teams based on their readiness scores, e.g., in an effort to ensure that all teams meet a group criteria, to maximize the number of teams that meet a group criteria, to create teams having the same or similar average readiness scores, and/or in an effort to group subjects who perform poorly in a given area with one or more other subjects who exceed in that same area.

For example, the computer system 110 may use the output 124 to determine that subject 102a ("Subject 1"), the lowest performing of the subjects 102a-102c, should be grouped with subject 102b ("Subject 2"), the highest performing of the subjects. The computer system 110 may group the subject 102c ("Subject 3") with another middle performing subject, e.g., having a readiness score of 5/10. The computer system 110 may group the subjects in this manner to ensure that both teams meet a group criteria. The group criteria may be that the teams must have an average readiness score of 5/10. Here, the first team and the second team would both have an average readiness score of 5/10. Accordingly, by grouping the subjects in this manner, the computer system 110 has ensured that both teams meet the group criteria.

FIG. 1C depicts a more detailed view of the computer system 110. As shown, the data aggregation module 112 provides subject data 116 to the scoring and prediction module 114. The subject data 116 may include all or part the aggregation data 122 shown in FIG. 1B, the sensor data 106a-106c shown in FIG. 1B, and/or other data (e.g., self-reported information, information from coaches or counselors, etc.). For example, the subject data 116 may include the aggregation data 122 relating to the subject 102a shown in FIG. 1A and/or the sensor data 106a. The subject data 116 may be provided as input to one or more machine learning models. For example, as shown, the scoring and prediction module 114 provides the subject data 116 as input to a first machine learning model 130 ("Model A"), a second machine learning model 132 ("Model B"), and a third machine learning model 134 ("Model C").

The machine learning models 130, 132, and 134 may be training using historical data. The historical data may include data from previously assessed subjects, groups of subjects, and/or teams of subjects. The historical data may include an indication of the performance results for subjects, groups of subjects, and/or teams of subjects. For example, the historical data may indicate whether the subjects, the groups of subjects, and/or teams of subjects met certain performance criteria by the end of their respective programs, such as particular readiness scores by the end of their respective programs.

Collectively, the machine learning models 130, 132, and 134 may produce the output 140 for a given subject. The output 140 contains a graph where past, current, and predicted readiness scores have been plotted.

The output 140 also depicts readiness criteria that have been assigned for the subject. The readiness criteria is a minimum acceptable performance ("Minimum Needs") and corresponds with a readiness score of approximately 4.5/10. The output 140 also provides an indication of how the subject compares with top performing subjects (e.g., those subjects with the top 20%, 15%, 10%, or 5% readiness scores) as indicated by the "Top Percentile" line that corresponds with a readiness score of approximately 7.5/10. Reaching this top level of performance may be goal assigned to the subject.

The output 140 further indicates a calculated readiness score 142 and a calculated risk score 144. As shown, the readiness score 142 of 7/10 may actually be different than the current performance score 6/10. For example, the scoring and prediction module 114 may take into account the current performance as well as the output of the machine learning models 130, 132, and 134 in calculating the readiness score 142. Similarly, the scoring and prediction module 114 may take into account the current performance as well as the performance trends for the subject in calculating the readiness score 142. For example, the prior earned performance scores of 3/10, 4/10, and 5/10 indicate that the subject has a positive performance trend. Accordingly, the subject's readiness score 142 of 7/10 is greater than their performance score today of 6/10.

The machine learning models 130, 132, and 134 may output data indicating the readiness score 142 and/or the risk score 144. The readiness score 142 may be calculated by the machine learning models 130, 132, and/or 134, or by the scoring and prediction module 114 shown in FIGS. 1A-1C after receiving the output from the machine learning models 130, 132, and/or 134. In calculating the readiness score 142, or providing output indicating the readiness score 142, the machine learning models 130, 132, and/or 134 may take into account the subject's current physiological performance, psychological performance, or combination of the subject's physiological performance and psychological performance. The machine learning models 130, 132, and/or 134 may use the subject's current physiological performance and/or psychological performance to generate a base score. With respect to FIG. 1B, the physiological performance and/or psychological performance may be determined from the obtained sensor data 106, the self-reported information 150, the third-party input 152 (e.g., information provided by a coach, caregiver, potential employer, employer, supervisor, or the like), and/or the electronic health records 154.

In calculating the readiness score 142, or providing output indicating the readiness score 142, the machine learning models 130, 132, and/or 134 may also take into account the subject's past performances or past performance data. The subject's past performances may include one or more past readiness scores, one or more past risk scores, previously obtained physiological performance data of the subject, previously obtained psychological performance of the subject, or the like. The machine learning models 130, 132, and/or 134 may use the subject's past performances or past performance data to generate a performance trend for the subject and then use the trend in calculating the readiness score 142, or providing output indicating the readiness score 142. For example, if the machine learning models 130, 132, and/or 134 generate a positive performance trend (e.g., indicating that the subject's performance is improving), then the machine learning models 130, 132, and/or 134 may increase the base score in determining the readiness score 142. If the machine learning models 130, 132, and/or 134 generate a negative performance trend (e.g., indicating that the subject's performance is worsening), then the machine learning models 130, 132, and/or 134 may decrease the base score in determining the readiness score 142.

In some implementations, the machine learning models 130, 132, and/or 134 weigh certain data or calculations differently in determining the readiness score 142 (or the risk score 144). For example, with respect to FIG. 1B, the machine learning models 130, 132, and/or 134 may weigh the sensor data 106, the self-reported information 150, the third-party input 152, information within the electronic health records 154, and the subject's performance trend(s) differently in calculating the readiness score 142, or providing output indicating the readiness score 142.

In some implementations, in calculating the readiness score 142, or providing output indicating the readiness score 142, the machine learning models 130, 132, and/or 134 may take into account the genomics data 156 shown in FIG. 1A. As will be discussed in more detail below with respect to FIG. 4, the machine learning models 130, 132, and/or 134 may improve or decrease a subject's readiness score based on their positive or negative effects arising from their genetic makeup. The machine learning models 130, 132, and/or 134 may weigh the presence of particular genes differently, or may weigh the positive or negative effect of particular genes differently. For example, if the genomics data 156 indicates that the subject has a gene that makes them less sensitive to pain, the machine learning model 130 may take into account only the positive effects (e.g., insensitivity to pain may provide benefits for the mental health of the subject, may result in them being more likely to complete their exercises, may make them more fit for certain roles such as a soldier, etc.) of the gene and improve the subject's readiness score, the machine learning model 132 may take into account the positive and negative effects (e.g., insensitivity to pain may make it more difficult for the subject to notice when they hurt themselves so they are more likely to injure themselves and worsen injuries that have occurred) of the gene and not affect the subject's readiness score, and the machine learning model 134 may take into account only the negative effects and decrease the subject's readiness score.

The risk score 144 may be calculated in a similar manner as described above with respect the readiness score 142. The machine learning models 130, 132, and 134 may way various factors differently when calculating a risk score. The risk score 144 may be an average of each of the risk scores calculated by the machine learning models 130, 132, and 134, or may be an average of the risk scores determined, e.g., by the scoring and prediction module 114 shown in FIGS. 1A-1C, based on the output of the machine learning models 130, 132, and 134.

There may be situations where a subject receives a relatively high readiness score (a positive indication) but receives a relatively high risk score (a negative indication). For example, the machine learning models 130, 132, and/or 134 may determine that the risk score of a subject should be increased, despite the subject currently performing well, if their performance suddenly changes (e.g., quick increase or decrease in the subject's performance), if their performance remains stagnant for a prolonged period of time (e.g., multiple weeks or months), if their self-reported data indicates that they are experiencing high levels of pain and/or continue to experience high levels of pain, if their self-reported data indicates that they often or always feel bad after completing a program challenge, if their genomics data indicates that they are predisposed to certain, problematic medical conditions or are unlikely to perform well in certain scenarios, and/or if third-party reported data (e.g., from a coach, caregiver, potential employer, employer, supervisor, or the like) conflicts with obtained sensor data and/or self-reported data.

In some implementations, the scoring and prediction module 114 shown in FIGS. 1A-1C calculates the readiness score 142 based on the output of the machine learning models 130, 132, and 134. Various factors may affect the subject's readiness score, such as the subject's performance trend (e.g., whether the trend is positive or negative, whether the trend is positively accelerating or negatively accelerating, etc.), the performance of the subject on their program's challenges, how many challenges the subject has completed or failed to complete, the percentage of challenges the subject has completed or failed to complete, the genomics data of the subject, reported third-party evaluation data (e.g., provided by a coach, caregiver, employer, potential employer, supervisor, etc.), self-reported data, or the like.

In some implementations, the scoring and prediction module 114 shown in FIGS. 1A-1C calculates the risk score 144 based on the output of the machine learning models 130, 132, and 134. Various factors may affect the subject's risk score, such as the subject's performance trend (e.g., too quick of performance increase may indicate a higher risk as well as too slow of performance increase), how many challenges the subject has completed or failed to complete, the percentage of challenges the subject has completed or failed to complete, the genomics data of the subject, reported third-party evaluation data (e.g., provided by a coach, caregiver, employer, potential employer, supervisor, etc.), self-reported data, or the like.

In some implementations, the scoring and prediction module 114 shown in FIGS. 1A-1C includes the machine learning models 130, 132, and 134. Similarly, the scoring and prediction module 114 may include the intervention model(s) 136.

In some implementations, the output 140 may be presented on a user interface. For example, the output 140 may be presented on a user interface of a device of the corresponding subject. Similarly, the output 140 may be presented on a user interface of a device of a coach, counselor, caregiver, care provider, specialist, employer, or potential employer.

The output of the machine learning models 130, 132, and 134 may be provided to one or more intervention models 136. The intervention model(s) 136 may include one or more machine learning models. The intervention model(s) 136 may use the output of one or more of the machine learning models 130, 132, and 134 to generate and/or select recommendations or interventions for the subject.

The intervention model(s) 136 may also receive the subject data 116 as input. When the intervention model(s) 136 receives the subject data 116 as input, the intervention model 136 may use the subject data 116 to assist in generating and/or selecting recommendations or interventions for the subject.

In generating and/or selecting recommendations or interventions for the subject, the intervention model(s) 136 may estimate an impact that various recommendations or interventions will have on the likelihood of the subject meeting the readiness criteria, the estimated time it will take for the subject to meet the readiness criteria, the likelihood of the subject reaching a certain goal or task, the estimated time it will take for the subject to reach a certain goal or task, etc.

In estimating an impact that various candidate actions or interventions will have, the intervention model(s) 136 may generate an impact score for every intervention in a list of interventions. The list of interventions may be particular to circumstances of the subject. For example, there may be a set of potential interventions corresponding to physical therapy (e.g., if the subject is in physical therapy), there may be a set of potential interventions corresponding to medical treatment in general, or to particular ailments or surgeries (e.g., if the subject is a patient), there may be a set of potential interventions corresponding to employee training or evaluation (e.g., if the subject is a potential employee or is an employee), there may be a set of potential interventions corresponding to consumers (e.g., if the subject is a consumer), there may be a set of potential interventions corresponding to physical fitness requirements or military requirements (e.g., if the subject is a recruit), or the like. Military requirements may include, for example, the criteria and/or passing score(s) for the army combat fitness test (ACFT), the armed services vocational aptitude battery (ASVAB), and/or the armed forces classification test (AFCT).

The intervention model(s) 136 may determine, for example, based on the subject data 116 whether the subject is a consumer, recruit, employee, potential employee, patient, or trainee. The intervention model(s) 136 may proceed to (i) access one or more sets of potential interventions based on the whether the subject is a consumer, recruit, employee, potential employee, patient, or trainee, (ii) determine impact score(s) for one or more of the interventions (e.g., each of the interventions within each of the accessed sets of potential interventions) within the selected one or more sets of potential interventions, and, based on the impact scores, recommend one or more the interventions (e.g., to a coach, caregiver) based on the impact scores. For example, the intervention model(s) 136 may determine based on the subject data 116 that the subject is an Army recruit. Based on this information, the intervention model(s) 136 may obtain a set of potential interventions for physical fitness requirements and/or military requirements, and may determine an impact score for each of the interventions in the set(s) of potential interventions based on, for example, the subject's current readiness score 142, their risk score 144, their previous readiness score(s), and/or their readiness score trend.

The intervention model(s) 136 may also take into consideration prior interventions and how those interventions coincided with the subject's readiness scores, readiness score trend, and/or risks. As an example, if a prior intervention making the subject's program more difficult coincided with the subject receiving a lower readiness score(s) and/or a worsening of the subject's readiness score trend, then the intervention model(s) 136 may calculate an impact score for interventions that would make the subject's program more challenging that is lower compared to impact scores for interventions that would not make the subject's program more challenging (e.g., would make the subject's program less challenging).

In some implementations, in estimating an impact that various recommendations or interventions will have, the intervention model 136 may combine two or more interventions and estimate an impact the combination(s) will have.

As shown, the intervention model 136 generates output 146. The output 146 may include an indication of recommendations or interventions for the subject. For example, the output 146 may include impact scores for each of various recommendations or interventions. The scoring and prediction module 114 may use the output 146 to recommend one or more of the interventions (e.g., the three that have the highest beneficial impact score). This recommendation may be sent to a device of the subject, who may select one or more of the interventions. This suggestion may be sent to a device of a coach, counselor, caregiver, care provider, specialist, employer, potential employer, or supervisor corresponding to the subject. The coach, counselor, caregiver, care provider, specialist, employer, potential employer, supervisor may proceed to select one or more of the interventions. A selection of one of the interventions may result in change in the subject's program, program(s), challenge(s), goal(s), etc.

The scoring and prediction module 114 may use the output 146 to automatically effect a change in the subject's program, program(s), challenge(s), goal(s), etc.

In some implementations, the scoring and prediction module 114 does not include and/or leverage the intervention model 136. The output of the machine learning models 130, 132, and 134 may be provided to a coach, counselor, caregiver, care provider, specialist, employer, potential employer, or supervisor of the corresponding subject. The coach, counselor, caregiver, care provider, specialist, employer, potential employer, or supervisor may then select, e.g., through a mobile application or website, one or more recommendations or interventions to provide to the subject.

Figure 2A:
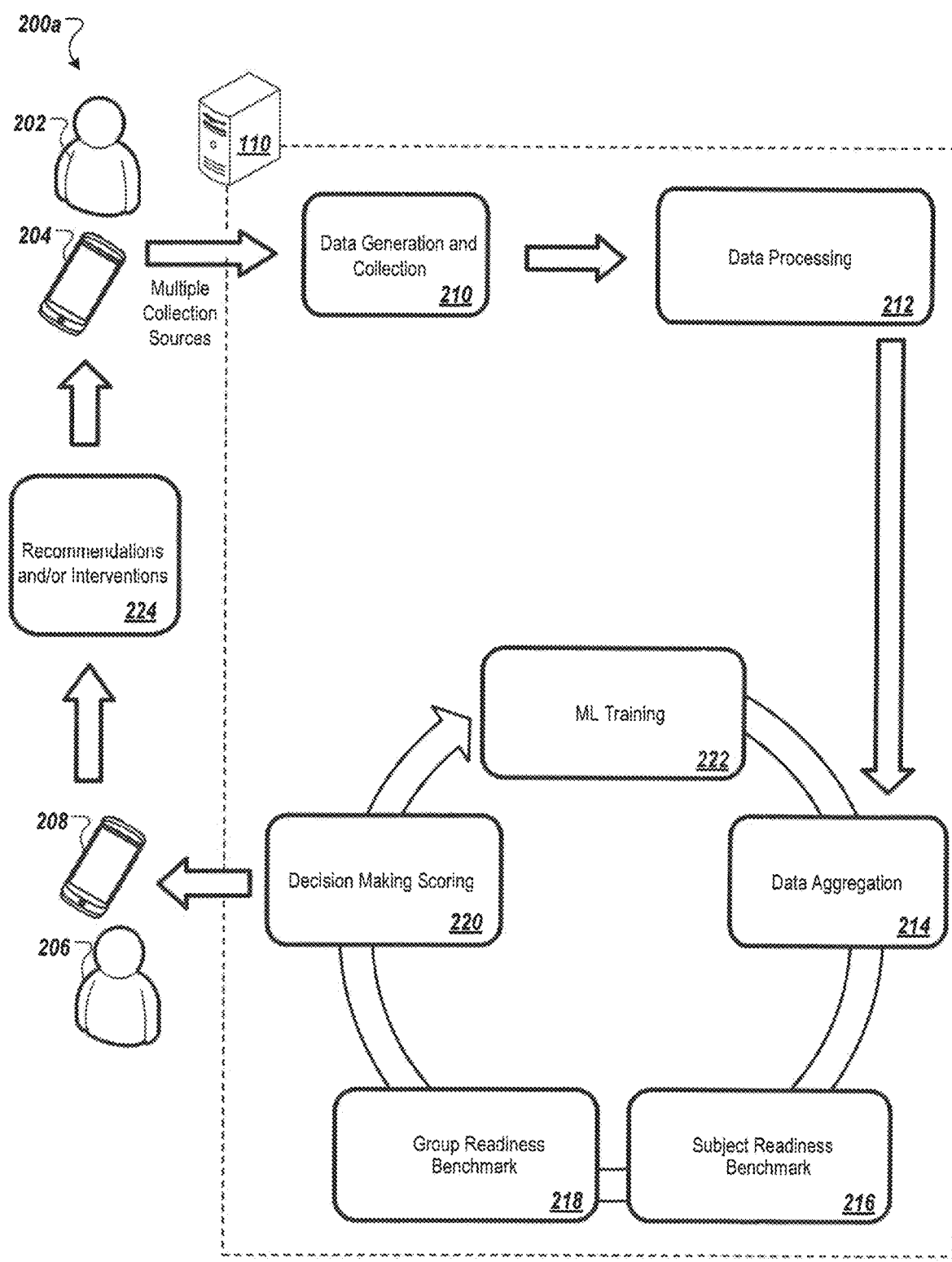
FIGS. 2A-2B are diagrams that illustrate example processes for predicting readiness.
Figure 3:
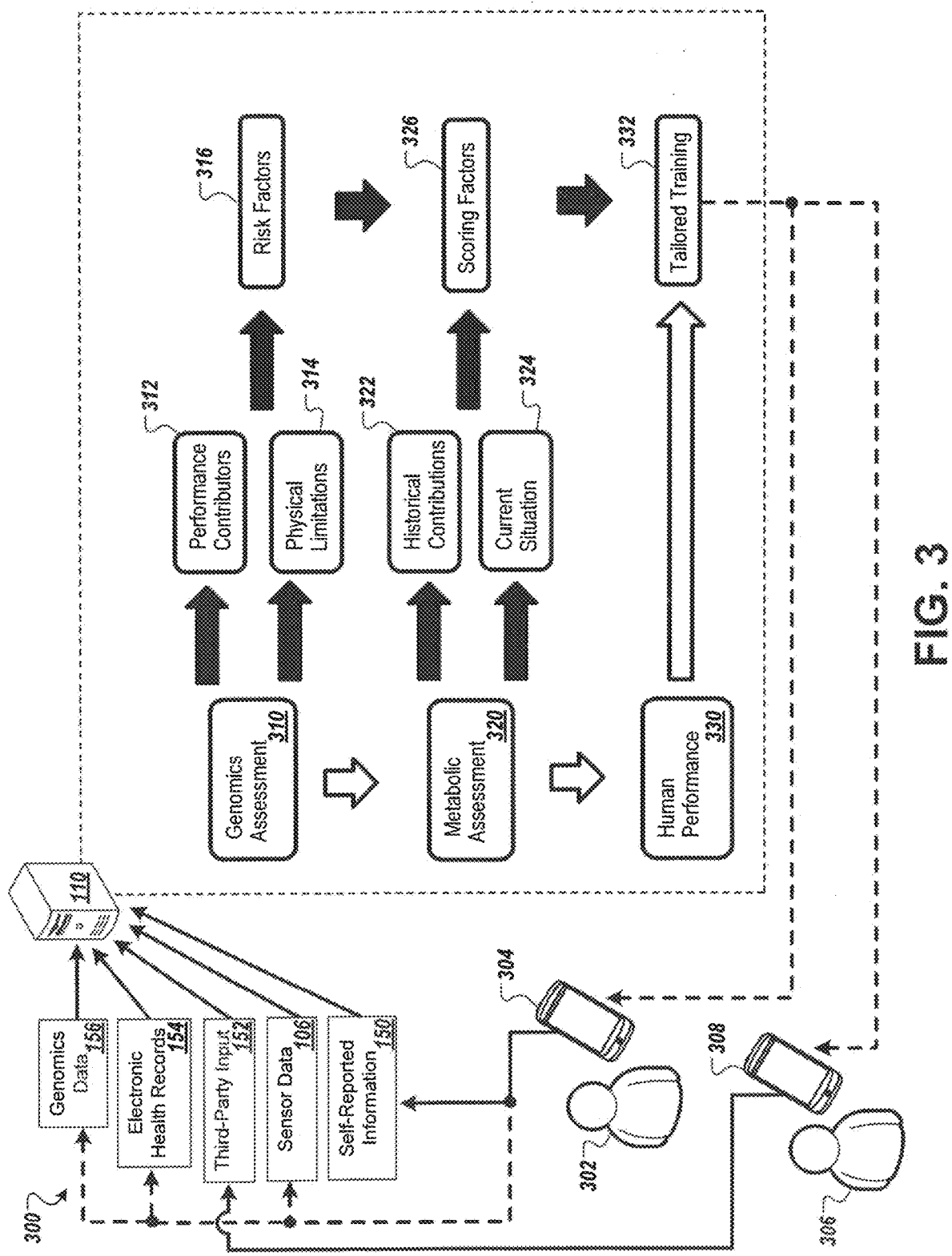
FIG. 3 is a diagram that illustrates an example process for assessing a subject.
Figure 6:
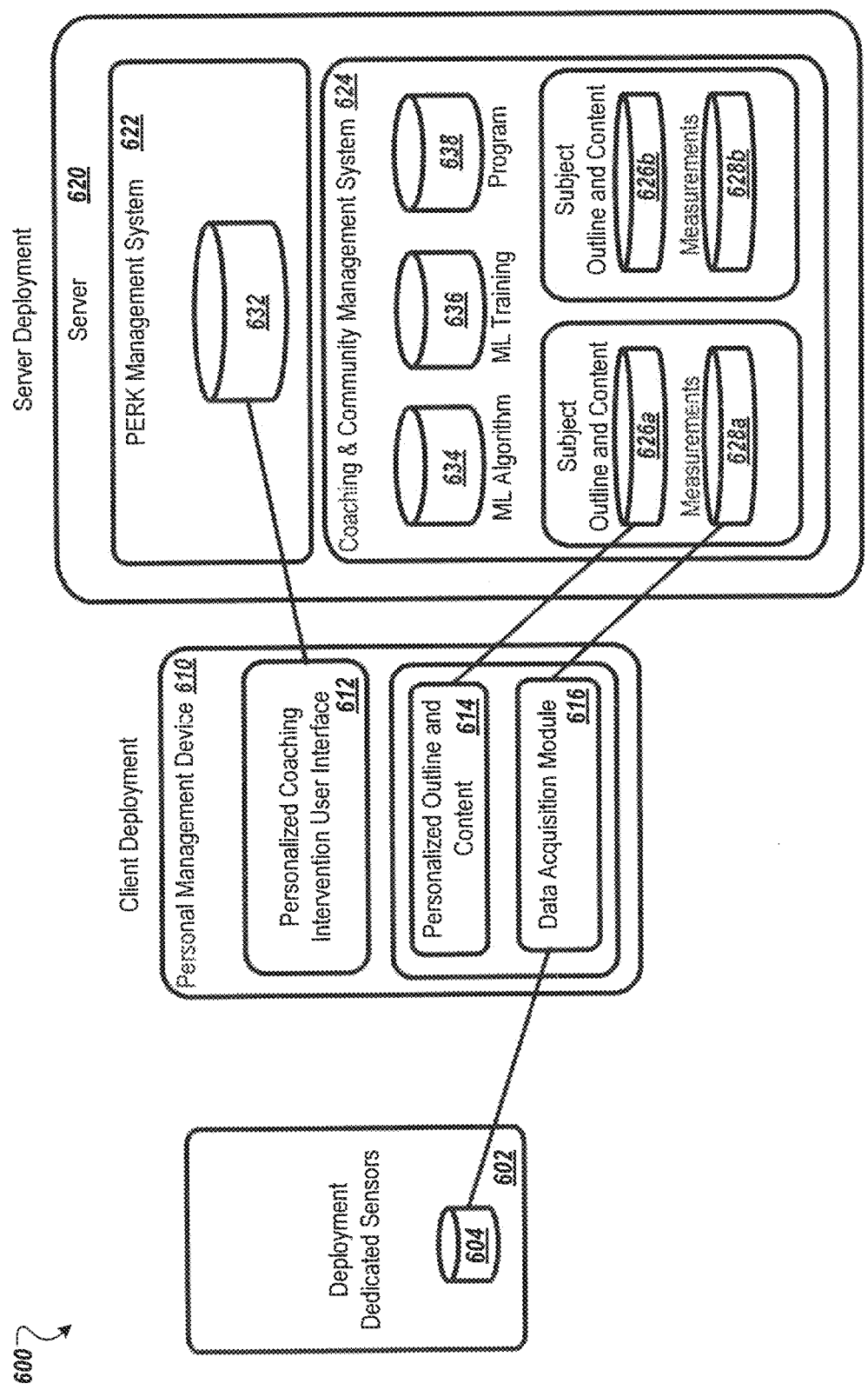
FIG. 6 is a diagram that illustrates an example system for generating precision predictions of readiness.

In some implementations, the scoring and/or predications take place locally on one or more client devices, e.g., the client device 204 shown in FIG. 2A, the client device 304 shown in FIG. 3, or the personal management device 610 shown in FIG. 6. Each of the one or more client devices may be, for example, a computing device such as a smart phone, a laptop computer, a desktop computer, a tablet, or the like. The one or more client devices may belong to the subjects 102a, 102b, and/or 102c. As an example, the scoring and prediction module 114 may be located the one or more client devices.

In some implementations, the subjects 102a, 102b, and/or 102c use the one or more client devices to provide the self-reported information 150. For example, the subjects 102a, 102b, and/or 102c may each provide program feedback through a mobile app on their respective client devices.

In some implementations, the one or more client devices are used to collect and send sensor data. For example, the client devices may include a GPS unit that can collect data indicating exercise duration and/or distance, a heart rate monitor indicating the respective subject's heart rate, a display unit to display one or more tests for the respective subject to take and that can receive touch input, or the like.

Models can be used to generate other types of predictions also, such as how long readiness of the subject will be maintained after it is achieved, whether the subject will maintain readiness for at least a minimum amount of time or until a particular a time, an extent that different candidate actions will improve the maintenance of readiness for the subject, and so on.

The system 100 is applicable to research efforts, as a tool to assist researchers and facilitate scientific discovery. In this case, the system 100 may be leveraged to benefit researchers in designing, monitoring, and enhancing a study such as a clinical trial, a cohort study, or other research endeavor. For example, the subject whose readiness is monitored may be a research study that is ongoing or is under development. For example, the computer system 110 may be used to predict the likelihood completion of the study by individual participants (e.g., compliance with study requirements or adherence to a plan). As another example, the computer system 110 may be used to predict the likelihood that a study having certain parameters will to reach a desired outcome or progress to a desired level (e.g., have a minimum number of participants reporting a target level of data for a target amount of time, or acquire an amount of data to provide a statistically significant result, etc.). The computer system 110 may be used to predict whether a study specification and/or proposed cohort will likely achieve study objectives. In other words, the readiness criteria for a research study can be, among other options, a readiness of a study to acquire a desired set of data or a readiness to be able to answer a research question. For example, the models can be used to predict when parameters for a study being designed and/or composition of a cohort being defined are ready so that, if used, are predicted to achieve at least a minimum level of confidence that the study requirements will be successfully completed by at least a minimum number of participants.

The predictions of the computer system 110 can be used to iteratively design or improve a research study. As the study design is changed, e.g., as adjustments are made to study parameters (e.g., identity of participants, number of participants, data types being measured, requirements of study participants, information gathering techniques, and so on) the computer system 110 can give updated predictions of the readiness of the study design to reach target metrics (e.g., percentage of participants complying with study requirements, an amount of time needed to gather the types of information needed, a likelihood of achieving a particular type of result, etc.). These predictions can be based on examples of other studies, e.g., parameters used for those studies, readiness or success criteria for those studies, the progression of the studies over time, and the ultimate outcomes for the studies. The computer system 110 can analyze the examples to determine relationships between different factors and outcomes and/or can use machine learning to train models that implicitly learn relationships from the data. The computer system 110 can be used to providing prediction data to a user, to show predicted measures of readiness for each different update to or version of a study design (e.g., showing changing completion likelihoods for different sets of study parameters). The computer system 110 can also be used to provide recommendations of changes to the study that may improve the readiness of the study design for implementation with high likelihood of success. This may include recommending actions to change study parameters (e.g., changing composition of a cohort, data collection techniques, study duration, etc.) based on the trends, progressions, and outcomes of other example studies for which data is included in a database. One or more models may additionally or alternatively be trained to evaluate the potential impact of different changes on future success of the study. Based on these evaluations, the computer system 110 can provide a score and/or a measure of potential benefit for each of different candidate actions, along with user interface controls to implement those candidate actions and change the study parameters.

As another example, for a research study in progress, the computer system 110 can use models that assess the progress of the study, and give updated predictions over time. As additional data for the study is tracked and monitored by the computer system 110, the computer system 110 can give updated predictions for the study, e.g., that the predicted time of obtaining a complete data set may be later than earlier predicted, or that successfully completion has become more likely given recent trends in participants' actions. Along with these predictions, the computer system 110 can provide recommended actions to improve or maintain the readiness of the study to achieve predetermined objectives expressed as readiness criteria. The computer system 110 can be used to assess the progress of a study and evaluate whether the study is progressing toward successful completion, as defined by readiness criteria for the study. The computer system 110 can also evaluate candidate actions for the research study, such as changing study parameters (e.g., information gathered, techniques for gathering information, types of interactions, questions addressed, study duration, number and identity of participants, and so on). The computer system 110 can assign scores to the candidate actions to indicate how likely each candidate action to improve the progression of the study toward successful completion. As another example, the candidate actions optionally do not changing fundamental study parameters, but may alter interaction with participants to adjust factors such as the frequency or type of reminders to study participants. These factors can be potentially customized for each individual participant, based on example data in the database about how similar types of participants have responded in other studies.

FIG. 2A is a diagram that illustrates an example process 200a for predicting readiness. The process 200a may be performed by the system 100 shown in FIG. 1A. As shown, part of the process 200a is performed on the computer system 110.

The process 200a includes generating and collecting data (210). During data generation and collection, data of the subject 202 can be obtained from multiple collections sources. The collection sources may include one or more sensing devices (e.g., the sensing devices 104a-104c shown in FIG. 1A), a client device 204 of the subject 202, a third-party device 208, and/or one or more external systems (e.g., an EMR system). For example, some of the data, such as information self-reported by the subject 202, may be obtained from the client device 204 of the subject 202. Prior to data generation and collection, the subject 202 may have been provided an initial program, e.g., through one or more recommendations and interventions, by a third-party 206. The third-party 206 may be, for example, coach, counselor, caregiver, care provider, specialist, employer, potential employer, supervisor, or the like. This initial program may not be personalized, e.g., because it is not based on data collected from the subject 202.

The process 200a includes processing the data (212). Processing the data may include extracting performance information from the data that indicates a performance of the subject 202. The performance information may indicate a physiological performance of the subject 202 and/or a psychological performance of the subject 202.

The process 200a includes aggregating the data (214). Aggregating the data may include organizing the data based on the subject 202, the type of subject that the subject 202 is (e.g., potential employee, recruit, patient, etc.), the time from when the data was collected, the type of performance information within the data, etc. The data may be aggregated by the data aggregation module 112 shown in FIGS. 1A-1C.

The process 200a optionally includes assessing the aggregated data using a subject model for a subject benchmark or readiness criteria (216). Assessing the aggregated data using a subject model may include comparing the aggregated data with readiness criteria. The assessment may indicate whether the subject 202 currently meets the subject benchmark/readiness criteria. Assessing the aggregated data may be performed by the scoring and prediction module 114 shown in FIGS. 1A-1C.

The process 200a optionally includes assessing the aggregated data using a group model for a group benchmark or readiness criteria (218), e.g., when the subject 202 belongs to a group or a team of subjects that are being evaluated. Assessing the aggregated data using a group model may include comparing the aggregated data with the group readiness criteria. The assessment may indicate whether the subject 202 currently meets the group benchmark/group readiness criteria. Assessing the aggregated data may be performed by the scoring and prediction module 114 shown in FIGS. 1A-1C.

The process 200a includes, based on the assessment(s), making one or more decisions and/or scoring the subject (220). For example, with respect to FIG. 1B, the scoring and prediction module 114 may determine a readiness score for the subject 202, a risk score for the subject 202, a performance trend for the subject 202, a determination as to whether the subject 202 is likely to meet readiness criteria (e.g., a particular readiness score), a determination as to when the subject 202 is likely to meet readiness criteria, or the like. The scoring and prediction module 114 may make these determinations using the machine learning models 130, 132, and/or 134. As another example, the scoring and prediction module 114 may determine one or more interventions for the subject 202's program in order to improve the likelihood of the subject 202 achieving readiness (e.g., by meeting the readiness criteria) or by reducing the time until the subject 202 is likely to achieve readiness. The scoring and prediction module 114 may determine these one or more interventions using the intervention model(s) 136.

The process 200a includes training one or more machine learning models (222). The one or more machine learning models may be trained using the current information such as the one or more decisions and/or scores corresponding to the subject 202, and/or using past information corresponding to the subject 202 or other subjects. With respect to FIG. 1B, the one or more machine learning models may include the machine learning models 130, 132, and/or 134, and/or the intervention model(s) 136. For example, the generated readiness score(s) for the subject 202 may be used to train the machine learning models 130, 132, or 134 and/or the intervention model(s) 136 shown in FIG. 1B.

The one or more decisions and/or scores corresponding to the subject 202 are sent to the third-party device 208 of the third-party 206. For example, the third-party 206 may be a coach of the subject 202. The third-party 206 may receive an indication of the subject 202's current readiness, an indication as to whether the subject 202 is likely to achieve readiness with their current training program, an indication of when the subject 202 is likely to achieve readiness, and/or one or more recommended interventions for the subject 202's training program.

The process 200a includes providing recommendations and/or interventions to the subject (224). For example, the third-party 206 may generate one or more recommendations and/or interventions for the subject 202 based on the one or more decisions and/or scores corresponding to the subject 202. As another example, the third-party 206 may select one or more of the interventions contained within the one or more decisions and/or scores corresponding to the subject 202. Specifically, the recommendations and/or interventions may be a subset of recommendations and/or interventions suggested by one or more machine learning models of the computer system 110. The recommendations and/or interventions can be sent from the third-party device 208 to the subject 202's client device 204, e.g., through the network 160 shown in FIG. 1A.

Figure 2B:
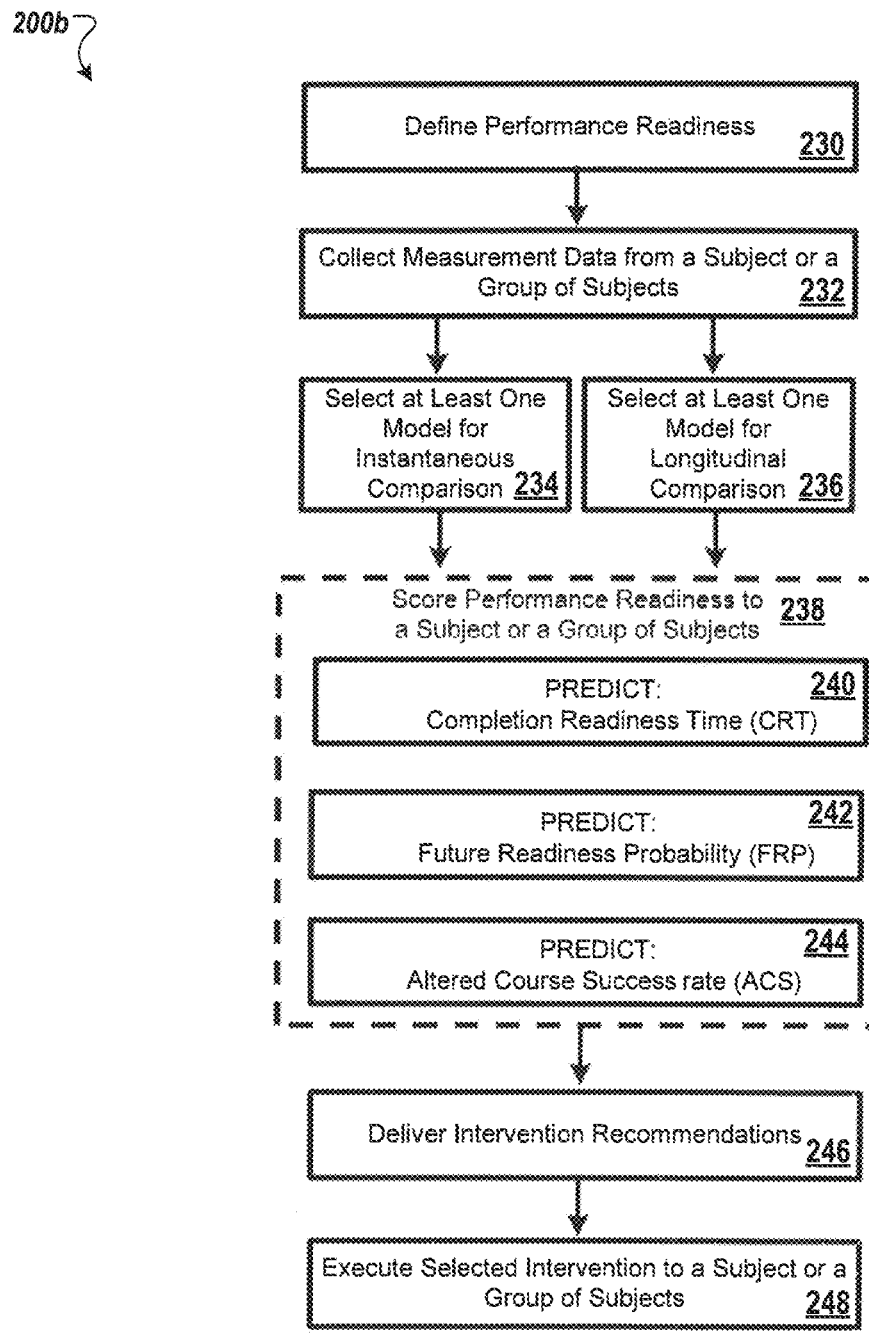

FIG. 2B is a diagram that illustrates an example process 200b for predicting readiness. The process 200b may be performed by the system 100 shown in FIG. 1A.

The process 200b includes defining performance readiness (230). Defining performance readiness may include defining one or more performance criteria. Performance criteria may include physiological benchmarks (e.g., physical performance requirements) and/or psychological benchmarks (e.g., performance on a particular examination, performance on an IQ test, etc.). Performance readiness may be defined by a third-party such as, for example, a coach, a counselor, a caregiver, a care provider, a specialist, an employer, a potential employer, a supervisor, or the like. Performance readiness may be defined for a particular subject, a particular group of subjects, or a particular team of subjects in a group of subjects.

The process 200b includes collecting measurement data from a subject or a group of subjects (232). With respect to FIG. 1B, the measurement data my include sensor data 106a, 106b, or 106c collected using sensing devices 104a, 104b, or 104c, respectively.

The process 200b includes selecting at least one model for instantaneous comparison (234). The model may be a machine learning model, such as the machine learning model 130, 132, and/or 134 shown in FIG. 1B. The at least one model selected may include a model that analyzes reactionary results based on the measurement data without comparing it to past measurement data. For example, the at least one model may analyze the measurement data along with other contemporaneously collected data. The at least one model may receive the measurement data as it is collected. For example, the at least one model may analyze the measurement data is it is received, e.g., in real-time or substantially real-time. The model(s) selected may be based on the type of subject(s), the readiness criteria for the subject(s), the third-party that set the readiness criteria, or the like.

The process 200b includes selecting at least one model for longitudinal comparison (236). The at least one model may be a machine learning model, such as the machine learning model 130, 132, and/or 134 shown in FIG. 1B. The at least one model selected may include a model that analyzes historical trends of data, such as historical trends of measurement data of the subject, the group of subjects, or a team of subjects in the group of subjects. The model(s) selected may be based on the type of subject(s), the readiness criteria for the subject(s), the third-party that set the readiness criteria, or the like.

The process 200b includes scoring performance readiness to a subject or a group of subjects (238). With respect to FIGS. 1A-1C, scoring performance readiness to a subject or a group of subjects may be performed by the scoring and prediction module 114 on the computer system 110. Scoring performance readiness to a subject or a group of subjects may be performed using the selected at least one model for instantaneous comparison, and the at least one model for longitudinal comparison.

The process 200b optionally includes predicting a completion readiness time (240). Completion readiness time can include the time it takes for a subject, a group of subjects, or team of subjects in a group of subjects to achieve readiness. For example, a completion readiness time for a subject can be the time for the subject to achieve a particular readiness score. In the case of group of subjects or a team of subjects, a completion readiness time may include the time for the group or team to achieve a particular, average readiness score, or a time for each subject in the group or team to achieve a particular readiness score.

The process 200b optionally includes predicting a future readiness probability (242). Future readiness probability can include a likelihood that a subject, a group of subjects, or team of subjects in a group of subjects will achieve readiness, or will achieve readiness by a certain time, e.g., by the end of a scheduled program. For example, a future readiness probability for a subject can be the likelihood of the subject achieving a particular readiness score. In the case of group of subjects or a team of subjects, a future readiness probability may include the likelihood for the group or team to achieve a particular, average readiness score, or a likelihood for each subject in the group or team to achieve a particular readiness score.

The process 200b optionally includes predicting an altered course success rate (244). An altered course success rate may be, for example, a likelihood that a subject, a group of subjects, or team of subjects in a group of subjects will achieve readiness, or will achieve readiness by a certain time, if a change to their respective program(s) is made. The change may include one or more interventions, e.g., outputted by the intervention model(s) 136 shown in FIG. 1C.

The process 200b includes delivering intervention recommendations (246). With respect to FIG. 1C, delivering intervention recommendations may be performed by the intervention model(s) 136 shown in FIG. 1C. The intervention recommendations may be provided to one or more client devices of a subject, a group of subjects, or a team of subjects in a group of subjects. The intervention recommendations may be provided to one or more third-party devices, such as mobile devices belonging to a coach or caregiver of the corresponding subject, group of subjects, or team of subjects.

The process 200b includes executing selected interventions to a subject or a group of subjects (248). Executing selected interventions to a subject or group of subjects may include changing the program of subject or each of the programs of a group or team of subjects based on the predictions. The program(s) may be changed automatically, e.g., by the computer system 110 shown in FIGS. 1A-2A, and 3. The program(s) may be changed manually by, for example, one or more third-parties who have accessed or been provided the predictions.

FIG. 3 is a diagram that illustrates an example process 300 for assessing a subject 302. The process 300 may be performed using the system 100 shown in FIG. 1A. Specifically, the process 300 may be performed on the computer system 110 after receiving self-reported information 150, sensor data 106, third-party input 152, electronic health records 154, and/or genomics data 156. As shown, the self-reported information 150 may be provided by a subject 302 through a client device 304. The sensor data 106 may be obtained through client device 304 or through, for example, one or more sensing devices. The electronic health records 154 may be obtained through client device 304 or through, for example, an external EMR system. The genomics data 156 may be obtained through client device 304 or through, for example, an external EMR system. The third-party input 152 may be provided by a third-party 306 through a third-party device 308.

In some implementations, the client device 304 is the client device 204 shown in FIG. 2A. In some implementations, the subject 302 is the subject 202 shown in FIG. 2A. In some implementations, the third-party device 308 is the third-party device 208 shown in FIG. 2A. In some implementations, the third-party 306 is the third-party 206 shown in FIG. 2A.

In the process 300, the subject 202 may be assessed based on genomics and metabolic analysis factors, and a tailored training program 332 may be produced for the subject 202 based on the assessment.

As shown, in the process 300, a genomics assessment 310 is performed. The genomics assessment 310 determines performance contributors 312 and physical limitations or vulnerabilities 314. The performance contributors 312 and the physical limitations or vulnerabilities 314 can be used to generate or update risk factors 316. The genomics assessment 310 can provide both positive and negative scoring into the tailored training program 332, e.g., through the risk factors 316. As an example, the table 400 shown in FIG. 4 provides an example of results from one or more genomics assessments that may be performed in the process 300.

In the process 300, a metabolic assessment 320 is performed. The metabolic assessment 320 assessment compares historical contributions 322 and the subject 302's current situation 324 to provide a deeper analysis into their given body development trends. The historical contributions 322 and the subject 302's current situation 324 can be used to generate or update scoring factors 326. The metabolic assessment 320 can influence the tailored training program 332, e.g., through the scoring factors 326. As an example, the table 500 shown in FIG. 5 provides an example of results from one or more metabolic assessments that may be performed in the process 300.

The results of the genomics assessment 310 and the metabolic assessment 320 may be combined to provide a complete human performance assessment 330 for the subject 302. The human performance assessment 330, the risk factors 316, and the scoring factors 326 may be used to develop and/or update the tailored training program 332 for the subject 302.

Machine learning models and/or artificial intelligence tools may be used in generating or updating the risk factors 316 and/or the scoring factors 326. The models and/or tools could be used to optimize the tailored training program 332 overtime, for example, based on the success and/or failure of other implemented tailored training programs in the community of subjects.

The tailored training program 332 may be optionally provided to the subject 302 through their client device 304. The tailored training program 332 may be optionally provided to the third-party 306 through their third-party device 306.

FIG. 4 is a diagram that illustrates an example table 400. The table 400 depicts the results of an example genomics assessment (e.g., the genomics assessment 310 shown in FIG. 3). As shown, the table 400 depicts how particular genes may correspond to conditional positive and/or negative effects positive. These effects, or a net effects, may be implemented as positive and/or negative scoring into the tailored training program 332 shown in FIG. 3.

As shown in the table 400, the genes may be labeled as a strength related ("S"), cardiovascular related ("C"), respiratory related ("R"), brain related ("B"), or an undesirable ("U") gene. The S labeled genes can impact the physiological strength and endurance (e.g., may indicate that a corresponding subject has a higher likelihood of successfully enduring more intense physiological related training). The C labeled genes can impact blood flow and circulatory aspects of the human body. The R labeled genes can impact air inhalation, exhalation and the delivery of oxygen throughout the body. The B labeled genes can impact cognitive functions and mental capacity, ability to replenish awareness and alertness.

Each of the genes shown in the table 400 labeled have conditional positive effects that can be applied as beneficial factors. Some of the genes shown in the table 400 also has conditional negative effects, which is indicated as (U) or undesirable outcomes, vulnerabilities, and risks. The conditional positive effects may provide an increase to the subject's score by the depicted amount if it the corresponding beneficial effect is relevant to the subject's evaluation. Similarly, the conditional negative effects may result in a decrease to the subject's score by the depicted amount if the corresponding detrimental effect is relevant to the subject's revaluation. As an example, the gene LRP5 has a conditional positive effect due to the strength related benefits that extra strong bones provide, but also has conditional negative effect due to the extra strong bones resulting in a lower buoyancy. The lower buoyancy results in conditional negative effects as it may make it more difficult for the subject to excel at swimming without specialized training. However, if swimming were not part of or related to the subject's evaluation, then the subject might not have their readiness score detrimentally affected from having the LRP5 gene.

As another example, an undesirable risk of the insensitivity to pain benefit associated with strength related genes SCN9A and FAAH-OUT is that these genes also may provide unnoticed harm. This may mean that the subject can train harder but is more likely to hurt themselves in the process (e.g., could result in an unnoticed blood clot if the subject stands for long periods, or fractures that can worsen without notice).

An undesirable vulnerability of being resistant to Malaria for the cardiovascular related gene HBB is that these genes also can be linked to a sickle cell trait. The sickle cell trait creates a risk during training that may lead to sudden death, and need further monitoring and precision tailoring of human performance training.

In some implementations, with respect to FIGS. 1A-1C, the computer system 110 receives the genomics assessment represented as the table 400 from an external database such as, for example, an EMR system. For example, the computer system 110 may receive the genomics assessment represented as the table 400 as all or part of the electronic health records 154 or the genomics data 156.

The computer system 110 may provide the genomics assessment represented as the table 400 to the data aggregation module 112. Accordingly, the genomics assessment may be used by the scoring and prediction module in determining a readiness score for the corresponding subject and/or one or more predictions for the corresponding subject. Specifically, the genomics assessment represented as the table 400 may be included in the subject data 116 and may be provided to the machine learning models 130, 132, and 134, and/or provided to the intervention model(s) 136.

In some implementations, the machine learning models 130, 132, and/or 134 take into account the genomics of the subject as indicated by genomics assessment represented as the table 400 when calculating a readiness score and/or a risk score for the subject. For example, one or more of the machine learning models 130, 132, and 134 may calculate a higher risk score for the corresponding subject if they have the genes SCN9A and/or FAAH-OUT as these genes indicate an insensitivity to pain. If one or more of these genes are present, the subject would be more likely to injure themselves while completing program tasks or exercises. Accordingly, the machine learning models 130, 132, and/or 134 may determine a higher risk score for the subject than for other, similar performing, subjects who do not have the SCN9A and/or FAAH-OUT genes.

However, depending on the readiness criteria, the machine learning models 130, 132, and/or 134 may calculate a higher readiness score for subject having the genes SCN9A and/or FAAH-OUT. For example, if the readiness criteria requires that the subject must perform the well in a battle, the insensitivity to pain that corresponds with those genes may be viewed as an advantage. Accordingly, the machine learning models 130, 132, and/or 134 may calculate a higher readiness score for the subject than for other, similar performing, subjects who do not have the SCN9A and/or FAAH-OUT genes.

In some implementations, the intervention model(s) 136 shown in FIG. 1C use(s) information in the genomics assessment represented as the table 400 to calculate a prediction (e.g., a percent decrease in time to reach a particular goal or readiness score, or a percent increase in time to reach a particular goal or readiness score), or to generate a recommendation including one or more interventions. For example, if the subject has the LRP5 gene that indicates a higher bone density, the intervention model(s) 136 would not recommend an intervention that includes adding a swimming regimen to the subject's program since the subject has a low buoyancy due to their higher bone density as indicated by the LRP5 gene.

FIG. 5 is a diagram that illustrates an example table 500. The table 500 depicts the results of an example physical or metabolic assessment, e.g., the metabolic assessment 320 shown in FIG. 3. As shown, the table 500 depicts examples of metabolic assessments. The metabolic assessments may include a minimum calculated value, and a maximum calculated value for a particular test. The metabolic assessments may also include one or more targets or goals that the subject should eventually reach or be attempting to reach. The targets may include a first target that corresponds with initial goal that the subject should try to reach (e.g., a goal that is made part of the subject's program and is set for the subject to attempt to reach in four weeks), and a second target that corresponds with a second or final goal that the subject should try to reach (e.g., a goal that is made part of the subject's program and that is set for the subject to attempt to reach by the conclusion of the program in ten weeks). The table 500 also provides equations used in calculating the various values.

Multiple metabolic assessments may be performed on a subject over time. Previous assessments may be compared to the most recent assessment or more recent assessments, and the comparison(s) may be used in determining a readiness score for the subject. As an example, details like VO2Max along with regular exercise targets and comparison to those targets and previous scoring provides a degree of change based on the subject and is an indicator into their tailored human performance training.

There are multiple ways to calculate VO2Max. One such way is to measure the maximum oxygen consumption in liters over a minute and divide it by body weight in kilograms. An alternative to this, and one suggested by the table is to take the maximum heart rate (MHR) and divide it by the resting heart rate (RHR). Collection of this information regularly by a wearable such as a chest strap, ear sensor, wrist sensor, finger sensor, or equipment based sensor such as those found on a treadmill, provide the ability to derive this information over time from a consumer with information captured throughout and prior to any human performance training.

As shown, the metabolic or physical criteria may include deadlifts, power throws, pushups, sprints, pull-ups, and a two-mile run. Each of the metabolic or physical criteria may include a minimum value ("Min X"), e.g., an average value of the lowest 25%, 15%, 10%, or 5% of performers in the corresponding exercise. Each of the metabolic or physical criteria may include a maximum value ("Max X"), e.g., an average value of the highest 25%, 15%, 10%, or 5% of performers in the corresponding exercise.

In some implementations, the minimum values ("Min X") correspond to minimum acceptable levels of performance at the beginning of testing (e.g., at the onset of the subject's program). Whereas, the maximum values ("Max X") correspond to minimum acceptable levels of performance at the end of testing (e.g., at the conclusion of the subject's program).

In some implementations, the minimum values ("Min X") and the maximum values ("Max X") define a range of acceptable performance measures at a point in the testing of the subject. For example, the values may define a range of acceptable performance measures at the beginning of the subject's program, at a point in time after the subject started the program (e.g., two weeks in, four weeks in, three months in, etc.), or at the conclusion of the subject's program.

The metabolic or physical criteria found in the table 500 may corresponding to particular requirements accessed from a database, e.g., by the computer system 110 shown in FIGS. 1A-1C, or set by a coach, counselor, caregiver, care provider, specialist, employer, potential employer, or supervisor. As an example, the metabolic or physical criteria found in the table 500 may correspond to physical requirements set by a Military branch recruiting subjects. These requirements may include, for example, the criteria and/or passing score(s) for the army combat fitness test (ACFT).

In some implementations, the first target ("Target 1") and/or the second target ("Target 2") for each of the metabolic or physical criteria may be preselected.

In some implementations, the first target ("Target 1") and/or the second target ("Target 2") are dynamically selected. For example, with respect to FIGS. 1A-1C, the targets may be selected based on the subject's current readiness score, current risk score, past readiness score(s), and/or trend of readiness scores, e.g., by computer system 110 after referring to a lookup table, or by the computer system 110 after analyzing output of the intervention model(s) 136. As another example, with respect to FIGS. 1A-1C, the targets may be set by a coach, counselor, caregiver, care provider, specialist, employer, potential employer, or supervisor, e.g., based on the subject data 116 after receiving the subject data 116 from the computer system 110, or based on output from the intervention model(s) 136 after receiving the output from the computer system 110. The coach, counselor, caregiver, care provider, specialist, employer, potential employer, or supervisor may set the targets as part of the third-party input 152.

In some implementations, the first target ("Target 1") and/or the second target ("Target 2") are dynamically updated, e.g., based on new assessment data for the corresponding subject (e.g., new calculated readiness score, risk score, performance data, etc.), and/or based on new self-reported data from the corresponding subject or from a coach, counselor, caregiver, care provider, specialist, employer, potential employer, or supervisor (e.g., feedback indicating the subject's pain level, or feelings).

FIG. 6 is a diagram that illustrates an example system 600 for generating precision predictions of readiness. As shown, the system 600 includes deployment dedicated sensors 602 having a data store 604, a personal management device 610, and a server 620. The personal management device 610 may be a computing device such as a smart phone, a laptop computer, a desktop computer, etc. In some implementations, the server 620 is the computer system 110 shown in FIGS. 1A-1C. In some implementations, the deployment dedicated sensors 602 are one or more of the sensing devices 104a-104c shown in FIG. 1A.

On the client deployment side, the personal management device 610 includes a personalized coaching intervention user interface 612, a personalized outline and content 614, and data acquisition module 616. The personalized coaching intervention user interface 612 can be an interface that describes the client side action and activities, measurements, and the modifications to any and all programs. The personalized outline and content 614 can be information that the subject is required to adhere to or complete against in order to stay in compliance with the program and will effectively be measured against. For example, the personalized outline and content 614 may include criteria, goals, challenges, etc. that a subject has been tasked with. This initially begins as a baseline outline and content but is further managed by the personal management device 610 to acquire and reconfigure the experience and training that the subject is required to complete. The personal management device 610 may serve as the manager of the personalized outline and content 614, e.g., by making changes to the subject outline and content 626a located on the server 620.

The data acquisition module 616 may receive collected data from the data store 604 of the deployment dedicated sensors 602. The collected data may include self-reported information, or data from one or more sensors or sensor networks. Sensors may exist within the personal management device 610 or as an external connection or set of connections available to the personal management device 610.

The server 620 includes a management system 622 having a data store 632. The data in the data store 632 is managed by the management system 622 and is specific to the management system 622 and the performance of the management system 622. For example, the data in the data store 632 may be leveraged by the management system 622 to assist the management system 622 in carrying out logical operations.

The server 620 also includes a coaching and community management system 624 having a machine learning algorithm store 634, a machine learning training data store 636, a program data store 638, and data of multiple subjects. As shown, the management system 624 includes a subject outline and content 626a and measurements 628a corresponding to a first subject, and a subject outline and content 626b and measurements 628b corresponding to a second subject. A subject may interact with the management system 624 through a web portal or a mobile application connected to the resources. The management system 624 may allow a subject to access, for example, system settings, a status of subjects, data corresponding to subjects, data corresponding to groups or teams of subjects, classification data, etc. Through the management system 624, a subject may make changes to the program of one or more subjects, and to the algorithms that are required to manage the projected needs of either compliance or readiness for one or more subjects reported by the system 624.

The program data store 638 stores the core information related to the classes in which adherence and readiness are scored. The program itself describes various alternate pathways for varying subject levels based on their readiness. There can be many programs and many outlines and content describing relevant programs. The program data store 638 may store programs that correspond to a type of assessment (e.g., subjects are being evaluated for the same or similar position, undergoing therapy or treatment for the same or similar type of injury, undergoing the same or similar type training, etc.) or to a type of subject (e.g., a consumer, an employee, a potential employee, a trainee, etc.).

The machine learning algorithm store 634 stores one or more machine learning algorithms or models for scoring criteria required to determine readiness and predict future readiness for subjects. For example, the one or more machine learning algorithms or models may be used to determine a readiness score for a particular subject, a risk score for a particular subject, a performance trend for a particular subject, a confidence of a particular subject achieving readiness or another goal, and/or an expected time for the particular subject to achieve readiness or another goal. The machine learning algorithm store 634 may include, for example, the machine learning models 130, 132, and 134, and/or the intervention model(s) 136 shown in FIG. 1C.

The machine learning training store 636 stores information required to provide high accuracy and confidence in the scoring output, e.g., the output of the scoring and prediction module 114 shown in FIG. 1C. The machine learning training store 636 may store past data of one or more subjects, e.g., past sensor data, past self-reported data, past third-party data, past readiness scores, past performance trends, past risk scores, past program completion percentages, or the like. The machine learning training store 636 may store one or more training sets developed from past data of one or more subjects.

Each subject has their own personalized data storage and access that is utilized by the subject across multiple trainings inclusive of programs with outline and content.

The subject outline and content 626a-626b may be unique to a particular subject based on their performance level and supports the management functions on the client side, e.g., may be modified based on custom configurations made to the personalized outline and content 614 on the personal management device 610. A subject's outline may be, for example, their program. This program may be updated overtime, e.g., through one or more interventions recommended by the intervention model(s) 136 shown in FIG. 1C. A subject's content may include, for example, a current or past readiness score, performance trend, or risk score for the subject. A subject's content may include, for example, a prediction such as whether the subject is expected to reach a particular goal (e.g., a set readiness score by a certain time) or when the subject is expected to reach a particular goal. The subject outline and content 626a may be accessed and modified by the personal management device 610, resulting in the personalized outline and content 614. Afterwards, the server 620 may receive the personalized outline and content 614 and replace the subject outline and content 626a with the personalized outline and content 614 or may use the personalized outline and content 614 to update the subject outline and content 626a.

In some implementations, the subject outline and content 626a-626b is not unique to a particular subject, e.g., at least initially. That is, the subject outline and content 626a-626b may start as a copy of a program within the program data store 638. As an example, the subject outline and content 626a-626b can be, or at least start, general to a type of assessment (e.g., subjects are being evaluated for the same or similar position, undergoing therapy or treatment for the same or similar type of injury, undergoing the same or similar type training, etc.) or to a type of subject (e.g., a consumer, an employee, a potential employee, a trainee, etc.). However, the subject outline and content 626a-626b may be updated overtime for the respective subject, e.g., based on respective subject's measurements 628a or 628b, and/or based on the output of one or more of the machine learning models in the store 634.

The measurements 628a-628b are the data recorded for each subject. The measurement 628a and/or the measurement 628b can each be analyzed for a subject or may be analyzed together, e.g., when the corresponding subjects belong to a group or team. Similarly, measurement data can be compared based on the metadata describing the subject's characteristics with other like-minded characterized subjects, for example, in vertical occupations. The measurements 628a-628b may include sensor data collected from the corresponding subjects. The measurements 628a may receive and be updated with data provided by the data acquisition module 616 of the personal management device 610.

In some implementations, the management system 622 provides the measurements 628a-628b to one or more of the machine learning models in the store 634 in order to determine the corresponding subject's readiness score, the corresponding subject's performance trend, the corresponding subject's risk score, and/or one or more predictions involving the corresponding subject such as the likelihood of them reaching a predetermined goal.

In some implementations, the management system 622 uses the output of a machine learning model in the store 634 to update the subject outline and content 626a-626b. For example, the output of a machine learning model in the store 634 may indicate that the corresponding subject is no longer likely to reach a predetermined goal that is part of the subject outline and content 626a and/or 626b. As another example, the output of a machine learning model in the store 634 may indicate one or more interventions that could be automatically (or manually) added to the corresponding subject's program. Accordingly, the management system 622 may automatically select one or more interventions and to update the subject outline and content 626a and/or 626b.

Figure 7:
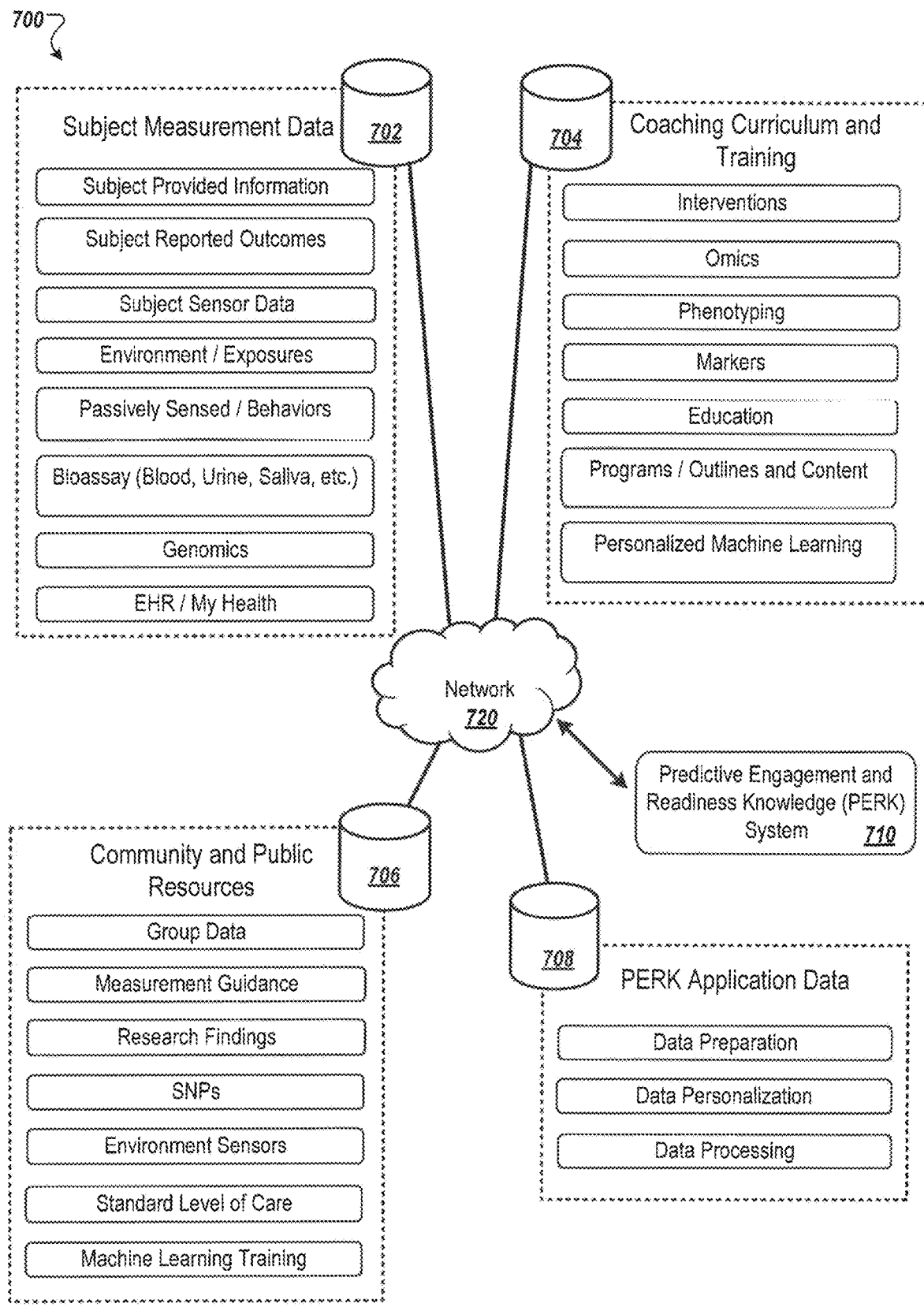
FIG. 7 is a diagram that illustrates the data used by an example system for generating precision predictions of readiness.

FIG. 7 is a diagram that illustrates the data used by an example system 700 for generating precision predictions of readiness. The system 700 includes a subject measurement data store 702, a coaching curriculum and training data store 704, a community and public resources data store 706, an application data store 708, and a system 710. The subject measurement data store 702, coaching curriculum and training data store 704, community and public resources data store 706, application data store 708, and network 720 may form a data network. In some implementations, the system 710 is the computer system 110 shown in FIGS. 1A-1C. In some implementations, the network 720 is the network 160 shown in FIG. 1A.

In evaluating one or more subjects, the system 710 may access data from the subject measurement data store 702, coaching curriculum and training data store 704, community and public resources data store 706, and/or application data store 708.

The system 710 may update data on the subject measurement data store 702, coaching curriculum and training data store 704, community and public resources data store 706, and/or application data store 708, e.g., based on new sensor data, based on new self-reported data, based on new assessments, etc.

In some implementations, the subject measurement data store 702, coaching curriculum and training data store 704, community and public resources data store 706, and/or application data store 708 are part of the system 710, e.g., are found on local storage of the system 710.

The subject measurement data store 702 may include subject provided information, subject reported outcomes, subject sensor data, environment/exposures, passively sensed/behaviors, bioassay (blood, urine, saliva, etc.), genomics, and EHR/My Health. With respect to FIG. 1C, the subject measurement data store 702 may include the self-reported information 150, the electronic health records 154, and/or the genomics data 156. With respect to FIG. 1C, data within the subject measurement data store 702 may be provided to the machine learning models 130, 132, and 134 and/or to the intervention model(s) 136 as the subject data 116. The machine learning models 130, 132, and/or 134 may use all or part of the data within the subject measurement data store 702 that corresponds to a particular subject in determining a readiness score for the subject, determine a risk for the subject, determine a performance trend for the subject, determine whether the subject is likely to reach a predetermined goal, determine a confidence of the subject reaching a predetermined goal, or determine an estimated time for the subject to reach the predetermined goal.

Similarly, the intervention model(s) 136 may use all or part of the data within the subject measurement data store 702 that corresponds to a particular subject in determining one or more interventions for the subject in order to, for example, improve the likelihood of the subject reaching a predetermined goal, improve the readiness score of the subject, lessen the risk of the subject, lessen the estimated time for the subject to reach a predetermined goal, or to account from changed goals for the subject (e.g., if a coach, employer, counselor, or other of the subject updates or modifies the goals for the subject).

The coaching curriculum and training data store 704 may include interventions, omics, phenotyping, markers, education, programs/outlines and content, and personalized machine learning. With respect to FIG. 1C, the coaching curriculum and training data store 704 may include data in the third-party input 152. The interventions in the coaching curriculum and training data store 704 may be those outputted and/or recommended by the intervention model(s) 136 shown in FIG. 1C. The program/outlines and content in the coaching curriculum and training data store 704 may include the initial program assigned to corresponding subjects and/or a current program assigned to corresponding subjects, e.g., one that has been updated over time based on the corresponding subjects' measurements and/or the outputs of one or more machine learning models that receive the corresponding subjects' measurements.

The community and public resources data store 706 may include group data, measurement guidance, research findings, SNPs, environment sensors, standard level of care, and machine learning training. The data stored in the community and public resources data store 706 may include past performance data of subjects, groups of subjects, and/or teams of subjects, e.g., that was used to create one or more training sets. The data in the community and public resources data store 706 may be to generate one or more training sets or may be already organized into one or more training sets. These training set may be used to train one or more machine learning models, e.g., with respect to FIG. 1C, the machine learning models 130, 132, and/or 134, and/or the intervention model(s) 136.

The application data store 708 may assist with data preparation, data personalization, and data processing.

Figure 8:
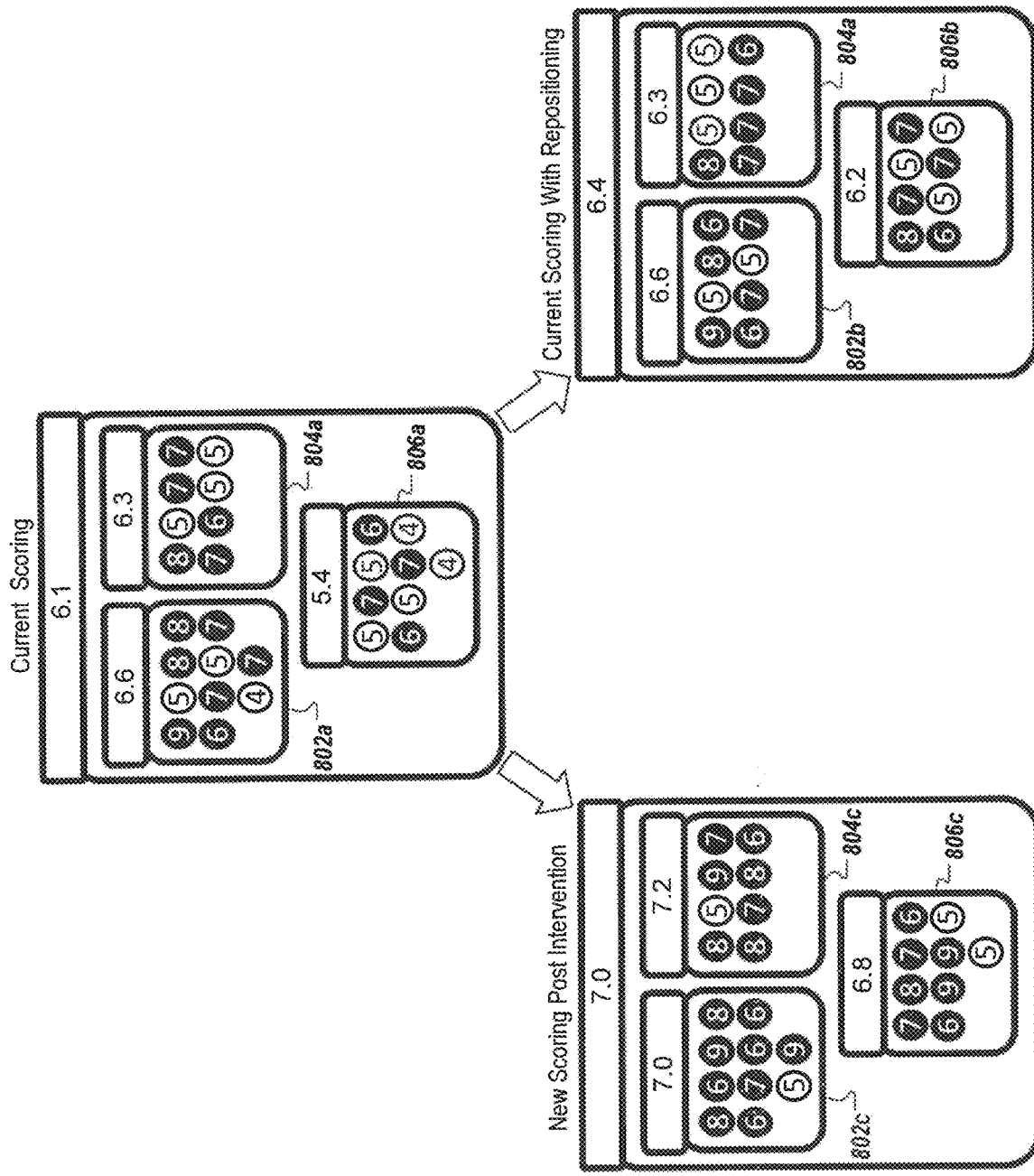
FIG. 8 is a diagram that illustrates an example scoring of subjects.

FIG. 8 is a diagram that illustrates an example scoring of subjects. The scoring may be done by, for example, the computer system 110 shown in FIGS. 1A-1C. The scoring may be done by, for example, the system 710 shown in FIG. 7.

As shown in FIG. 8, the system 100 has determined a readiness score for each of twenty-seven subjects. The system 100 has also divided the twenty-seven subjects into three teams 802*a*, 804*a*, and 806*a*. The first team 802*a* has an average readiness score of 6.6. The second team 804*a* has an average readiness score of 6.3. The third team 806*a* has an average readiness score of 5.4. As a whole, the group of twenty-seven subjects has an average readiness score of 6.1, e.g., the average readiness among the three teams 802*a*, 804*a*, and 806*a*.

In some implementations, the system 100 may improve the overall group readiness and/or the readiness of the each of the teams 802*a*, 804*a*, and 806*a* by repositioning subjects. Repositioning the subjects may include the system 100 removing one or more subjects from the group (e.g., those having a readiness score below a particular threshold), or adding one or more subjects to the group (e.g., those having a readiness score at or above a particular threshold). Repositioning the subjects may additionally or alternatively include the system 100 moving one or more subjects to a different team within the group. For example, as shown, the system 100 has removed the lowest scoring subjects, those with a readiness score of 4/10, from the group. In addition, the system 100 has moved a subject having a score of 6/10 from the third team 806*a* to the first team 802*a*, and has moved a subject having a score of 8/10 from the first team 802*a* to the third team 806*a*. This results in the average readiness score of the third team 806*b* increasing to 6.2, and the overall readiness score for the group increasing to 6.4.

In some implementations, the system 100 determines which subjects to reposition is based on the characteristics of the subject and/or the evaluation being performed. For example, the system 100 determines which subjects to reposition based on an occupation or training criteria, and whether to expel or provide a degree of negative punishment.

In some implementations, the system 100 requires new scores of the original twenty-seven subjects after they have completed respective interventions. The new scores indicate that, on average, the subjects increased their readiness scores. As shown, the average readiness score for the first team 802*c* increased to 7.0, the average readiness score of the second team 804*c* increased to 7.2, the average readiness score of the third team 806*c* increased to 6.8, and the overall readiness score for the group increased to 7.0.

Through repositioning and/or the obtaining of new readiness scores, the system 100 can increase the average readiness scores of teams and of a group. In addition, by repositioning subjects, the system 100 can form teams that are likely to be better balanced, e.g., that perform similarly to one another, or are at least expected to perform similarly to one another.

FIGS. 9A-9E are diagrams that illustrate example interfaces 900*a*-900*e* showing assessment analytics and results. The interfaces 900*a*-900*e* may be displayed on a computing device that received data from the computer system 110. The interfaces 900*a*-900*e* may be displayed a device of a user assigned or entrusted with monitoring or assisting subjects to achieve and maintain readiness, such as on the third-party device 208 of the third party 206 (e.g., a coach, caregiver, employer, potential employer, supervisor, and the like). In some implementations, some or all of the interfaces 900*a*-900*e* can be provided for display by devices of subjects whose progress is being monitored.

FIG. 9A depicts a user interface 900*a* that provides a list view of subjects being assessed and analytical data corresponding to those subjects, such as program completion percentage, pain levels, program intensities, program date, and readiness scores for each of the subjects. The subjects shown in the user interface 900*a* may subjects who are currently being evaluated. The interface 900*a* may be generated by the computer system 110. The interface 900*a* may be populated with data acquired from the computer system 110. The interface 900*a* may be provided for display by a device associated with a third party 206 (e.g., a coach, caregiver, employer, potential employer, supervisor, doctor, researcher, and the like) or other user.

The interface 900*a* includes a display area 902 that includes a subject section 904*a*, a first filter section 906, and a second filter section 908. The subject section 904*a* includes a list of all subjects and corresponding analytical data, such as program completion percentage, pain levels, program intensities, program date, and readiness scores for each of the subjects. The interface provides functionality so a user may use a search box in the subject section 904*a* to search through the subjects by name or ID. The interface provides functionality so a user may use the first filter section 906 to filter subjects presented in the subject section 904*a* by study levels. The interface provides functionality so a user may use the second filter section 908 to filter subjects by their activity/inactivity/adherence with respect to the program. For example, inactivity may be defined by a subject failing to complete any goals or challenges for a given amount of time, e.g., two days.

The user interface 900*a* also presents an expanded subject section 904*b*. The expanded subject section 904*b* may provide the same information as the subject section 904*a*. The expanded subject section 904*b* is larger than the subject section 904*a*, which allows the third-party 206 or another user to process the information presented in the expanded subject section 904*b* more efficiently than information presented in the subject section 904*a*.

The user interface 900*a* also presents additional information such as a program day and location ("Site"). The completion percentage for each of the subjects may indicate (i) how far along the subject is in the program, and/or (ii) if the subject is complying. A low percentage may indicate that the subject is failing to comply with the program when compared with the number of days that the subject has bene in the program, which could result in a lower readiness score. The level of pain and intensity may also affect how a readiness score for a subject is calculated. For example, the level of pain and intensity may indicate that the subject recovers slowly, recovers quickly, suffers from chronic pain, or the like. These determinations may, in turn, affect a readiness score for the subject, an expected time until readiness, or the like.

Figure 9B:
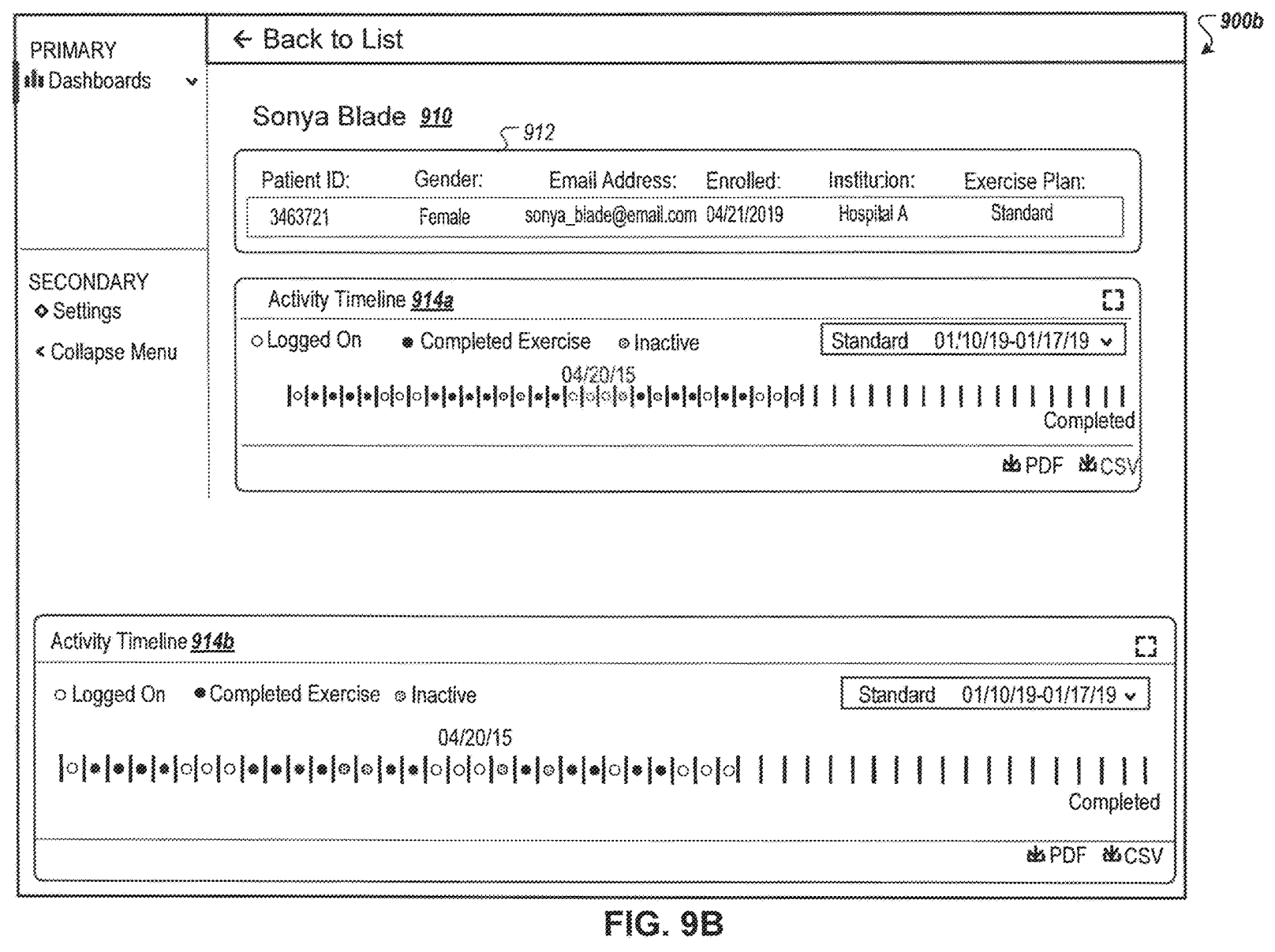

FIG. 9B depicts a user interface 900*b* showing assessment analytical data for a particular subject 910. This analytical data includes a time series that shows the program trends for the subject 910. The interface 900*b* may be generated by the computer system 110. The interface 900*b* may be populated with data acquired from the computer system 110. The interface 900*b* may be provided for display by a device associated with the subject 910, a third party 206 (e.g., a coach, caregiver, employer, potential employer, supervisor, doctor, researcher, and the like) associated with the subject 910, or another user.

The interface 900*b* includes a subject information section 912. The subject information section 912 includes information corresponding to the subject 910, such as an ID, a gender, contact information, a program enrollment date, and a type of training plan.

The interface 900*b* includes timeline sections 914*a* and 914*b*. The timeline sections 914*a* and 914*b* each present a time series for the subject 910. The time series for the subject 910 indicates the activity of the subject 910 over the course of the program/assessment. For example, the time series may show the number of days that the subject 910 completed exercises, the number of days that the subject 910 logged on but failed to complete their exercises, and the number of days that the subject 910 was inactive over the course of the program. This information may be used by the computer system 110 to determine, for example, that the subject 910 has completed a high percentage of their exercises, has completed a low percentage of their exercises, has an improving exercise completion percentage, has a worsening exercise completion percentage, or the like. The computer system 110 may then use these determinations in generating predictions such as a readiness score for the subject 910, a time until the subject is ready, or the like. The interface 900*b* may be presented to a coach, caregiver, or another user as a virtual check-in of the subject 910.

The interface 900*b* may be presented to a user when the user selects a particular subject from the list of subjects in the interface 900*a* shown in FIG. 9A. The interface 900*b* may be presented to the third-party 206 when the third-party 206 selects a particular subject from the list of subjects in the interface 900*a* shown in FIG. 9A.

Figure 9C:
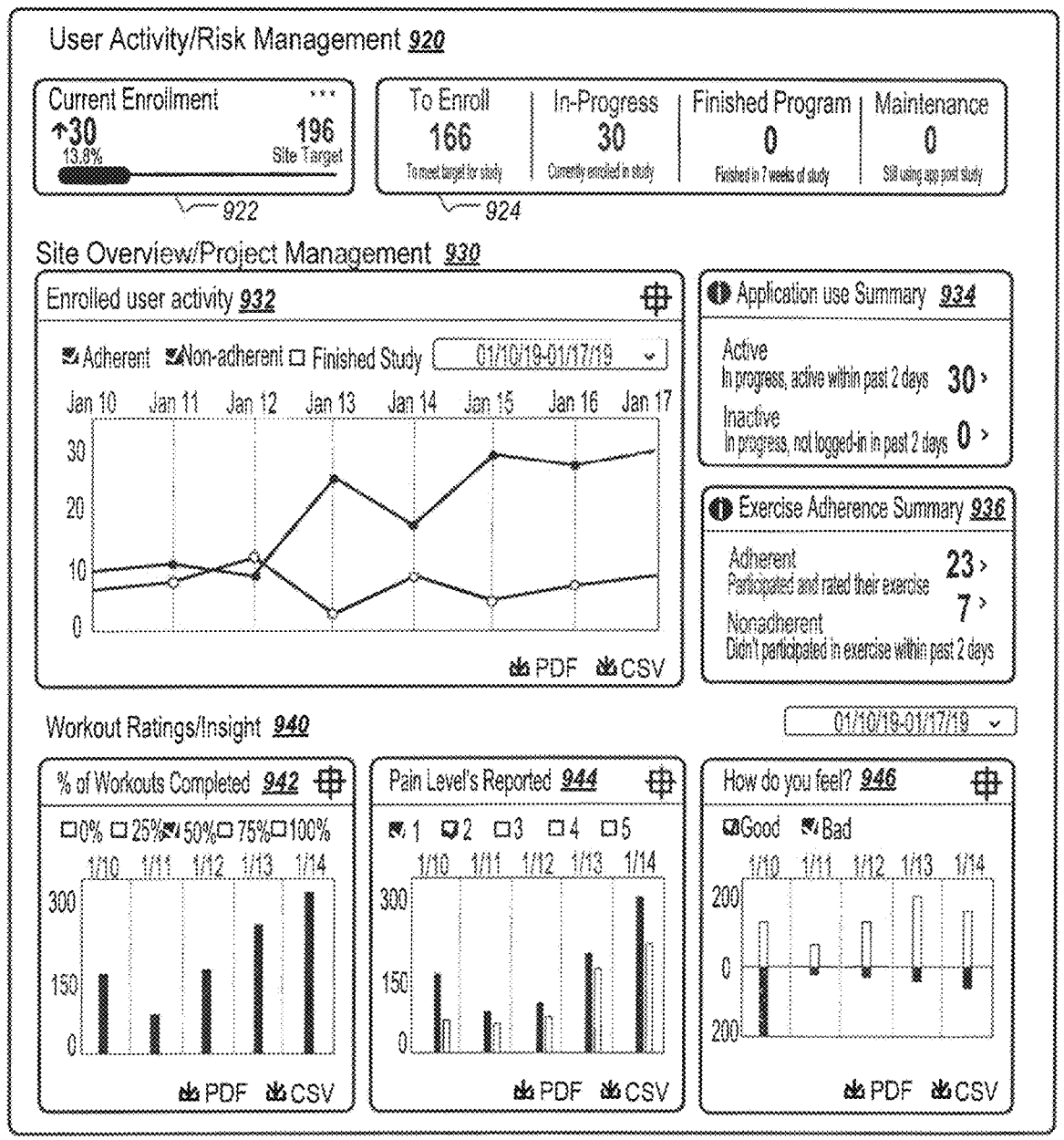

FIG. 9C depicts a user interface 900*c* of subject activity and risk management. The user interface 900*c* may allow for the display and comparison various subjects and their respective ratings against risk, such as incomplete trainings, pain, and aversion. As shown, the user interface 900*c* includes a number of graphical representations of the subjects' progress in the program. These graphical representations show, for example, the trends of the subjects' activity, workout or challenge completion percentages, pain levels, and feelings. The interface 900*c* may be generated by the computer system 110. The interface 900*c* may be populated with data acquired from the computer system 110. The interface 900*c* may be provided for display by a device associated with a third party 206 (e.g., a coach, caregiver, employer, potential employer, supervisor, doctor, researcher, and the like) or another user associated with the group of subjects.

The interface 900*c* includes a number of display areas: a first display area 920 that presents user activity and/or risk management data, a second display area 930 that presents site overview and/or project management data, and third display area 940 that presents workout ratings and/or insight.

The display area 920 includes a current enrollment section 922 showing the current number of subjects enrolled in the program and the target number of subjects. Here, the number of subjects enrolled is thirty and the target number of subjects is 196. The display area 820 also includes second section 924 that provides additional program information such as the number of additional subjects needed to meet subject target, the number of subjects currently enrolled, the number of subjects who have successfully completed the program, and the number of subjects in maintenance, e.g., the number of subjects continuing to use the program application after completing the program.

The display area 930 includes an enrolled user activity section 932 showing a graph depicting the activity of subjects. The graph may display an indication of the number of subjects who are adherent, who are non-adherent, and/or who have completed the program over a given time period. For example, the graph shows the number of subjects that were adherent, e.g., completed their challenges, and non-adherent, e.g., failed to complete their challenges, for each day between Jan. 10, 2019 and Jan. 17, 2019. The display area 930 also includes a first summary section 934 that indicates the number of subjects that are active and inactive. The display area 930 further includes a second summary section 936 that indicates the number of subjects that are adherent and non-adherent.

The display area 940 includes a training section 942 showing a graph that indicates the percentage of workouts that the subjects completed over a given period of time. The display area 940 also includes a pain level section 944 showing a graph that indicates the pain level's reported by the subjects over a period of time. The display area 940 further includes a feeling section 946 showing a graph that indicates how the feelings reported by the subjects over a period of time.

The data and trends depicted in the user interface 900*c* may be used by the system 100 (e.g., by the prediction and scoring module 114 of the computer system 110) in calculating readiness scores for the subjects or an average score for the group or team of subjects, performance trends for the subjects or an overall performance trend for the group or team of subjects, a confidence that the subjects will likely achieve readiness or a confidence if the group or team of subjects will likely achieve readiness, a time when each of the subjects will likely achieve readiness or a time when the group or team of subjects will likely achieve readiness, or the like.

The information displayed in the user interface 900*c* can be collected from the self-reported information 150, from the sensor data 106, and/or from the third-party input 152 shown in FIG. 1C. In some implementations, the information displayed in the user interface 900*c* is only collected from the self-reported information 150.

The information displayed in the user interface 900*c* can be generated by the data aggregation module 112 shown in FIGS. 1A-1C. The data aggregation module 112 may, for example, organize the self-reported information 150, the sensor data 106, the third-party input, and/or other data by the date (e.g., day as shown), by the group of subjects, by the team of subjects, and/or by a particular location of subjects.

The information displayed in the user interface 900*c* may be provided to the scoring and prediction module 114 shown in FIGS. 1A-1C. All or part of the information displayed in the user interface 900*c* may be part of the subject data 116.

Figure 9D:
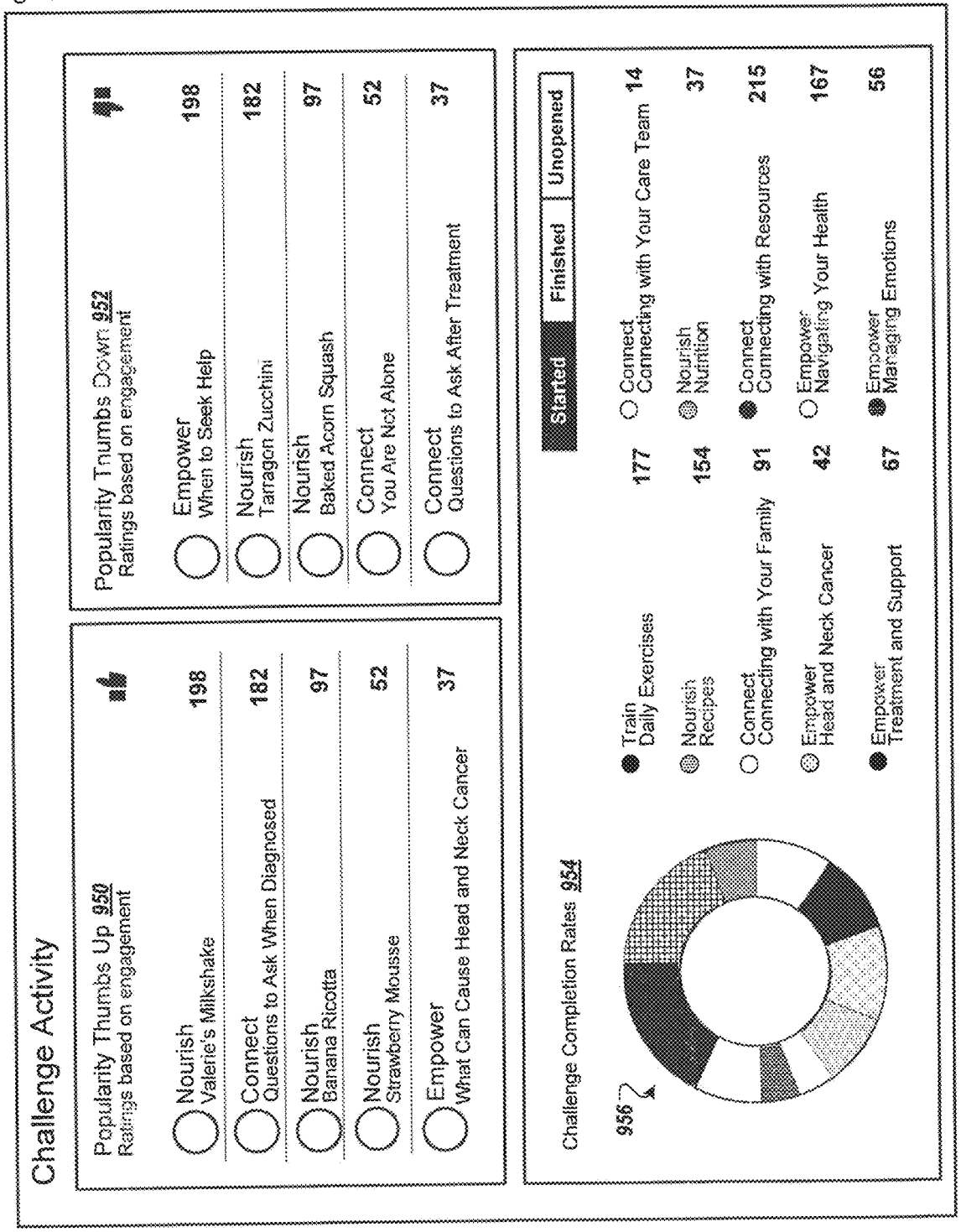

FIG. 9D depicts a user interface 900*d* of challenges or goals, and corresponding analytics data. The interface 900*d* may be generated by the computer system 110. The interface 900*d* may be populated with data acquired from the computer system 110. The interface 900*d* may be provided for display by a device associated with a third party 206 (e.g., a coach, caregiver, employer, potential employer, supervisor, doctor, researcher, and the like) or another user associated with the group of subjects whose data is reflected in the interface.

The user interface 900d includes a first display area 950 that provides the most popular or highest rated challenges by subjects. The user interface 900d also includes a second display area 952 that provides the least popular or lowest rated challenges. The user interface 900d further includes a third display area 954 that provides indications of challenge completion rates. In the display area 954, a user can select whether to view challenges that were started but not yet completed, challenges that were completed, or challenges that have yet to be opened. The display area 954 may also provide an indication of how frequent the selected activity is with the various challenges, and how the frequency of the activity of the various challenges compare to one another. For example, the display area 954 provides that, in the "Train" category, the item "Daily Exercises" have been started one hundred and seventy-seven times and is, therefore, one or more frequently started challenges as indicated by the graph 956.

The user interface 900d may display various analytics of intervention challenges or goals. The analytics may indicate what challenges subjects like, what challenges subjects dislike, what challenges subjects are likely to perform, and/or what challenges subjects are unlikely to perform. The analytics may be based on feedback from subjects, e.g., a binary indicator such as a thumbs up or thumb down. The analytics may also be based on subjects' activity, such as an indication that many subjects start but don't complete a particular challenge, never open or start a particular challenge, always start a particular challenge, always complete a particular challenge if started, or the like. For example, the positive popularity feedback in the display area 950, the negative popularity feedback in the display area 952, and the challenge completion rates in the display area 954 may be provided to the scoring and prediction module 114 shown in FIGS. 1A-1B to suggest challenges for a given subject, to add challenges for a given subject, to remove challenges for a given subject, to remove a challenge for all subjects (e.g., the lowest rated or least popular challenge(s)), to add a challenge for all subjects (e.g., the highest rated or most popular challenge(s)), or the like. In making these predications, the scoring and prediction module 114 may use one or more static algorithms, or may use one or more machine learning models such as the machine learning models 130, 132, and 134 shown in FIG. 1C.

The computer system 110 may use the challenge completion percentages or rates from multiple subjects in generating a training set to train one or more machine learning models. For example, the computer system 110 shown in FIGS. 1A-1C may use the challenge completion percentages or rates shown in the user interface 900d in generating training sets for the machine learning models 130, 132, and 134, and/or the one or more intervention model(s) 136 shown in FIG. 1C.

Figure 9E:
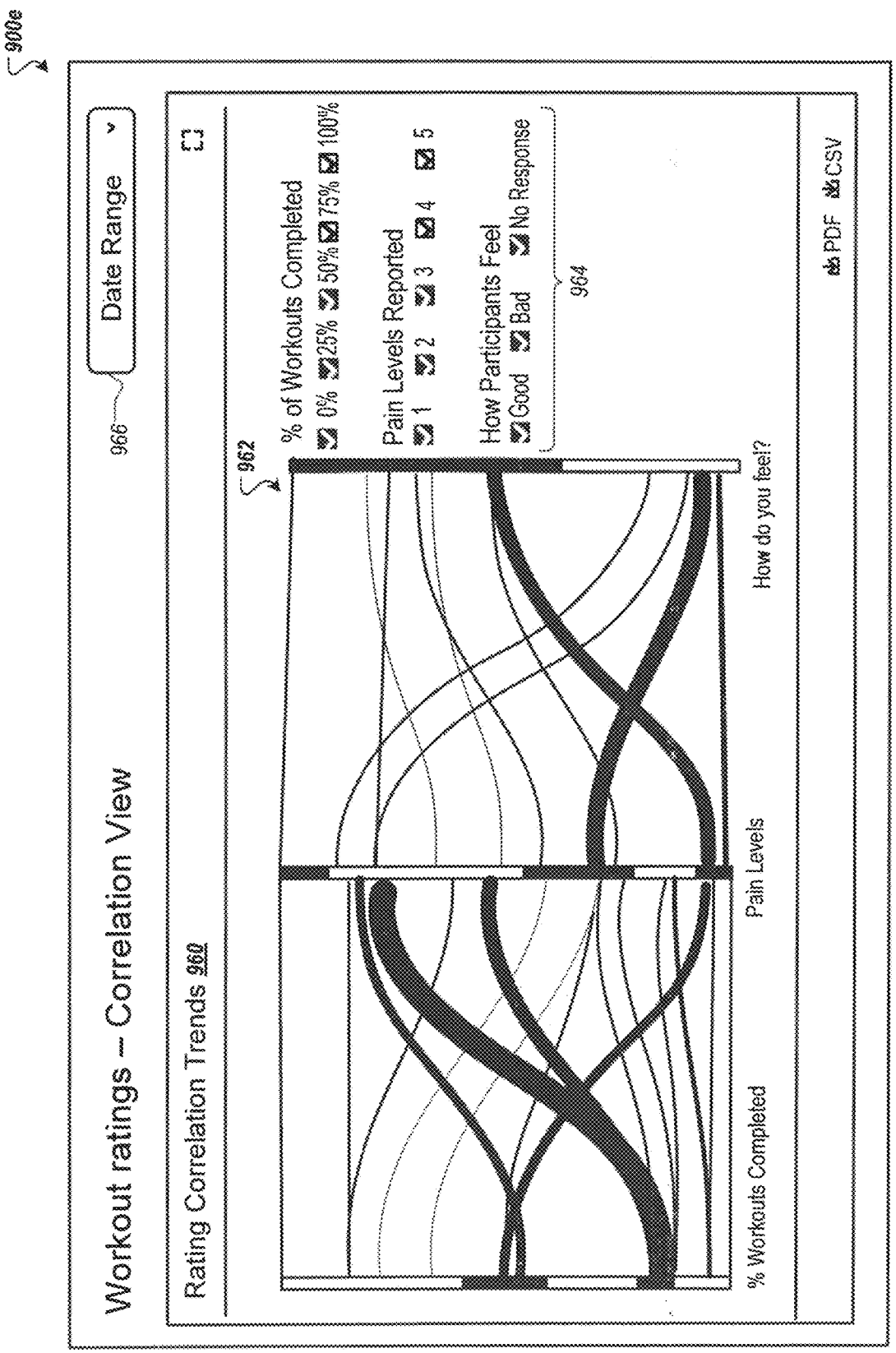

FIG. 9E depicts a user interface 900e of correlation trends among multiple subjects. The user interface 900e may display correlating outcomes and vulnerabilities across all subjects, a group of subjects, or a team of subjects in a display area 960 as a graph 962. The user interface 900e correlates the subjects' workout completion percentage with their pain levels and with their feelings (e.g., good, bad, or no response). This information may be used by the computer system 110 to train one or more machine learning models. This information may indicate trends that can be used by the computer system 110 to predict, for example, how a given subject will feel or the pain levels they will experience if they complete 75% of their assigned workouts. The interface 900e may be generated by the computer system 110. The interface 900e may be populated with data acquired from the computer system 110. The interface 900e may be provided for display by a device associated with a third party 206 (e.g., a coach, caregiver, employer, potential employer, supervisor, doctor, researcher, and the like) or another user associated with the group of subjects.

The interface provides functionality so a user may filter the data presented in the graph 962 using the filter controls 964. A user may choose to only see the trends for a given date range by selecting a date range from the dropdown menu 966.

The user interface 900e may be generated based on past data of multiple subjects or the current data of a group of subjects. The correlation trends depicted in the user interface 900e may be used by, for example, a static algorithm or by the machine learning models 130, 132, and/or 134 shown in FIG. 1C in determining a performance trend of a corresponding subject or a risk of a corresponding subject. For example, the correlation trends depicted may indicate that subjects who have completed a lower percentage of workouts should receive a higher risk score since it indicates that those who complete a lower percentage of workouts are more likely to experience higher pain levels which, in turn, causes them to feel bad. Other correlations would likely indicate that those subjects who experience higher pain levels and/or generally feel bad are less likely to complete the program, less likely to improve their performance, less likely to reach their goals, etc.

While the example of FIG. 9E shows a specific example of relating workout completion percentage, pain levels, and participant subjective responses, the same type of chart can be used to show correlations between any of various parameters or factors measured by the system. This can also be used to show correlations or relative paths of different activities or subject characteristics to different readiness scores or readiness timing (e.g., ready within 1 month, ready within 2 months, etc.).

Figure 10:
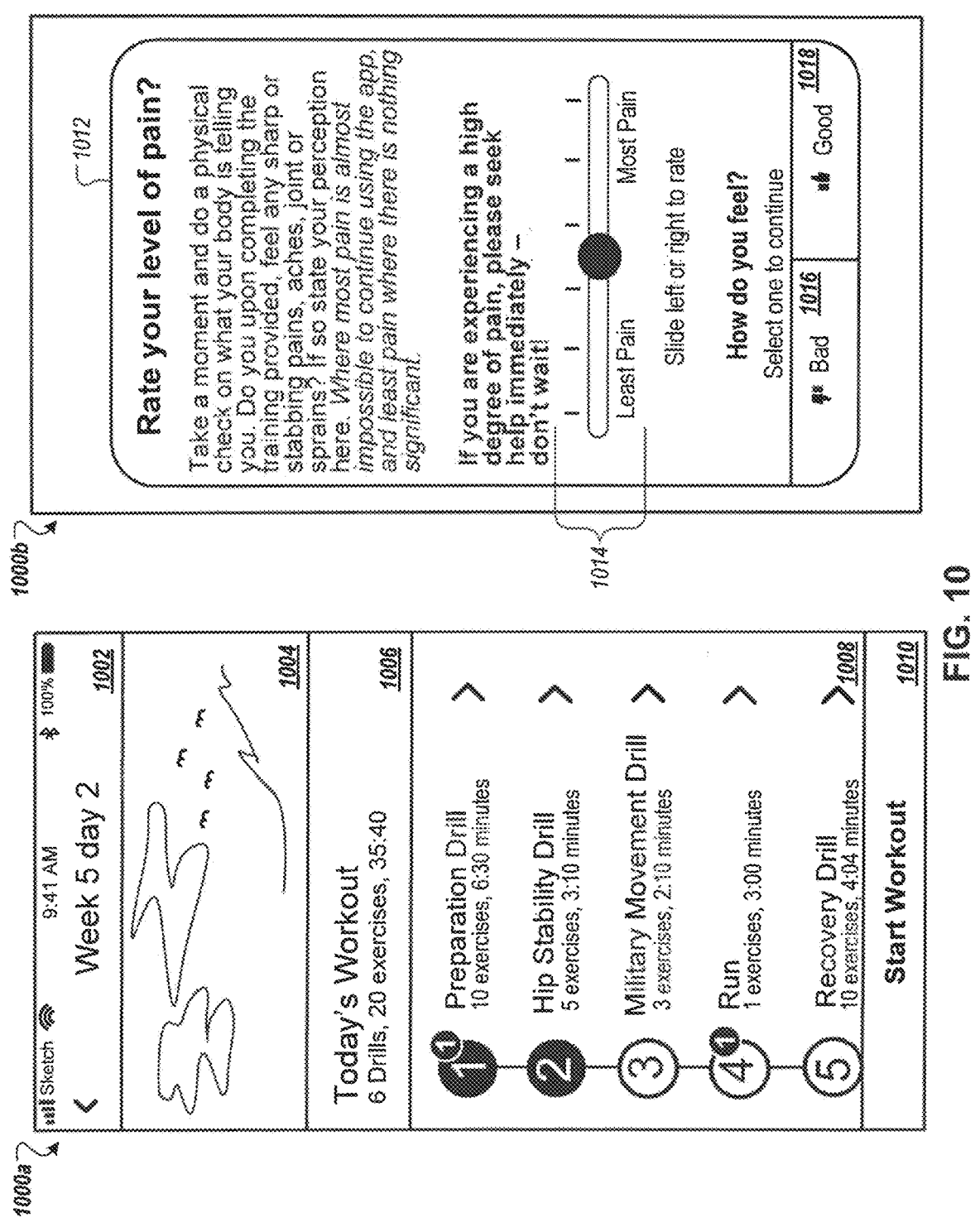

FIG. 10 is a diagram that illustrates example interfaces 1000a-1000b. The interfaces 1000a-1000b may be presented to the subject 202 through a client application (e.g., a mobile application) on the client device 204 during an assessment of the subject 202. The interfaces 1000a-1000b may be generated by the computer system 110. The interfaces 1000a-1000b may be populated with data acquired from the computer system 110.

In some implementations, the interfaces 1000a-1000b, or interfaces substantially similar to interfaces 1000a-1000b, are presented to the third-party 206 (e.g., a coach, caregiver, employer, potential employer, supervisor, doctor, researcher or the like) through an application on the third-party device 208. These interfaces may be generated by the computer system 110.

The interface 1000a includes four display areas: an assessment duration/date area 1002, a current weather area 1004, a training summary area 1006, and a detailed training area 1008. The interface 1000a also includes an interface element 1010. The assessment duration/date area 1002 includes an indication of the subject 202's current date of assessment, e.g., an indication of how long the subject 202 has been assessed for. Here, the subject 202 has just completed their fifth week of assessment. The current weather area 1004 may provide an indication of the current weather, such as an image that corresponds with the weather (e.g., clouds and sun if partially cloudy, sun if sunny, clouds if overcast, clouds and rain if raining, etc.) and/or text that corresponds to the current temperature. The computer system 110 may pull weather data from an external server and use this in generating the current weather area 1004.

The interface 1000a displays a tailored training program for the subject 202 in the display areas 1006 and 1008. The training summary area 1006 includes a summary of the subject 202's tailored training program for the current assessment date provided in the area 1002. As shown, the summary of the subject 202's tailored training program provides an indication of the number of drills (e.g., challenges or goals) that the subject 202 is expected to complete on this day, the total number of exercises in those drills, and an estimated time for the subject 202 to complete all of the drills/exercises. The drills and their exercises may be selected for the subject 202 by the computer system 110. The computer system 110 may calculate an estimated time for the subject 202 to complete the drills/exercises based on the subject 202's past performances and/or based on the performances of others.

The detailed training area 1008 provides a more detailed view of the subject 202's tailored training program for the current assessment date provided in the area 1002. The detailed training area 1008 may provide information about each of the drills, such as a name of the drill, the number of exercises in the drill, an expected time for the subject 202 to complete the drill, a recommend order for the subject 202 to perform the drills in, and whether the subject 202 has completed a given drill. For example, a drill may be marked as completed by an indicator next to the drill changing color (from white to black). A subject 202 may be presented more detailed information about a given drill by selecting the drill. When the subject 202 selects an individual drill, they may be presented more detailed information on each of the exercises within the drill, such as a name of the exercise and an expected time for the subject 202 to complete the exercise.

As shown in the detailed training area 1008, five of the six drills (e.g., challenges or goals) of the subject 202's tailored training program are provided. These challenges or goals may be for a particular period of time, e.g., for the specific assessment date (e.g., day 2 of week 5), for the current week, for the current month, etc. The subject 202 may select a challenge or goal (e.g., through a touch input) to see additional details for the selected challenge or goal.

The subject 202 may select interface element 1010 (e.g., through a touch input) which can initiate the start of the first challenge or goal, e.g., the "Preparation Drill" consisting of ten exercises, or the start of the next incomplete challenge or goal, e.g., the "Military Movement Drill" consisting of three exercises.

The interface 1000b allows for the subject 202 to enter and submit self-reported responses. The interface 1000b includes a display area 1012 where the subject 202 can provide responses for indicating a pain level experienced by the subject 202 after completing a set of challenges or goals (or completing a given challenge or goal), e.g., the six drills for week five day 2 of the subject 202 assessment. The display area 1012 includes a slider 1014 that the subject 202 can operate by sliding to the left to indicate less pain experience or by sliding to the right to indicate greater pain experienced. The operation of the slider 1014 is one type of response that the subject 202 can provide. The responses may include a binary indication of how the subject 202 feels, e.g., good or bad. As shown, the interface 1000b also includes interface elements 1016 and 1018. The interface element 1016 allows the subject 202 to provide a binary response that they feel bad. The interface element 1018 allows the subject 202 to provide a binary response that they feel good. The subject 202 may be able to provide responses both through the slider 1014 and either the interface element 1016 or the interface element 1018. The application may prompt the subject 202 with the interface 1000b after the subject 202 attempts or successfully completes a challenge or goal, after the subject 202 has attempted or successfully completed all challenges or goals for a given assessment date, or after an assessment date has passed (e.g., responses may be requested from the subject 202 the next day). The responses may be provided from the client device 204 to the computer system 110. The computer system 110 may use the responses to modify the tailored training program for the subject 202.

FIG. 11 is a diagram that illustrates example interfaces 1100a-1100b. The interfaces 1100a-1100b may be presented to the subject 202 through a client application (e.g., a mobile application) on the client device 204 during an assessment of the subject 202. The interfaces 1100a-1100b may be generated by the computer system 110. The interfaces 1100a-1100b may be populated with data acquired from the computer system 110. The assessment may occur based on a set schedule, e.g. may occur at a time set by the third-party 206 (e.g., a coach, caregiver, employer, potential employer, supervisor, or the like), may occur every week (e.g., on the last day of the week), may occur every month (e.g., on the last day of the month), etc.

In some implementations, the interfaces 1100a-1100b, or interfaces substantially similar to interfaces 1100a-1100b, are presented to the third-party 206 (e.g., a coach, caregiver, employer, potential employer, supervisor, doctor, researcher, or the like) through an application on the third-party device 208. These interfaces may be generated by the computer system 110.

The interface 1100a displays prior assessment data for the subject 202 and current metrics for the subject 202. The interface 1100a includes two display areas: an assessment duration/date area 1102, and an assessment area 1104. The assessment duration/date area 1102 includes an indication of the subject 202's current date of assessment, e.g., an indication of how long the subject 202 has been assessed. Here, the subject 202 has just completed their fifth week of assessment. The assessment area 1104 includes a prior assessment data section 1106, a current metrics section 1108, and a section that includes an interface element 1122. The prior assessment data may include, for examples, predictions such as if they are likely to reach a particular readiness score and, if so, when they are expected to reach that readiness score. The prior assessment data may include prior readiness scores, performance trend(s), prior risk scores, prior exercise completion percentage, prior average pain levels, prior average feelings, etc.

The prior assessment data section 1106 includes a first predication 1110 and a second prediction 1112 that were generated using, for example, the prior assessment data shown in a table 1114. The predictions can be generated by the computer system 110. As shown, the table 1114 includes data on the corresponding subject 202's first four weeks of assessment.

The current metrics section 1108 includes multiple metrics 1116-1120 corresponding to the subject 202 that were calculated using data collected over the current assessment period. The metrics 1116-1120 may help to show the subject 202 and/or the third-party 206 areas where the subject 202 is improving or areas where the subject 202 still needs to improve, e.g., when compared with the data in the table 1114. Here, the metric 1116 is the exercise completion percentage for the subject 202 over the current assessment period. The metric 1118 is the average pain level for the subject 202 over the current assessment period. The metric 1120 is the recent average feeling for the subject 202 over the current assessment period. The metrics 1116-1120 may be calculated, for example, by the computer system 110 shown in FIGS. 1A-1B. These metrics may be calculated by the computer system 110 based on the self-reported information 150 and/or the sensor data 106.

In the example of FIG. 11, the assessment period is one week. However, other assessment periods are possible. For example, an assessment may be performed every day, every two weeks, every month, or the like. In addition, there may be multiple assessments. For example, there may be a daily assessment that is, for example, provided to the subject 202 through the client device 204, and a weekly assessment that is provided to the subject 202 through the client device 204 and to the third-party 206 through the third-party device 208.

The computer system 110 shown in FIGS. 1A-1C may use this prior assessment data in determining a new readiness score for the subject 202, a new risk score for the subject 202, an updated performance trend for the subject 202, and/or one or more predictions (e.g., whether the subject 202 is still likely to reach the readiness score goal, and, if so, what the updated expected time is for the subject 202 to reach the readiness score goal). The computer system 110 may be used to generate the predictions 1110 and 1112. The computer system 110 may be used to generate the table 1114. The computer system 110 may be used to calculate the metrics 1116-1120.

The interface 1100a also includes the interface element 1122. When the subject 202 or the third-party 206 selects the interface element 1122, assessment results may be generated for the subject 202 and the subject 202/third-party 206 may be presented the interface 1100b. The assessment results may be those for the current assessment period, e.g., for week five. The assessment results may be generated by the computer system 110.

The interface 1100b displays information to the subject 202 based on the new assessment. The interface 1100b displays a current readiness score for the subject 202, a current risk score for the subject 202, and predications for the subject 202 in a summary section 1124. For example, as shown, the interface 1100b displays a prediction that the subject 202 is likely to reach the goal of obtaining a readiness score of 8/10 earlier than previously expected, at the beginning of week 8 of the subject 202's program. With respect to FIG. 1A, the readiness score, risk score, and predications may be determined by the scoring and prediction module 114, e.g., based on the outputs of the machine learning models 130, 132, and/or 134 shown in FIG. 1C. With respect to FIG. 1C, the readiness score, risk score, and predications may be determined by the machine learning models 130, 132, and/or 134.

The interface 1100b also displays multiple options 1126 and 1128 that the subject 202 or the third-party 206 may select. A selection of either of the options can result in the subject 202's program being changed to reflect the changes indicated in the respective option 1126 or 1128. In some implementations, the options 1126 and 1128 are not provided to the subject 202 for selection. For example, the options 1126 and 1128 may be presented to the third-party 206 such as a coach or caregiver of the subject 202. The coach or caregiver may then select one of the options 1126 or 1128, or may choose not to select an option. With respect to FIG. 1C, the options 1126 and 1128 may be generated by the interventions model(s) 136 as recommendations, e.g. based on a determination that they would have the effect of getting the subject 202 to their readiness score goal earlier than currently expected. In addition, the intervention model(s) 136 may calculate an expected effect if either of the options 1126 or 1128 are chosen. For example, as shown, the intervention model(s) 136 may have calculated that if option 1126 is selected, the subject 202 is expected to reach their readiness score goal five days earlier.

Figure 12:
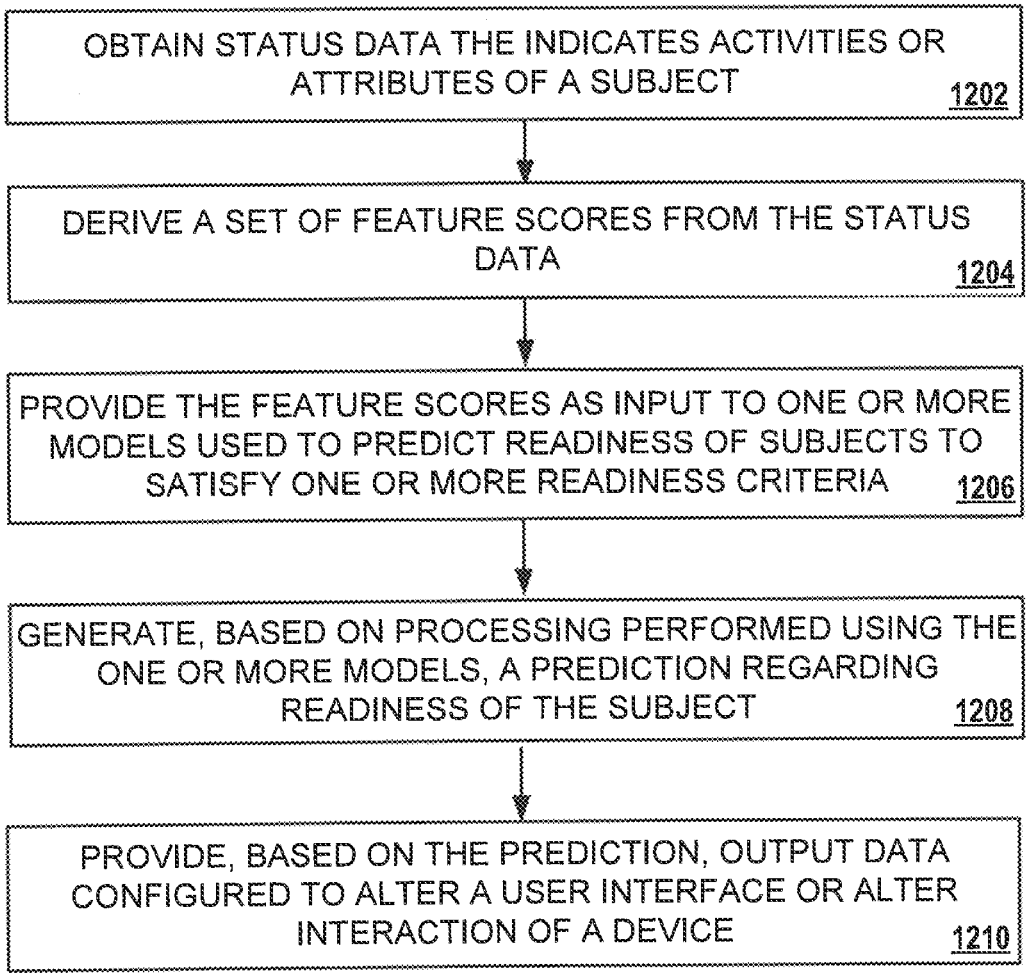
FIG. 12 is a flowchart that illustrates an example process for predicting readiness.

FIG. 12 is a flowchart that illustrates an example process 1200 for predicting readiness. The process 1200 can be performed by one or more computers, such as using the computer system 110 described above. Steps of the process 1200 can be performed by one or more servers, one or more client devices, or by a combination thereof and/or other devices.

The process 1200 includes accessing a database to obtain status data that indicates activities or attributes of a subject (1202). The status data can include data provided by an electronic device to the one or more computers over a communication network. As discussed above, a diverse set of subjects can be evaluated and assessed using the techniques herein, such as a device, a system, a model, a hardware component, a research study, a software component, an organization, a team, an individual (e.g., a person), a combination of one or more people and equipment, and so on.

The attributes indicated in the database can include any of various types of information that describe or characterize the state of the subject, and the attributes can be derived from many different sources. The attributes can describe, for example, physical characteristics (e.g., size, dimensions, weight, age, maintenance status, health status, physiological measures, genomics data, proteomics data, etc.) or functional characteristics (e.g., capacity, speed, efficiency, reliability, etc.). The attributes can be self-reported by a subject, provided by a third party (e.g., an administrator, a coach, a technician, a doctor, a researcher, a supervisor, etc.), provided by one or more devices (e.g., devices used in training, tools, networking equipment, maintenance devices, medical equipment, phones, wearable devices, devices that interact with the subject or monitor the subject, etc.).

As a few examples, when the subject is a device, attributes can be indicators of the structure and/or functional ability of the device. For example, attributes can indicate various measures of status or performance capability, such as storage capacity, processor usage, power consumption, memory usage, network bandwidth usage, network latency, response latency, throughput, error rates, and so on. Attributes can also refer to specifications or ratings of the device and its components; the make, model, or type of device; the number and types of components included in the device; hardware and/or software configuration of the device; configuration settings; and so on.

For a subject that is a person, attributes can include vital signs or baseline indicators of health status (e.g., heart rate, respiratory rate, blood pressure, oxygen saturation, respiratory rate, respiratory effort, capillary refill time, temperature, etc.). Other attributes include height, weight, strength measurements, endurance measurements, blood chemistry measurements, genomics data (e.g., data indicating whether the subject has or lacks certain genes or certain classes of genes, indications of which form of a gene is present, etc.), proteomics data (e.g., data indicating the identification, localization, and functional characteristics of proteins of a subject). Subject attributes can include whether a person has been diagnosed with a disease or other condition (e.g., cancer, diabetes, heart disease, chronic obstructive pulmonary disease (COPD), etc.), the current status of the disease (e.g., disease stage or classification, effects or limitations due to the condition, a severity or level of progression of the disease), whether the person has received treatment and what type of treatment, and so on. Attributes may indicate the structure and/or functional capability of any structures or systems of the body. Subject attributes can include mental and psychological indicators such as anxiety levels, pain levels, scores for various personality traits, and so on.

The database can include data generated for the subject over a period of time, the status data comprising information about activities or attributes of the subject at multiple points in time. The computer system 110 track or monitor the activities of subjects over time and collect information obtained. For example, the computer system 110 may communicate with various other devices to track different aspects of an activity (e.g., type of activity, duration of the activity, intensity of the activity, results of the activity, effects of activity on the subject, etc.) Individual instances of activities may be tracked and/or composite measures of activities (e.g., frequency, average characteristics, etc.) can be tracked. Subjects can be monitored to detect changes in attributes as well.

In some implementations, the status data may include sensor data collected by one or more of the sensing devices 104*a*-104*c* and sent to the computer system 110. The sensor data may include data collected while the subject, e.g., person, is engaged in a particular activity, in particular, activities such as training activities or assessments. The status data may include data self-reported by the subject, data collected from others, data from sensors, etc.

In some implementations, for example, when the subject is a person, the status data may include one or more of heart rate data of the subject, oxygen saturation data of the subject, data indicating an exercise distance that the subject ran or walked, data indicating an exercise intensity that was performed by the subject, or data indicating a duration of an exercise that was performed by the subject. As discussed above, these can be current or recent values (e.g., the most recently measured) and/or prior values (e.g., a series of historical measurements taken at different times). These various data types and other may be collected using multiple sensors and/or devices, for example the sensing devices 104*a*-104*c*.

The activities tracked by the computer system 110 can include actions that involve or are performed by the subject. Some tracked activities may be directly related to the capability to be developed in the subject, e.g., the readiness criteria used to evaluate the capabilities of the subject. For example, a program for enhancing the capability of the subject may include training, practice, tests, and other actions designed to improve the condition or capability of the subject. The context of the activities (e.g., the location, date, time day, resources allowed, whether performed in a group or alone, who supervised or instructed the activity, etc.) can be tracked and recorded as well. Some tracked activities may not be specifically related to the capability to be developed or may not initially be known or expected to be related to the capability.

The computer system 110 can track attributes or activities of each of multiple subjects over a period of time, as well as changes in levels of capability of the multiple subjects over the period of time. The computer system can the train models based on the tracked data. By tracking many variables (e.g., subject attributes, subject activities, context of the subject and activities, etc.) for many subjects and storing the data in the database, the computer system 110 can obtain a rich data set with which to discover elements that have relevance to the process of a subject acquiring readiness and the manner those elements impact readiness. This data, whether used for machine learning training or through direct analysis and extraction of relationships by the computer system 110, can be used to identify which features are predictive of different types of readiness (e.g., different capabilities of subjects) and to generate models that can be used to make predictions based on those features.

Some tracked data may represent factors that do not seem related to a subject's readiness or capabilities, but nevertheless may be discovered by the computer system to affect the process of at least some subjects in gaining readiness in at least some contexts or circumstances. The computer system 110 can use the examples in the tracked data to identify the relative impact of tracked data items on different capabilities being acquired, how they affect the instantaneous capability vs. the trend or trajectory of acquiring readiness over time, how tracked items affect readiness in combination, how tracked items enhance or diminish the effects of activities in gaining readiness, how tracked data items vary in importance for subjects having different combinations of attributes, and so on.

For example, in the case of athletes, factors such as amount of sleep and diet may affect subjects that have certain genes, fitness levels, experience levels, training histories, behaviors, or other attributes more than other subjects that do not have the same attributes or combinations of attributes. Similarly, tracked factors may affect the acquisition of some capabilities more than others (e.g., sprinting speed vs. distance running speed vs. weight lifting ability), and may have differing impact to enhance, diminish, or have no effect on different training activities.

The process 1200 includes deriving a set of feature scores from the status data for the subject (1204). The feature scores may indicate attributes or activities of the subject. The attributes can be current attributes or former attributes, and so can reflect the progress or change experienced by the subject over time. Similarly, the activities indicated can be current or former activities, such as a set of activities performed to enhance the subject's capability (e.g., training actions, tasks attempted or performed and associated outcomes, etc.). Some feature scores may be based on user interaction with a device, such as user input to a graphical user interface, responses to questions, entered text. Other feature scores may be based on data collected in other way The feature scores can be based on sensor data that is acquired by one or more sensors during one or more activities of the subject or that indicates one or more attributes of the subject. For example, the sensor data can indicate measurements or detection of attributes and activities of the subject, and the feature scores can be the measured or detected values or other values derived from them (e.g., sensor measurements that have been normalized, quantized, rounded, combined, or otherwise adjusted, or classifications based on the measurements). Examples of sensors that can provide data include accelerometers, proximity sensors, temperature sensors, pressure sensors, optical sensors, cameras, GPS receivers, and so on. Examples of sensing devices that can measure physiological parameters include oximeters, glucometers, electrocardiogram sensors, heart rate sensors, electroencephalogram sensors, electromyogram sensors, and respiration rate sensors.

The set of feature scores can include a value for each of multiple predetermined feature types. The feature types can be a predetermined set of data types that have been previously determined by the computer system, for example, as part of analyzing data in the database and constructing the one or more models. The computer system can store data indicating the set of features types (e.g., data types or types of measures to be generated) that correspond to each model. For example, different models for different types of subjects may use feature scores representing different types of information about subjects.

In the example of FIG. 1C, the feature scores may be derived by the computer system 110, e.g., using the data aggregation module 112 to extract and/or organize the activity data. The feature scores may include all or part of the aggregated data 122 shown in FIG. 1C, converted to an input format that the model is configured to accept (e.g., binary values, integers, or other values in a predetermined representation). The feature scores may indicate attributes of the person such as, for example, physiological attributes, such as height, weight, blood pressure, health status, and psychological attributes.

To derive the appropriate set of feature scores, the computer system 110 can select one or more models that are appropriate for the subject, readiness criteria for the subject, and the type of prediction to be made. For each model, stored data can indicate the feature types to be used with the model, such as the types of information to be provided and the format for providing the data to the model (e.g., binary values, integers, floating point values, an appropriate level of precision, etc.). Once the computer system 110 selects a model to use, the computer system 110 can access the data specifying the input feature types for that model and generate them in the format the model is designed to accept.

In general, as part of generating predictive models, the computer system 110 can assess the predictive ability of different data types to indicate readiness, potential for future readiness, and other factors. From this analysis, the computer system can select a subset of the available types of data about subjects to use as features providing inputs to the predictive models. The subset can be a proper subset, e.g., fewer than all of the available types of data. The analysis can be performed at a fine-grained level, for example, with a different set of feature types used for each different type of subject, for each different capability or aspect of readiness to be predicted, and/or for each type of prediction (e.g., current readiness, future readiness, maximum potential readiness, time to reach a particular readiness level, etc.). Indeed, the computer system 110 can train different models for different subjects, readiness criteria, and/or types of predictions, with each model having a corresponding set of feature types representing a subset of the types of information available in the database.

The varied information in the database can also be used to select interventions to enhance readiness. Even if multiple options (e.g., different training programs) tend to increase the capabilities of subjects, different options will nevertheless vary in their effectiveness for individual subjects, which have different combinations of attributes and experience. An activity that provides appropriate improvement for one subject may result in too slow of improvement for another subject, or may have a lower likelihood of being carried out by one subject than another. Based on the information in the database, the computer system 110 can generate models, tables, equations, or other elements that can be used to predict the effectiveness of different training activities or other factors (e.g., different coaches, different environments, different resource levels available to subjects, etc.) given a subject profile (e.g., a combination of attributes and activities). This can be done with machine learning models that trained to output, given input feature scores indicating subject attributes and/or activities, scores indicating the appropriateness of a training activity or other intervention (e.g., a communication to the subject, an output by or a command to a device associated with the subject, a change in behavior of the subject, a notification for a trainer or technician associated with the subject, etc.). This can also be done by generating data for a table indicating the effects of attributes, activities, or other data on readiness, such as shown in the table 400 of FIG. 4.

The set of feature scores derived from the status data can include information about different attributes and/or activities of the subject over time. For example, the feature scores may indicate the activities or attributes of the subject at each of multiple points in time. For example, different instances of activities (e.g., training activities, attempts to perform a task, etc.) can each be provided so they can be used in making predictions. Similarly, the values or measures indicative of different subject attributes at different times can also be provided. In some cases, information about different points in time, e.g., time series data for a subject, can be provided by concatenating multiple sets of feature values, each representing attributes and activities at different times, into a single input feature vector or input data set for a model. As another example, multiple sets of feature values can be provide to a model separately, e.g., sequentially as a sequence of multiple feature vectors, and the model can include a memory capability to retain information from the processing of one input vector to the next. A recurrent neural network, such as one including long short-term memory (LSTM) blocks, or other model can be used for this purpose.

The process 1200 includes providing the feature scores to one or more models (1206). For the example of FIGS. 1A-1C, the feature scores may be provided to the scoring and prediction module 114 that includes the machine learning models 130, 132, and 134. The one or more models can be models configured to predict readiness of subjects to satisfy one or more readiness criteria.

The one or more readiness criteria can represent a predetermined state or level of capability that can be used as a reference to evaluate the subject. For example, the readiness criteria can define a desired physical state of the subject (e.g., certain physical attributes), a desired functional state of the subject, and/or a desired level of capability of the subject to perform a task. The readiness criteria may be defined in any of various different ways. For example, the readiness criteria can specify a target state in which a subject is capable of performing a task or action. As another example, the readiness criteria can specify that a subject should be capable of performing a task or action in a particular manner (e.g., satisfying a predetermined threshold for speed, latency, accuracy, precision, consistency, efficiency, reliability, scalability, capacity, throughput, volume, intensity, etc.) or according to a performance standard. The readiness criteria may include multiple components, for example, they may require a subject to have the capability to perform each of multiple different tasks to reach the standard of readiness specified by the readiness criteria.

The one or more models may include one or more machine learning models. The one or more models comprise at least one of a neural network, a support vector machine, a classifier, a regression model, a clustering model, a decision tree, a random forest model, a genetic algorithm, a Bayesian model, or a Gaussian mixture model. The one or more models may include statistical models, rule-based models, and other types of models. The feature scores may be provided as a feature vector, e.g., a sequence of values where each value corresponds to an input slot (e.g., a portion of an input layer of a neural network) designated for a certain type of data.

In some implementations, the one or more models have been trained based on training data indicating (i) activities or attributes of other subjects and (ii) outcomes for the other subjects with respect to the readiness criteria. The training can use the respective progressions of readiness of the other subjects over time to configure the one or more models to predict readiness of subjects to satisfy one or more readiness criteria.

The one or more models can be trained, based on data from the database about multiple subjects, to predict the readiness of the subject at the current time or at a time in the future. The models can be configured to make these predictions using current information about the subject, historical information about the subject, and/or information about planned or anticipated future activities of characteristics of the subject (e.g., a training plan, estimated improvements in a capability based on current trends or patterns, etc.) In general, the data in the database can indicate, for each of multiple subjects, a variety of data points indicating attributes of the subjects, activities of the subject, and other information.

The data in the database can provide examples of the patterns, trends, and/or progressions in achieving readiness that subjects experienced. For example, the data can indicate, for subjects of different combinations of attributes, which activities enhanced readiness (e.g., performance capabilities) as well as to what extent they enhanced readiness. This can indicate, for example, how soon different activities or actions improved capabilities, which combinations were most effective (e.g., which combinations provide synergies), which subject attributes made subjects more or less likely to improve with different activities, the magnitude of the effect that different activities and attributes have on readiness, and so on. The computer system can analyze the examples in the database to determine these relationships, either through explicit analysis or through machine learning training, e.g., so that a model implicitly learns the predictive value of different data items on current or future readiness. Training can incrementally or iteratively update the values of parameters in the models to learn the impact of different factors on predicted outputs. In the case of neural networks, back-propagation can be used to alter neural network weights for neurons at various layers of the neural network model.

Models may be trained to predict future readiness by, among other techniques, training with input-target pairs with a mismatch between the inputs and targets. For example, the data indicating attributes, past activities, and/or planned future activities for subjects after one month of a training process can be used to generate input features, while data indicating the measured, actual readiness of those subjects after three months of the training process can be used at the output targets. By training with these data pairs, the computer system 110 can train a model to use the information about subject at one time period to output the results achieved at a different time period. Of course, similar techniques can be used without a mismatch between input and training targets to train a model to predict the readiness at the current time, e.g., so that models learn to predict current readiness based on current input data.

Another technique that can be used to train the models is to use the longitudinal progress of subjects to learn the patterns, trends, and progressions of readiness over time. For an individual subject with data collected at 10 different weekly intervals, this can provide ten different examples for training a model to predict readiness at the 10-week time. Each example can reflect cumulative interactions of prior weeks. For example, the data at the end of the first week (along with a value indicating that the input corresponds to the first week) can be used as on training input, with the eventual 10-week readiness score as the training target. The data at the end of the second week (along with a value showing that the input corresponds to the second week) can be used as on training input, with the same eventual 10-week readiness score as the training target. Data from other weeks can be used in the same manner to create other training example data points. By training in this manner, using the examples of many different subjects having different attributes and experiences, the model can learn the typical trends of readiness progression so it can predict readiness based on data representing different time periods or stages in acquiring readiness. The training process can also indicate the variability in these patterns and progressions, allowing the model to output, for example, a confidence level for predictions.

The process 1200 includes providing, based on output of the one or more machine learning models, output indicating the subject's readiness (1208). With respect to FIGS. 1A-1C, the output indicating the subject's readiness may be outputted by the scoring and prediction module 114. The output may be a readiness score. For example, in some cases, the output is a readiness score indicating a predicted physical or information processing performance of the subject, whether representing the current time (e.g., the time corresponding to the most recent feature values for the subject) or a future time. In some cases, the output is a readiness score indicating a combination of both the physical and information processing performance of the subject. The output may take into account the subject's current physical and/or mental performance as well as the subject's performance trend (e.g., history of progression in measured readiness or predicted readiness score for multiple previous times).

Models can be generated to make different types of predictions (e.g., completion readiness time (CRT), future readiness probability (FRP), altered course success rate (ACS), etc.) with respect to different readiness criteria. Typically, a different model can be generated for each type of prediction to be made. Models can be generated for each type of readiness criteria also. A first model can be generated to make FRP predictions for one set of readiness criteria, and a second model can be generated to make FRP predictions for a different set of readiness criteria. In some implementations, a model may be configured to predict readiness with respect to any of multiple different readiness criteria, with the readiness criteria being specified as an input at the time of generating a prediction. For example, a model may be trained to predict readiness for physical capability of a person, and various parameters indicating the level of fitness (e.g., an amount of weight to be lifted, a time for running a certain distance, etc.) can be provided with the feature data as input to the model, allowing the model to tailor each prediction for the readiness criteria specified. The model can be so configured by training the model with examples that involve different readiness criteria and by providing values indicating the applicable readiness criteria during training.

The output may be a predicted time of when the subject will achieve readiness to satisfy the one or more readiness criteria. The prediction can take into account various factors which can be reflected in the feature values, e.g., current attributes of the subject, prior attributes of the subject, a history of activities of the subject, a planned or scheduled activities of the subject, resources available to or assigned to the subject (e.g., equipment, hardware, software, technicians, doctors, consumables, training courses, time, financial resources, etc.).

The output may be a likelihood or prediction whether the subject will achieve readiness to satisfy the one or more readiness criteria. This can be provided in the form of a binary prediction (e.g., yes or no), a confidence score (e.g., a value indicating an 80% confidence in a classification), a likelihood (e.g., a value indicating a 70% likelihood of achieving readiness), and so on. The prediction may be whether the subject will ever achieve readiness (e.g., has the capacity to ever acquire the reference level of ability represented by the readiness criteria) or whether the subject will achieve readiness in a certain scenario or given certain conditions. The model can take into account one or more constraints, whether built into the model through training or specified as in input to the model. For example, the constraints may limit at least one of, a time to achieve readiness, resources available to the subject, or a training plan (e.g., planned, scheduled, or anticipated training activities) for the subject.

As an example, the constraints used in a generating a prediction may specify a future time that readiness potential is being judged (e.g., a specific date, or an amount of time in the future, such as one month). The constraints may also condition the prediction on factors such as the availability of certain resources or limitation on the use of certain resources, the elements planned for assisting the subject in achieving capability (e.g., assuming that a certain set or type of training activities will take place), and so on. Thus, the system enables a user to obtain a prediction whether a subject will satisfy the readiness criteria at a defined time in the future, or if the system will ever be able to satisfy the readiness criteria.

In general, any of the predictions discussed in this document may be optionally generated based on one or more constraints. In some cases, these constraints may be designed into a model at the time of training. For example, a model may be trained to predict whether readiness will be achieved within one month. In some cases, the constraints may be indicated to the model, e.g., as input parameters along with feature scores for a subject. For example, a model may be trained to provide predictions based on variable time frames, with the time frame of interest being specified as input to the model at the time of inference processing rather than training. In some cases, constraints may be accounted for through post-processing of model outputs, combining outputs of multiple models, or through other techniques.

Other types of predictions can be generated, based on feature scores derived from the database, with appropriately trained models. For example, models can be configured to predict the type and amount of resources or training activities that would be needed for individual subjects to reach the readiness criteria.

The process includes providing output data based on the prediction (1210). The output can be configured to, for example, alter a user interface of a device or alter interaction of a device with the subject. The user interface may be a user interface of, for example, a phone or computer used by the subject or a person associated with the subject (e.g., a coach, a doctor, etc.).

Interaction of a device with a subject can include changing how a device monitors a subject, e.g., change the type, frequency, precision, or manner of obtaining measurements about a subject. For example, if a prediction indicates that at subject is not meeting a readiness target, the frequency of monitoring the subject may be increased and additional types of data may be collected. As another example, for a subject that is a person, the manner in which a phone, wearable device, or other device interacts with the subject can be changed. For example, any of various interactions can be initiated, discontinued, or modified, e.g., audible outputs, visible outputs, haptic outputs, reminders, recommendations, surveys, practice or training activities administered using the device, etc. In some implementations, the actions of medical monitoring or treatment devices can be changed, e.g., to adjust frequency or dose of medication or to adjust the process of measuring physiological parameters.

In some implementations, an indication (e.g., a score, color, image, icon, graph, text, etc.) of the prediction is provided to the subject, to a device associated with the subject (e.g., a tool, phone, wearable device, monitoring device, etc.), to a person associated with the subject (e.g., a technician, administrator, coach, doctor, researcher, etc.), or to a device associated with the subject. The indication of the prediction can be provided in a visualization, such as a chart, graph, timeline, scatterplot, map, table, etc. that shows past, present, and/or future readiness of the subject. The indication can be provided through various channels, such as an e-mail, a text message (e.g., short message service (SMS) or media message service (MMS)), a notification, an alert, a web page, and/or content of an application (e.g., a mobile device application or computer application). The output data can be provided to a local device or to a remote device, such as over a computer network such as the Internet.

As an example, a score indicative of the prediction can be provided for display on a user interface. The output data can include an indicator of the prediction for display on a user interface. The output data can include visualization data, generated using the prediction, for illustrating a timeline or trend of predicted readiness of the subject over time. The output data can include a recommendation, determined based on the prediction, of an action to improve or accelerate acquisition of readiness of the subject to satisfy the one or more readiness criteria. For example, the recommendation can include a proposed change to a plan for enabling the subject to reach readiness (e.g., an upgrade plan for a network, a maintenance plan for a device, a training plan, a medical treatment plan, etc.). The output data can include data to cause display of one or more interactive user interface controls that, when selected by a user, alter one or more planned actions (e.g., a training plan) for assisting the subject to achieve readiness to satisfy the one or more readiness criteria.

The output data can include data to cause display of one or more interactive user interface controls that enable a user to select from among multiple options for assisting the subject to achieve readiness to satisfy the one or more readiness criteria (e.g., different activities, resource allocations, configuration changes, medical procedures, etc.). The output data can include an indication of a predicted change in readiness of the subject, relative to a level of readiness indicated by the prediction, for each of one or more actions with respect to the subject. In other words, different options can be provided, each with a predicted effect of selection of that option, e.g., an indication of how much more quickly or more efficiently the subject would achieve readiness, or an indication of a predicted change to the subject's readiness score if the option is selected. For example, an option might have a corresponding indicator that the time to reaching readiness would be reduced by an amount (e.g., 10%, 20%, etc.) or a certain amount of time (e.g., one week, three days, etc.). To obtain these predictions, an altered set of features scores can be determined for each option, with the candidate action or activity being reflected in the feature scores. The trained models discussed above can then be used to determine the predictions of the ultimate effect of altered training plans that include different selectable options. The results of these can be compared to the predictions made without those training options, to show the relative amount of change (e.g., improvement) that each option has the potential to provide.

In some implementations, the computer system 110 computes a readiness score, for example, a numerical indication such as a number within a range (e.g., a number between and including 0-10). There may be multiple readiness scores generated for a subject to represent predicted readiness for different criteria and/or to represent readiness at different times. For example, there may be a readiness score for the subject's physiological performance, e.g., that indicates how physically fit or in shape the subject is. There may be a readiness score for the subject's psychological performance, e.g., that indicates how mentally stable, resilient, or prepared the subject is, either generally or for a specific task. There may also be an overall readiness score that is calculated using readiness scores for the subject's physiological and psychological performance. The overall readiness score may be a combination of the readiness scores for the subject's physiological and psychological performance. The overall readiness score may be calculated by applying a first weight to the physiological readiness score and a second, different weight to the psychological readiness score, and combining the weighted scores. For example, for a particular job role, the physiological readiness score may be weighted 70% and the psychological readiness score may be weighted 30%.

In some implementations, in determining a readiness score, one or more past performances of the subject may be analyzed. These past performances may indicate whether the subject previously failed one or more challenges, completed one or more challenges, ignored or missed one or more challenges, how often the subject completed one or more challenges, how often the subject failed one or more challenges, how well the subject performed on challenges compared to other subjects, how well the subject performed on challenges compare to other subjects in the same group or team, how well the subject performed on challenges compared to past subjects, or the like. This past performance information may be stored and/or organized by the data aggregation module 112 shown in FIGS. 1A-1C. This past performance information may be used, e.g., by the data aggregation module 112 and/or the scoring and prediction module 114 shown in FIGS. 1A-1C, to generate a performance trend of the subject. The performance trend may be used, e.g., by the scoring and prediction module 114, with the subject's current performance in order to determine a readiness score for the subject. For example, if the subject is currently performing at a level of 5/10 but has a positive performance trend, the scoring and prediction module 114 may determine that the subject has a readiness score of 6/10. Similarly, if the subject is currently performing at a level of 5/10 but has a negative performance trend, the scoring and prediction module 114 may determine that the subject has a readiness score of 4/10.

In some implementations, providing the output includes providing a predicted time that the subject will achieve readiness. This time may be provided in addition to or in place of a readiness score. The predicted time may be determined by the scoring and prediction module 114 shown in FIGS. 1A-1C. The predicted time may be calculated using the current performance of the subject, the set readiness score or performance goal that the subject needs to achieve, and the performance trend of the subject. For example, if the subject's current performance is 5/10, the set readiness score is 8/10, and the subject's performance trend indicates an improvement in performance of 1/10 every month, then the scoring and prediction module 114 may determine and output a time of three months for when the subject is predicted to achieve readiness.

In some implementations, providing the output includes providing a likelihood or prediction whether the subject will achieve readiness. This likelihood or prediction may be provided in addition to or in place of a readiness score and/or a time that the subject will achieve readiness. For example, the likelihood or prediction may be provided as output when the scoring and prediction module 114 shown in FIGS. 1A-1C is unable to determine a time when the subject will achieve readiness, e.g., when the calculated time is infinite due to the subject having a current performance under a set readiness score and having a negative performance trend. The likelihood or prediction may be determined by the scoring and prediction module 114 shown in FIGS. 1A-1C. The likelihood or prediction may be calculated using the current performance of the subject, the set readiness score or performance goal that the subject needs to achieve, the performance trend of the subject, and one or more performance criteria. For example, if the subject's current performance is 5/10, the set readiness score is 8/10, the subject's performance trend indicates an improvement in performance of 1/10 every month, and the performance criteria requires that the subject achieve readiness within two months, then the scoring and prediction module 114 may output a 20% likelihood or prediction indicating that the subject is unlikely to achieve readiness in the two-month timeframe.

In some implementations, group readiness criteria refers to readiness criteria that is applied to every subject in the group. For example, the group readiness criteria may require that each person in a group be able to run two miles in under fourteen minutes, perform twenty pull-ups, and perform fifty pushups within a two month timeline.

In some implementations, the computer system 110 monitors readiness by repeatedly generating predictions about subjects' readiness and compares the predictions with reference values (e.g., thresholds, ranges, targets, milestones, etc.). In some cases, the reference values may be set to measure progress over time relative to trend, such as an average trend or progression of readiness acquisition determined from the progression of multiple subjects. In this manner, if a subject's profile in the database becomes indicative of a change in readiness the computer system 110 can detect it and provide an appropriate notification, as well as recommendations of corrective actions to bring the readiness progression back to the desired level. The computer system can thus detect when a subject's readiness predictions show a deviation from the typical trend that has been employed by other subject who have successfully acquired readiness. As noted above, the trends or values used for reference can be learned from the data in the database, and so can model many different types of readiness progressions, including complex non-linear trends over time.

To support readiness monitoring, new predictions can be made periodically (e.g., at intervals or after a certain time has elapsed) or in response to receiving new data about a subject (e.g., upon receiving updated sensor data, subject attributes, subject activities, changes to training plans, etc.). Based on the comparison of the subject's predicted readiness level and the reference values, alerts or notifications can be provided, for example, to a device or electronic address associated with the subject or a person associated with the subject (e.g., an administrator, a technician, a coach, a doctor, a researcher, etc.). For example, if a subject's readiness does not reach a certain milestone (e.g., the readiness declines, the readiness does not improve over a period of time, or improves less than a desired amount), then the computer system 110 can detect this and notify appropriate devices and users.

In some implementations, the subject is a group of individual subjects. The one or more readiness criteria can include one or more group readiness criteria, e.g., representing a level of readiness for the group as a whole. Receiving status data can include receiving status data indicating activities and/or attributes of individual subjects in the group. The computer system 110 can generate, based on the activity data, a readiness score for each of the individual subjects in the group. The readiness scores can indicate predictions of the respective capabilities of the individual subjects in the group. The computer system 110 can also generate a group readiness measure that indicates a predicted ability of the group of individual subjects to collectively satisfy the one or more group readiness criteria. When the subject represents a group, the output data can indicate (i) a predicted time that the group will achieve readiness to satisfy the one or more group readiness criteria and/or (ii) a prediction whether the group will achieve readiness to satisfy the one or more group readiness criteria given one or more constraints.

When new status data is received, e.g., data indicating additional activities of the subjects in the group, the computer system 110 can generating a new readiness score for each of the subjects in the group and generate a new group readiness measure. The computer system can provide additional output data indicating (i) a new predicted time that the group will achieve readiness to satisfy the one or more group readiness criteria or (ii) a new likelihood or prediction whether the group will achieve readiness to satisfy the one or more group readiness criteria, for example, given one or more constraints. The computer system 110 may compare the most recent prediction to earlier predictions, and indicate how readiness has changed over time. For example, the computer system 110 can provide output that causes a plot or curve of readiness measures (e.g., scores, readiness times, etc.), lists predictions for different times, or indicates whether predicted readiness times of scores have increased or decreased.

In some implementations, the computer system 110 may change the composition of a group. For example, in response to determining that the group readiness measure does not satisfy the threshold, the computer system 110 may remove from the group one or more subjects determined to have individual readiness scores that are less than an average of individual readiness scores for subject in the group. As another example, the computer system 110 may add to the group one or more subjects having individual readiness scores that are greater than an average of individual readiness scores for subject in the group.

Figure 13:
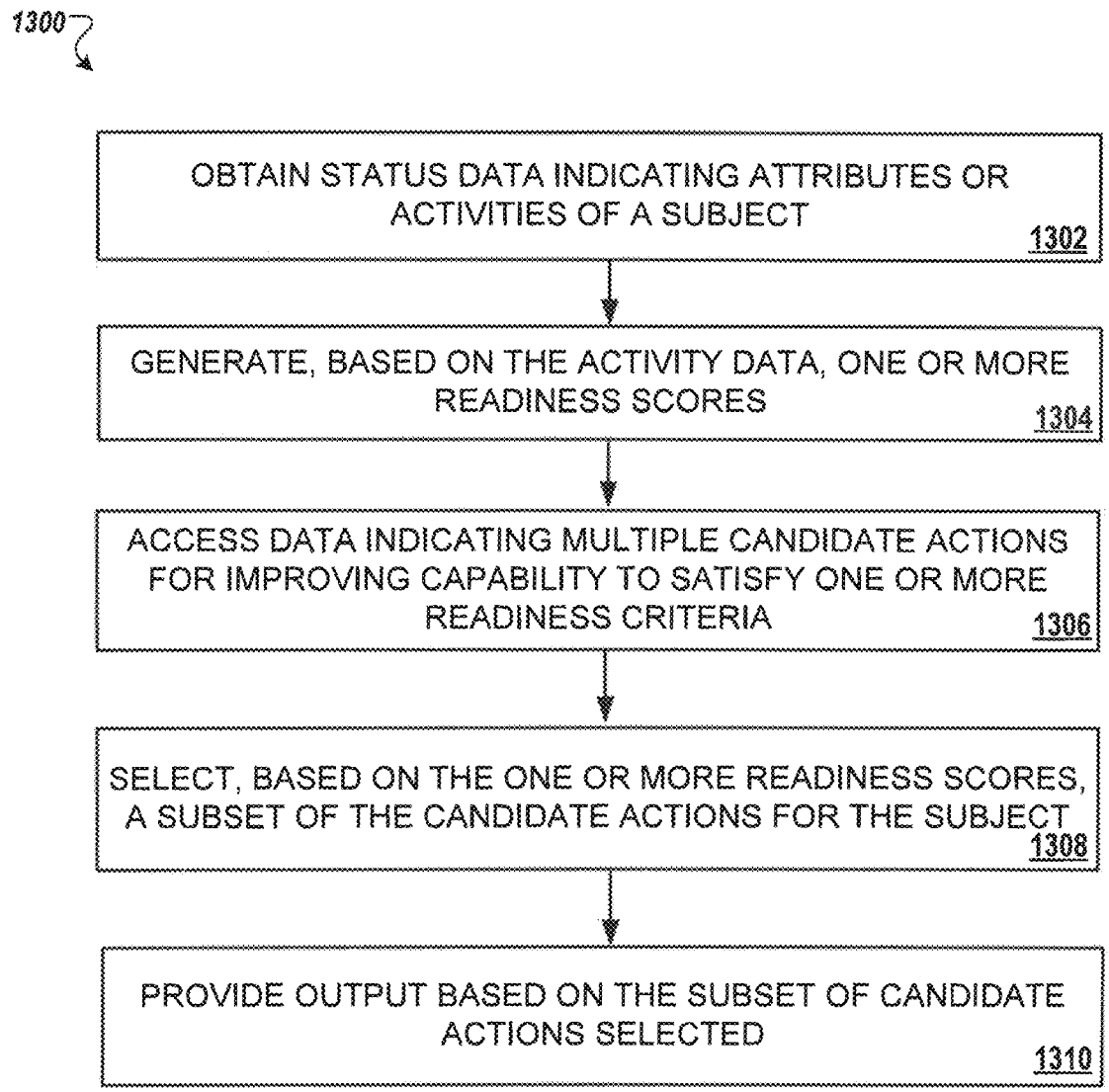
FIG. 13 is a flowchart that illustrates an example process for tailoring training to improve readiness.

FIG. 13 is a flowchart that illustrates an example process for tailoring training to improve readiness. The process 1300 can be performed by one or more computers, such as the computer system 110 described above. Steps of the process 1300 can be performed by one or more servers, one or more client devices, or by a combination thereof and/or other devices.

The process 1300 includes accessing a database to obtain status data that indicates attributes and/or activities of a subject (1302). This can include obtaining status data as discussed above with respect to step 1202 of FIG. 12. As discussed above, the status data can indicate current and former attributes of the subject and a variety of activities of the subject over time and results of those activities. The status data can include data provided by an electronic device to the one or more computers over a communication network.

The process 1300 includes generating, based on the activity data, one or more readiness scores (1304). A readiness score can indicate a level of capability of the subject to satisfy one or more readiness criteria. The readiness score can indicate a prediction of current readiness or a prediction of future readiness. These readiness scores can be outputs of models, such as machine learning models, statistical models, rule-based models, or other models as discussed above. For example, the one or more readiness scores can be generated using one or more models such as, for example, the machine learning models 130, 132, and/or 134 shown in FIG. 1C. The readiness score(s) can be obtained for a subject using steps 1204, 1206, and 1208 of FIG. 12, as discussed above.

The readiness scores may indicate that the subject is not yet capable of satisfying the one or more readiness criteria. For example, the readiness scores may indicate that the subject is predicted to not satisfy the one or more readiness criteria within a certain time frame, e.g., at a specific time in the future, given the status data in the database. As discussed with respect to FIGS. 1A-1C, the readiness scores may be generated by the scoring and prediction module 114.

The readiness criteria may be set by input provided through a computer interface, such as a user interface of a client device. The readiness criteria can be set by a user, for example, an administrator, a technician, a coach, a counselor, a caregiver, a care provider, a specialist, an employer, a potential employer, or a supervisor of the subject. The readiness criteria may make up or be part of the third-party input 152 shown in FIG. 1B. With respect to FIG. 6, the readiness criteria may be included in the program data store 638 and/or in the subject outline and content 626*a*.

The process 1300 includes accessing data indicating multiple candidate actions for improving capability of the subject to satisfy one or more readiness criteria (1306). The computer system 110 can access a database that includes information describing various different candidate actions that can assist subjects to acquire different capabilities. Different candidate actions may be better suited for acquiring some capabilities than others. Also, different candidate actions may have better effects for subjects having certain attributes than others.

The candidate actions may include interactions of devices, changes in the types or amounts of resources available, changes in the training program or training plan for a subject, and so on. For example, there may be multiple different training programs that use different techniques to enhance a person's athletic capability. One set of training programs may improve strength, and others may be designed to improve flexibility, while yet others may be designed to improve balance, endurance, running speed, swimming ability, and so on. Within each training program, there may be a combination of elements, such as exercises, classes, practice activities, classes, and other activities for the subject to participate in. The candidate actions can include the assignment of a subject to a training program and/or assignment of certain elements within the training program. Additional examples of candidate actions may include different medical treatment options, e.g., physical therapy exercises, medications, surgeries, etc. Other candidate actions may include interactions with mobile devices (e.g., reminders, surveys, media, etc.) or proposed changes in behavior (e.g., changing diet, sleep habits, and so on).

As additional examples, the candidate actions can include changing a frequency, number, or intensity of planned training activities for the subject. The candidate actions can include changing an allocation of resources for the subject. The candidate actions can include changing a type of training for the subject. The candidate actions can include changing an assignment of an individual to assist the subject in achieving readiness (e.g., assigning a new technician, coach, doctor, manager, etc.). The candidate actions can include providing, for output by a client device, a notification indicating the level of capability of the subject to satisfy one or more readiness criteria that is indicated by the one or more readiness scores.

The candidate actions can include actions that are manually entered and designated for improving specific capabilities. Additionally or alternatively, the candidate actions can be automatically discovered or inferred by the computer system 110 based on the data in the database. Because of the rich set of data that is tracked for many subjects over time, the computer system 110 can infer the potential effects of many different actions and designate them as candidate actions for improving different capabilities. For example, the computer system 110 may determine, through analysis of the data in the database, that computer systems performed more efficiently if they had been restarted within a certain amount of time, and as a result enumerate restarting a computer as a candidate action to improve readiness. Similarly, for a subject that is a person, location data and other data may indicate that subjects that spent time outdoors had improved mood or improved performance on a task. As a result, a candidate action to cause the subject's phone to output a message encouraging the subject to take a walk outside may be added as a candidate action.

In the example of FIG. 1C, candidate actions include various training options indicated in output data 146 (e.g., potential interventions "1", "2", "3", "5", "6", and "7"). The candidate actions in that example are shown to indicate the predicted effects of the different options (e.g., achieving readiness "12% faster" or "4% faster").

The process 1300 includes selecting a subset of the candidate actions for the subject based on the one or more readiness scores (1308). The subset can be a proper subset, e.g., fewer than all of the candidate actions evaluated. Various different techniques can be used to select candidate actions to recommend or carry out for a subject. For example, the set of available actions may be filtered according to those that are predicted to improve readiness with respect to the readiness criteria for the subject. In other words, if the readiness criteria include measures of strength or speed, candidate actions that are not predicted to improve those capabilities are not selected. Similarly, the set of candidate actions can be filtered to a subset by evaluating the magnitude of predicted improvement, the resources required for the actions, or both, so that only actions that provide at least a minimum level of predicted improvement and/or require less than a maximum amount of resources are selected.

Whether any candidate actions are selected to be carried out or recommended can be based on the readiness scores. The one or more readiness scores indicate a predicted current or future level of readiness, for example, as a prediction of when or whether the subject will achieve readiness, or as a score along a scale for assessing levels of capability. Actions to change the training or preparation of a subject can be selected in response to the readiness scores indicating that improvement in readiness is needed. For example, the scores can indicate whether intervention is needed for the subject to reach a desired level of readiness, as well as the type and extent (e.g., magnitude, frequency, or intensity) of intervention needed.

The computer system 110 may use the one or more readiness scores to determine whether the subject currently meets or a target level of readiness or is projected to do so in the future. When the computer system 110 determines that scores do not meet the target level, the computer system 110 can select a subset of the candidate actions for the subject in order to improve the readiness of the subject. Thus, based on the level of readiness indicated by the readiness scores, the computer system 110 can select a type and amount of candidate actions that are predicted to bring the subject's readiness to or closer to a desired readiness level or trend of acquiring readiness.

For example, the readiness scores for the subject can be compared with reference scores, and the comparison may indicate that the subject does not yet satisfy the one or more readiness criteria or that the subject is predicted to not satisfy the readiness criteria at a time in the future. Similarly, the trend or progression of the subject's readiness scores over time may be compared with the trends or progressions of subjects that successfully achieved readiness and subjects that did not. In other words, the scores for a subject at a particular stage in acquiring readiness (e.g., after 1 month of training) may be compared with scores representing other subjects at the same stage (e.g., when the other subjects had completed 1 month of training).

As discussed below, a customized subset of actions can selected for each subject, taking into account the subject's attributes, the subject's history of activities, the subject's current capabilities and predicted future capabilities, the subject's planned future activities, the particular set of readiness criteria for the subject, and so on. The selection can also take into account the predicted improvement to readiness that the respective actions provide and the amount of improvement in readiness that the particular subject needs in order to reach a desired readiness level or readiness progression.

The computer system 110 can access data indicating how the respective candidate actions are predicted to affect the readiness of the subject to satisfy the one or more readiness criteria. The indications can be stored in association with the data indicating the candidate actions. For example, in a manner similar to the way the table 400 in FIG. 4 shows the potential effects of different genes on capabilities and the magnitude of those effects, data can also be stored to indicate the manner and magnitude of each of the candidate actions (e.g., training options or other interventions) on different capabilities. The values indicating the manner and magnitude of these effects can be generated from the data in the database, which shows the longitudinal progression of readiness of various subjects over time. The computer system 110 can identify instances of the different candidate actions among the data in the database, and then evaluate the relative effect of those actions on the capabilities of the subjects at one or more times in the future.

In some implementations, the data indicating the predicted effects of candidate actions on different capabilities are expressed as scores. For example, a particular activity, such as running three miles, may have multiples scores, each representing how the activity is expected to affect capability or physical state of the subject, e.g., running speed, running endurance, balance, heart health, etc. These scores may be predetermined for the various candidate actions. In some implementations, the computer system 110 can adjust or generate the scores for candidate actions in a customized manner for individual subjects. For example, the computer system 110 can generate the scores can take into account the particular attributes of the subject, for example, by weighting the information in the database about other subjects according to their similarity to attributes of the subject being evaluated. In a similar manner, the scores can be customized to account for the history of activities of the subject, the progression or change in attributes of the subject over time, and other factors.

The process 1300 includes providing one or more outputs based on the selection of the subset of candidate actions for the subject (1310). In some cases, the output causes one or more selected actions to be performed or causes an indication of the selected actions to be presented on a user interface.

The output can include output data configured to cause one or more of the actions in the selected subset to be performed by the computer system 110 or another system. For example, the computer system 110 may change to a training plan for the subject to include the selected actions, or may send a command to another system to do so. Various actions such as initiating communications with a subject, sending a command to a device, changing data collection and monitoring, or altering software behavior can be performed directly by the computer system 110.

In some implementations, the computer system 110 may initiate at least some types of actions automatically when they are selected as being appropriate for the subject. For example, for actions within a certain group or actions that require less than a maximum level of resources, the computer system 110 may automatically adjust training plans and interactions with the subject to include those actions if predicted to be appropriate for the subject. The computer system 110 may determine to implement the selected actions that it is authorized to carry out, or may apply further evaluation criteria to filter the actions further. For example, the computer system 110 may evaluate the predicted effectiveness and resource requirements of the actions, and determine to implement only actions that provide at least a minimum level of increase to readiness predictions and/or involve less than a maximum level of resources.

As another example, the computer system 110 can cause an indication one or more of the actions in the selected subset to be presented on a user interface of the computer system 110 or another system. For example, the computer system 110 can send data causing a user interface of a device to indicate the selected actions as recommendations or options to improve readiness. The indications may be provided for approval or confirmation by a user before they are carried out. The indications can be provided to a device of an individual associated with the subject, for example, a manager, technician, coach, counselor, caregiver, care provider, doctor, specialist, employer, potential employer, or supervisor. Examples include the device 208 shown in FIG. 2A or the device 308 shown in FIG. 3. The output may be presented on a user interface of a device associated with the subject, e.g., the device 204 shown in FIG. 2A or the device 304 shown in FIG. 3.

In some implementations, the computer system 110 uses the selected actions to change a plan of future activities to increase readiness of the subject to satisfy the one or more readiness criteria. The computer system 110 can provide a recommendation, for presentation on a user interface of a client device, of one or more of the actions in the selected subset. For example, the computer system 110 can cause to be presented the top N candidate actions having the highest predicted improvement to readiness of the subject, where N is an integer.

In some implementations, the computer system 110 provides one or more interactive user interface controls configured to initiate one or more of the actions in the subset in response to user interaction with the one or more interactive user interface controls. For example, a button or other control can be provided for each option, and the corresponding action can be performed when a user selects the corresponding control.

In some implementations, the output data includes one or more scores indicative of a predicted change to the readiness of the subject to satisfy the one or more readiness criteria. IN addition, or as an alternative, the output data can provide visualization data to illustrate a timeline or trend indicating a progression of readiness of the subject to satisfy the one or more readiness criteria if one or more of the selected actions are performed.

The user interface can be configured to show the predicted effects of selecting to implement different actions or combinations of the actions for the subject. For example, different predicted readiness dates can be shown for each of the different options. As another example, scores or other indicators can indicate the amount of improvement expected (e.g., an amount of time reduced before reaching readiness, a percentage of resources saved, an amount that capability is increased, etc.). As another example, the different progressions of readiness over time for different actions can be presented in a visualization on a user interface, such as in a chart, graph, table, timeline, etc. For example, a chart can be provided that shows different curves representing the projected progression of readiness scores for the subject in the future if different actions are implemented, along with a curve showing the expected progression of readiness of the subject if none of the options are selected.

Figure 14:
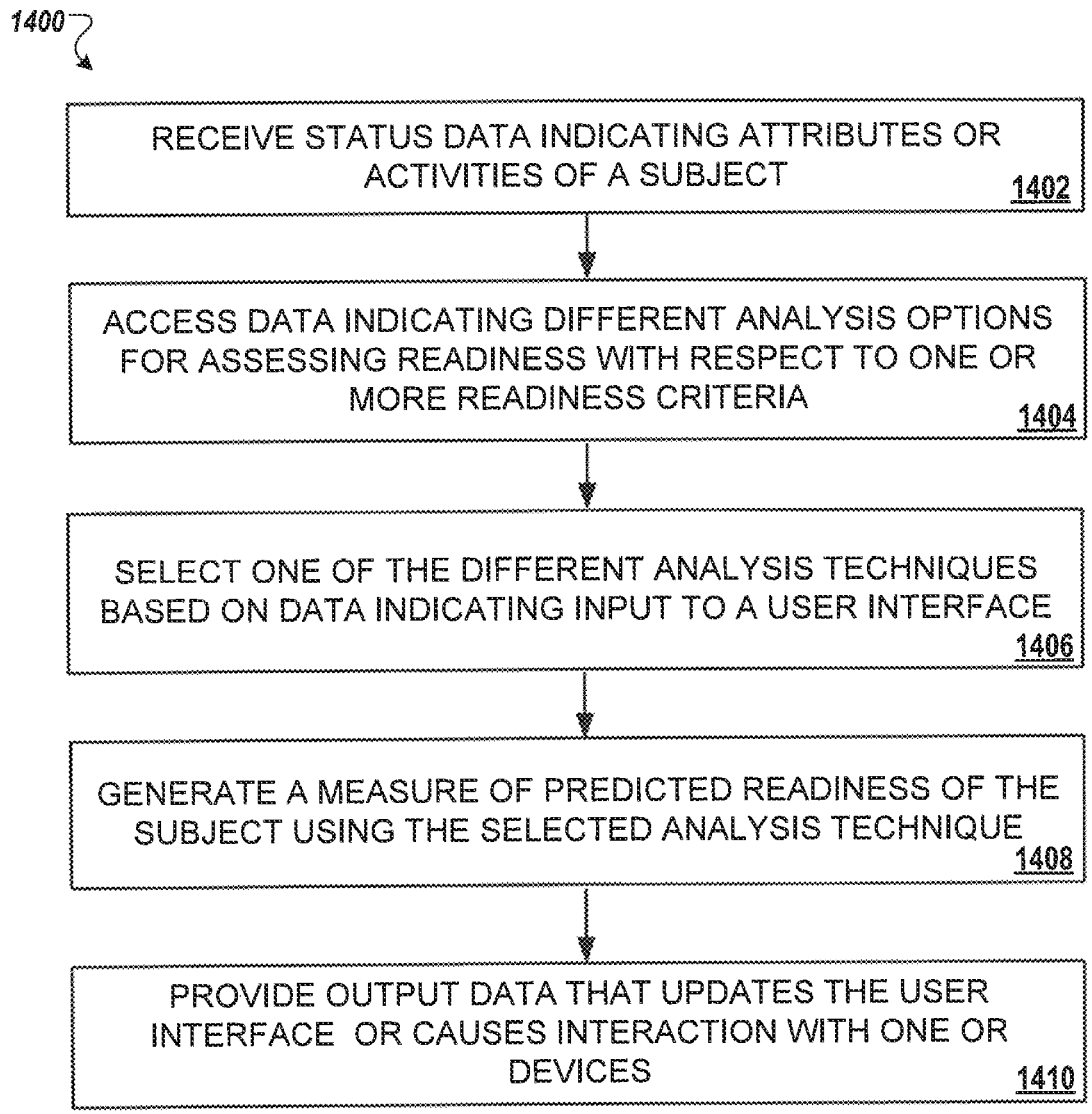
FIG. 14 is a flowchart that illustrates an example process for predicting readiness.

FIG. 14 is a flowchart that illustrates an example process for predicting readiness. The process 1400 can be performed by one or more computers, such as using the computer system 110 described above. Steps of the process 1400 can be performed by one or more servers, one or more client devices, or by a combination thereof and/or other devices.

The computer system 110 can be configured to incorporate and interface with any of various third-party models and analysis techniques. For example, the computer system 110 may provide an interface for a user to add, download, or connect models or analysis software to the computer system 110, to provide additional options for the computer system 110 to use. Of course, the computer system 110 may additionally or alternatively generate and train models based on data in the database 125.

The process 1400 includes receiving data indicating attributes or activities of a subject (1402). This can include obtaining data from a database, as discussed for step 1202 of FIG. 12. Data can be received through a variety of devices, sensors, user inputs, and so on. With respect to FIG. 1B, the data may include sensor data collected by one or more of the sensing devices 104a-104c and sent to the computer system 110. The sensor data may include data collected while the subject, e.g., person, is engaged in a particular activity indicated in the received data. The activity data may include data self-reported by the subject.

The process 1400 includes accessing data indicating multiple different analysis options to assess readiness with respect to one or more readiness criteria (1404). In some cases, the analysis options assess the potential of a subject to achieve readiness by being capable of satisfying the one or more readiness criteria. As discussed above, assessing readiness may involve predicting current readiness, predicting future readiness, predicting a time readiness will be achieved, predicting whether readiness will be achieved by a certain time, and so on. Multiple analysis options can be available and identified for each of these different types of predictions.

Each of the multiple analysis techniques can use example data indicating (i) activities or attributes of other subjects and (ii) outcomes for the other subjects with respect to at least one of the one or more readiness criteria. The analysis techniques can predict readiness of subjects to satisfy one or more readiness criteria based on progressions of readiness of the other subjects over time, as indicated in the example data from the database.

The different analysis options can be different analysis techniques, for example, multiple different models, that are all configured to make a same type of prediction, thus allowing the different options to generate different predicted values that are comparable (e.g., represent the same item being predict). For example, there may be different models for predicting future readiness probability for a particular set of readiness criteria, where the models take into account different combinations of input data, have been trained using different training data, use different assumptions or inferences, are configured to predict with different accuracy or variance characteristics, and so on. The computer system 110 may have multiple of these options available, so that the computer system 110 or a user can select one or more appropriate options from the set. In some cases, the computer system 110 generates predictions of the same type using different analysis options (e.g., different models, different constraints, input data representing different granularity or time ranges, etc.), and provides the multiple predictions for presentation.

In some implementations, the multiple analysis options comprise models trained based on different sets of training data, using different training parameters, or using different training techniques. The models may include models with different structures (e.g., neural networks with different sizes, different numbers of layers, different types of layers, different sizes of layers, etc.). In some implementations, the multiple options include using models of different types. For example, the models can include two or more different types such as a neural network, a support vector machine, a classifier, a regression model, a reinforcement learning model, a clustering model, a decision tree, a random forest model, a genetic algorithm, a Bayesian model, and a Gaussian mixture model. At least some of the multiple models can be models trained to make predictions of readiness with different levels of variance, for example, to reflect different bias/variance tradeoffs. At least some of the models can be trained to make predictions based on differing combinations of input features representing different sets of information about the subject.

The process 1400 includes selecting one of the multiple different machine learning techniques based on a user input (1406). Once the multiple analysis options are identified by the computer system 110, the computer system 110 may provide data for the different options to be indicated to a user, e.g., on a user interface. For example, based on the accessed data indicating the multiple different analysis techniques, the computer system 110 can provide, for display on a user interface, an indication of each of the multiple different analysis techniques. The computer system 110 may first filter the list of options to those applicable to the current data set, for example, the particular subject, readiness criteria, prediction type to be generated, set of collected data in the database, etc. corresponding to the current task or view corresponding to the user interface. The computer system 110 can receive data indicating user interaction with the user interface that selects one of the multiple different analysis techniques. For example, the user may interact with buttons, checkboxes, or other controls to indicate which of the analysis options the user selects to be used. The computer system 110 can then select and use the model(s) that the user input indicated should be used.

Other types of user input may be used by the computer system 110 to select the appropriate analysis technique. For example, without user input that directly selects an analysis technique or model, the computer system 110 may receive user input that indicates other user preferences. The computer system 110 may provide data causing a user interface to provide controls to indicate preferences such as desired speed of obtaining a prediction, a risk tolerance (e.g., an extent that predictions should bias against false positives, such as overestimates of readiness, or false negatives, such as underestimating readiness), whether any restrictions on the types of data used in the prediction should be taken into account, and so on. The computer system 110 can then select, from among the available analysis options, the option that best suits the user preferences. To aid in this selection, the computer system 110 can generate and store metrics that characterize each analysis option. For example, models can be evaluated and validated as part of training, and the accuracy, precision, computational cost, efficiency, and other parameters can be computed and stored as a profile for each model. The computer system 110 can then select the model(s) having a profile that most closely matches the characteristics indicated by user preferences.

For example, with respect to FIG. 1C, selecting one of the multiple different machine learning techniques based on a user input may include selecting one of the machine learning models 130, 132, and 134 based on the user input. For example, with respect to FIG. 2B, selecting one of the multiple different machine learning techniques based on a user input may include selecting a machine learning or model to generate a prediction for CRT, FRP, and/or ACS based on the user input. The user input may be made by a user of the system. The user input may be made by, for example, a coach, counselor, caregiver, care provider, specialist, employer, potential employer, supervisor, or other user associated with the subject. In some cases, the user input may be made by the subject.

The process 1400 includes generating a measure of predicted readiness of the subject with respect to the one or more readiness criteria (1408). This can involve generating feature scores and generating a prediction using a model for the selected analysis option, using techniques discussed above with respect to steps 1204, 1206, and/or 1208 of FIG. 12. The measure of predicted readiness can be determined based on any of the factors discussed above, such as current attributes of the subject, previous or former attributes of the subject, current or previous activities of the subject (e.g., activities assigned to the subject to increase a capability of the subject, or other activities), a planned or scheduled activities of the subject (e.g., a training plan indicating activities selected to increase a capability of the subject), and so on.

The measure of predicted readiness of the subject can be generated according to the selected machine learning technique. The measure of predicted readiness may be a measure of predicted readiness of the subject to satisfy one or more readiness criteria. The feature data may indicate attributes of the person such as, for example, physiological and psychological attributes. With respect to FIG. 1B, the feature data may be derived using the computer system 110, e.g., using the data aggregation module 112 to extract and/or organize the activity data. The feature data may include all or part of the aggregated data 122 shown in FIG. 1B. The feature data may be or include feature scores.

In some implementations, multiple measures of predicted readiness of the subject are generated prior to the selecting one of the multiple different machine learning techniques based on a user input. For example, each measure of predicted readiness generated may be generated using a different machine learning techniques. These generated measures may be sent to the subject and/or to a coach, counselor, caregiver, care provider, specialist, employer, potential employer, supervisor of the subject. These generated measures and/or visual representations of the generated measures may be presented on a user interface of a device belonging to the subject, and/or a user interface of a device belonging to a coach, counselor, caregiver, care provider, specialist, employer, potential employer, supervisor of the subject. Accordingly, the subject, and/or a coach, counselor, caregiver, care provider, specialist, employer, potential employer, supervisor of the subject may use these multiple measures and/or visual representations of the generated measures in selecting one of the multiple different machine learning techniques. As an example, the output 140 shown in FIG. 1B may be presented on a device belonging to the subject, and/or a device belonging to another person associated with the subject, e.g., a coach, counselor, caregiver, care provider, specialist, employer, potential employer, or supervisor.

The process 1400 includes providing output data based on the selected analysis technique (1410). The output data can update the user interface based on the measure of predicted readiness of the subject. In addition, or as an alternative, the output data can cause an interaction with one or more devices based on the measure of predicted readiness of the subject. For example, the output can include output as discussed above with respect to step 1210 of FIG. 12 or step 1310 of FIG. 13.

In some implementations, the computer system 110 provides, for display on a user interface, data indicating different predictions of readiness for a subject, where the different predictions were each generated using a different one of the multiple different analysis techniques. For example, as shown in FIG. 1C, predictions generated using different models (e.g., "Model A," "Model B," and "Model C") are generated and indicated. In the FIG. 1C example, measures of readiness are provided as scores, as well as a curve or trend line showing the expected progression of acquiring readiness over time. The computer system 110 also evaluates the suitability of the models and provides an indication of this analysis to assist the user, e.g., indications to "recommend" using Model B, or "do not recommend" for Model C.

To provide the output data, the computer system 110 may provide one or more of the following. For example, the computer system 110 may provide an indicator of the measure of predicted readiness for display on a user interface. The computer system 110 may provide visualization data, generated using the measure of predicted readiness, for illustrating a timeline or trend of predicted readiness of the subject over time. The computer system 110 may provide a recommendation, determined based on the measure of predicted readiness, of an action to improve or accelerate acquisition of readiness of the subject to satisfy the one or more readiness criteria. The computer system 110 may provide one or more interactive user interface controls to alter one or more planned actions for assisting the subject to achieve readiness to satisfy the one or more readiness criteria. The computer system 110 may provide one or more interactive user interface controls to select from among multiple options for assisting the subject to achieve readiness to satisfy the one or more readiness criteria. The computer system 110 may provide an indication of a predicted change in readiness of the subject, relative to a level of readiness indicated by the measure of predicted readiness, for each of one or more actions with respect to the subject.

In some implementations, the output data causes a device associated with the subject to initiate interactions that are selected based on the measure of predicted readiness of the subject. For example, with respect to FIG. 10, a program may be selected for the subject based on the measure of predicted readiness of the subject that includes a list of challenges (e.g., hip stability drill, military movement drill, run, etc.). The interactions may also include requesting feedback from the subject after a challenge is complete, after a certain amount of time has passed (e.g., one day, one week, one month, etc.), after a milestone has been reached (e.g., after subject has reached readiness, subject's performance trend indicates that the subject is expected to reach readiness, subject's performance trend indicates that the subject is expected to reach readiness by a certain point in time, etc.), after the subject has completed a particular percentage of the program (e.g., 25%, 50%, 75%, 100%), or the like. This feedback may include, for example, a level of pain, and/or a feeling (e.g., good, bad, neutral, etc.). The device may be, for example, the device 204 shown in FIG. 2A, or the device 304 shown in FIG. 3.

Figure 15:
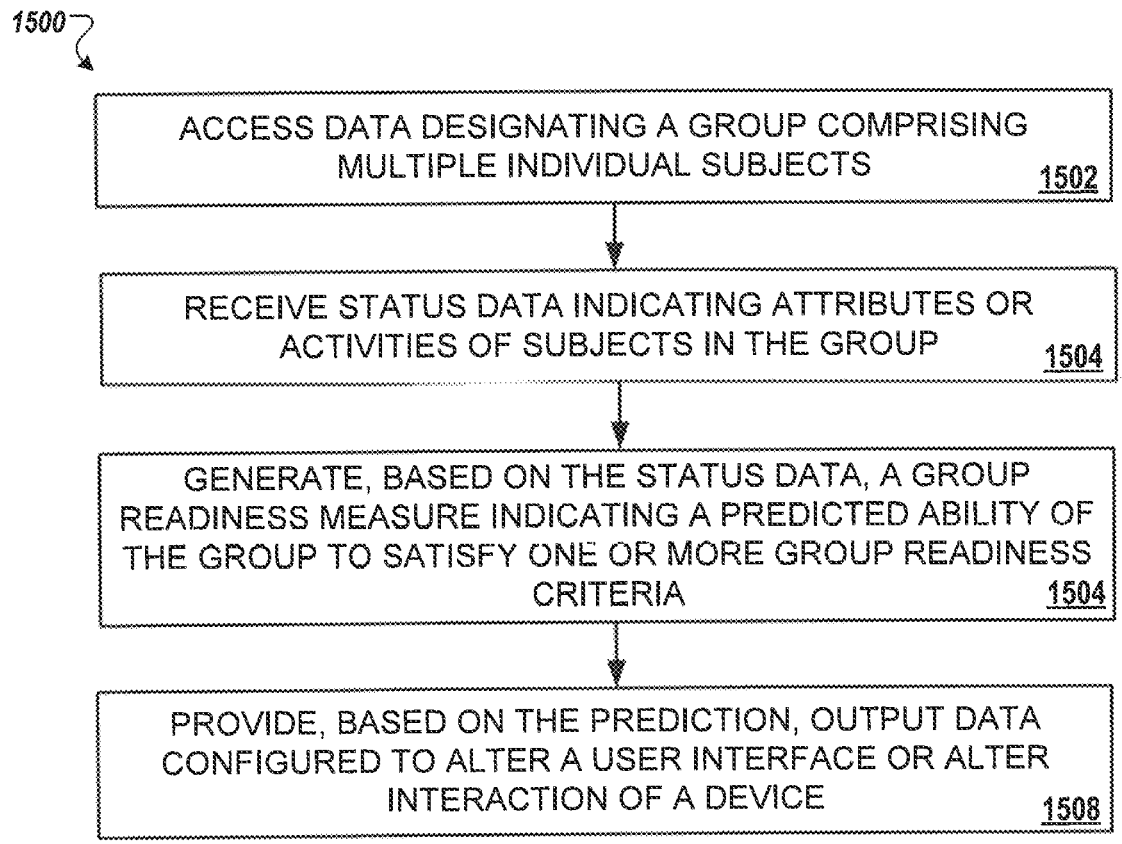
FIG. 15 is a flowchart that illustrates an example process for predicting readiness of a group or a team.

FIG. 15 is a flowchart that illustrates an example process for predicting readiness of a group or a team. The process 1500 can be performed by one or more computers, such as using the computer system 110 described above. Steps of the process 1500 can be performed by one or more servers, one or more client devices, or by a combination thereof and/or other devices.

The process 1500 includes receiving data designating a group comprising multiple individual subjects (1502). For example, the computer system 110 can access stored records that define different groups or teams, by indicating the assignment of different individual subjects to groups. As another example, the computer system 110 may receive an identifier for a group of interest, for example, through user input to a user interface that indicates a particular team of people for which a prediction is to be generated. The computer system 110 can access stored records defining group membership to determine the members of the indicated group.

As an example, a group could refer to a group of components of a device or a group of devices in a system, which each element has individual parameters and capabilities but the function of the entire group together is important. As another example, a group could be a sports team, a military unit, a department of an organization, or other group of people whose individual capabilities contribute to and affect the effectiveness of the group as a whole.

The process 1500 includes receiving status data indicating attributes and/or activities of subjects in the group (1504). This data may be obtained for individual subjects in the group (e.g., each subject in the group) and/or for the group as a whole. The data can include data obtained as discussed in step 1202 of FIG. 12, for any and all of the individual subjects and/or for the group itself. As discussed with respect to FIG. 1B, the data may include sensor data, data that is self-reported by the subjects, and so on.

The process 1500 includes generating a group readiness measure based on the status data (1504). The group readiness measure can indicate a predicted ability of the group to satisfy one or more group readiness criteria, e.g., at a current or future time. The group readiness criteria can be similar to the readiness criteria discussed above, but applies to the group as a whole to determine whether the group achieves a level of capability. For example, the group readiness criteria may specify that each of the individual members respectively meets some individual readiness criteria. As another example, the group readiness criteria may specify that the group should be capable of performing certain tasks, though not every member is required to have capability to perform all the tasks. The group readiness criteria may be a function of individual readiness scores (e.g., predictions).

The group readiness criteria may specify, for example, at least one of a physical state of the members of the group, a functional state of the members of the group, or a level of capability of the members of the group to perform a task.

As part of this process, information for each of the subjects in the group can be used and processed using one or more models. This may involve generating a prediction using the techniques of steps 1204, 1206, and/or 1208 of FIG. 12 for the group.

The group readiness measure may be generated using the one or more models, for example, at least one of a neural network, a support vector machine, a classifier, a regression model, a clustering model, a decision tree, a random forest model, a genetic algorithm, a Bayesian model, or a Gaussian mixture model. Machine learning models, statistical models, rule-based models, and other types of models can be used. The one or more models can be models trained based on training data indicating (i) activities or attributes of other subjects and (ii) outcomes for the other subjects with respect to corresponding readiness criteria. The training can use the respective progressions of readiness of the other subjects over time to configure the one or more models to predict readiness of subjects to satisfy one or more readiness criteria (e.g., individual readiness criteria). In a similar manner, the information about how groups have progressed over time can be used to train models to predict how a group will progress toward readiness to satisfy one or more group readiness criteria. As with the other models discussed herein, the models can be trained for specific readiness criteria, or may be trained more generally with the specific readiness criteria being input to or accessed by the model at the time predictions are made.

Generating the group readiness measure may include generating predictions for individual members of the group, with respect to individual readiness criteria, and then combining individual results (e.g., averaging, applying a weighted combination, or otherwise applying a function to the individual scores) to determine the group readiness measure. The group readiness measure may indicate a prediction, such as a predicted time that the group will achieve readiness to satisfy the one or more group readiness criteria or a prediction whether the group will achieve readiness to satisfy the one or more group readiness criteria.

In some implementations, a model may be generated or trained to predict group readiness measures based on information about the constituent members of the group. The model may be configured to receive input feature data about individual members and/or data indicating results of predictions of other models, such as readiness prediction values from models that assess individual capabilities of the members of the group. Thus, the group readiness measure may be, or may be based on, output from a model configured for this purpose.

In some implementations, generating the group readiness measure can include generating an individual readiness score for each of the multiple subjects in a group. The individual readiness scores indicate predictions of the respective capabilities of the subjects in the group. The group readiness measure can be generated based on the individual readiness scores for the subjects in the group. The individual readiness scores can respectively indicate predicted readiness of individual subjects to satisfy one or more individual readiness criteria. The individual readiness criteria can be different from the group readiness criteria.

To generate individual readiness scores, the computer system 110 can, for each of the multiple subjects: (1) provide, to one or more models, a set of feature scores for the subject derived from status data for the subject obtained from a database of attributes or activities of subjects; and (2) receive an output that is generated for the subject in response to the one or more models receiving the set of feature scores for the subject, where the individual readiness score for the subject is based on the output.

As an example, the group readiness measure can be an aggregate measure of the individual readiness scores for the subjects in the group, e.g., an average (e.g., mean, median, mode, etc.), a sum of the individual readiness scores, a maximum or minimum value of the individual readiness scores, a weighted combination, or other function of the individual readiness scores. As another example, to generate the group readiness measure, the computer system 110 can provide the individual readiness scores to one or more models trained to generate a group readiness measure based on examples of group readiness measures and corresponding individual readiness scores for members of the group. The computer system 110 can determine the group readiness measure based on the processing of the one or more models performed in response to receiving the individual readiness scores.

The readiness scores can indicate predictions of the respective capabilities of the members in the group. For example, the readiness scores can indicate a level of capability of each of the subjects to satisfy one or more readiness criteria. With respect to FIGS. 1A-1C, the readiness scores may be generated by the scoring and prediction module 114. The readiness scores can also indicate that one or more of the subjects are not yet capable of satisfying the one or more readiness criteria. The readiness criteria may be set by, for example, a coach, counselor, caregiver, care provider, specialist, employer, potential employer, supervisor of the subjects. The readiness criteria may make up or be part of the third-party input 152 shown in FIG. 1A. With respect to FIG. 6, the readiness criteria may be included in the program data store 638 and/or in the subject outline and content 626a. The readiness scores can be generated using one or more machine learning models such as, for example, the machine learning models 130, 132, and/or 134 shown in FIG. 1C.

The process 1500 includes providing output data based on the group readiness measure (1508). The output data can be configured to, for example, alter a user interface of a device or alter interaction of a device with one or more of the subjects in the group.

In some implementations, the computer system 110 uses the group measure to determine whether the group has achieve or is appropriately progressing toward readiness. The computer system 110 can use the process 1300 of FIG. 13 to select, as well as indicate and/or implement, actions to improve the capabilities of the group as a whole or individual members of the group. Thus, any of various interactions predicted to improve readiness of individuals or the group as a whole can be instructed to be performed by devices. For example, changes to data collection processes, alerts, reminders, forms, surveys, and so on can be identified and made in response to determining that the group readiness score does not provide a desired level of readiness or level of confidence that readiness will be achieved.

In some implementations, the computer system 110 determines a recommended change to the group to improve the readiness of the group. For example, the computer system 110 may determine to add or remove members from groups, to reassign members to different roles within groups, or to make other changes. The computer system 110 may identify changes to groups that would increase the total number of groups that meet the group readiness criteria and recommend or implement the changes. As an example, the computer system 110 may determine, based on readiness scores for two groups, that the first group has achieved readiness but the second group has not. The computer system 110 may further determine, based on individual readiness scores for members of the groups, that switching a high-performing member of the first group with a lower-performing member of the second group would allow both groups to reach readiness, and in response either recommend the change or implement the change.

The output data provided can indicate a prediction, such as (i) a predicted time that the group will achieve readiness or (ii) a prediction (e.g., classification or likelihood) whether the group will achieve readiness given one or more constraints. The group achieving readiness may include the group achieving readiness to satisfy the one or more group readiness criteria. The readiness criteria may be set by, for example, a coach, counselor, caregiver, care provider, specialist, employer, potential employer, supervisor of the subjects. The readiness criteria may make up or be part of the third-party input 152 shown in FIG. 1A. With respect to FIG. 6, the readiness criteria may be included in the program data store 638 and/or in the subject outline and content 626a. With respect to FIGS. 1A-1C, the predicted time that the group will achieve readiness, or the likelihood or prediction whether the group will achieve readiness given one or more constraints may be generated by the scoring and prediction module 114.

As examples, the output data can include one or more of: a score indicative of the prediction for display on a user interface; an indicator of the prediction for display on a user interface; visualization data, generated using the prediction, for illustrating a timeline or trend of predicted readiness of the group or one or more subjects in the group over time; a recommendation, determined based on the prediction, of an action to improve or accelerate acquisition of readiness of the group to satisfy the one or more group readiness criteria; a recommendation, determined based on the prediction, of an action to improve or accelerate acquisition of readiness of one or more subjects in the group to satisfy one or more individual readiness criteria; one or more interactive user interface controls to alter one or more planned actions for assisting the group to achieve readiness to satisfy the one or more group readiness criteria; one or more interactive user interface controls to select from among multiple options for assisting the group to achieve readiness to satisfy the one or more readiness criteria; or an indication of a predicted change in readiness of the group, relative to a level of readiness indicated by the prediction, for each of one or more actions with respect to the subject.

The processes of FIGS. 12-15 can be used to evaluate many different aspects of performance, including different aspect of human performance. This can include readiness of a person to face challenging situations and stress in a job role or other situation. To gauge these risks, the computer system 110 can predict readiness in holistic manner, across various different dimensions. For example, fitness for a task or role may involve components that are physical, emotional, cognitive, intellectual, spiritual, financial, and ethical. For example, a task may have physical requirements for a subject to perform, but may also have mental or emotional demands as well. Some tasks may require a person to be ethically or financially prepared. For example, a person in a role handling money may need to be financially prepared to that embezzling money is not a serious temptation, or a person working in a negotiation may need to be ethically and financially prepared to refuse bribes. The readiness criteria that are set for a task or role can include components or criteria for any and all of the different dimensions of readiness that are applicable to a desired state of readiness.

In some implementations, the computer system 110 can be used to predict and enhance readiness as part of a total force fitness (TFF) program. For example, the computer system 110 can be used to support individuals and groups of people in understanding their levels of readiness and their trends and progress, and can provide personalized recommendations about how to improve. The predictions and recommendations can be based on various areas, including psychological, behavioral, spiritual, social, physical, medical and dental, nutritional, and environmental domains. Predictions of readiness and recommendations for improvement can be made for individuals, military units of different types or sizes, classes or groups of people undergoing training, teams for particular tasks or purposes, and so on. The predictions can recommendations can be to achieve readiness to carry out of job tasks and/or to have the general physical and mental state needed for wellness that is not tied to specific job tasks. These predictions and recommendations can be made based on models developed from data sets describing the attributes and activities of soldiers and other personnel, using the techniques discussed herein.

The types of predictions that can be made by the computer system 110 include predictions of how long a state of readiness will be maintained by a subject. In other words, the computer system 110 can predict not only when and whether a subject will achieve readiness, but additionally or alternatively how long the state of readiness (e.g., attributes or abilities that satisfy the readiness criteria) will persist. This can be predicted as, for example, a predicted duration (e.g., an amount of time, such as a month, a year, etc. following the achievement of readiness), a specific date or time when readiness may be lost (e.g., readiness is expected until some predicted date or time in the future), or as a measure (e.g., a binary classification, confidence score, probability measure, etc.) whether readiness will be maintained at some future time. Similarly, the amount of variation in readiness over time (e.g., a variance or range that readiness is expected to fluctuate within) can be predicted.

In general, models can be trained to predict maintenance of readiness in the same manner that models are trained to predict acquisition of readiness, taking into account the same factors discussed above. Similarly, models can be trained to predict the effects of different candidate actions or interventions and their effects on maintaining readiness, so interventions can be selected to maintain readiness, just as models are trained and used to predict and select actions for reaching readiness in the first instance.

The predictions for maintaining readiness can be conditioned on predicted different activities involving the subject, which may or may not include proposed steps or plans designed to facilitate maintaining readiness. For example, the prediction may take into account a readiness maintenance plan for regular steps for physical training, practicing a skill, performing maintenance on equipment, periodic tests, and so on. Different candidate maintenance plans can be defined, and predictions can be made for each to indicate the different levels of readiness that may be maintained with different plans. Similarly, the expected tasks or workload of the subject can be taken into account. For example, a subject that is overloaded with a task may decline in readiness for being overworked. On the other hand, a subject that does not use or practice abilities required for readiness may decline in readiness for lack of practice or other factors. The computer system 110 can analyze data indicating the progression of readiness of subjects after their initial achievement of readiness according to readiness criteria, along with their activities and attributes over time, to determine how different everyday activities, work tasks, and interventions (e.g., such as training or maintenance actions) affect the maintenance of readiness. This can allow the computer system 110 to predict when additional actions, such as training or testing, would be needed or beneficial for different subjects. The computer system 110 may use machine learning models to learn, for example, the relationships between different subject attributes and activities and the eventual readiness maintenance profiles over time, and actions that best maintain readiness.

To make these predictions, one or more models can be trained to model the characteristics that affect readiness changes, once readiness has been achieved, for different subjects and different readiness criteria (e.g., different types of capabilities). The models can use examples of subjects whose readiness declines as well as subject whose readiness is maintained (e.g., kept the same or improved) over time. This training process can incorporate into the model(s) data indicative of the factors that led to maintenance of readiness by various subjects, the factors that led to decreasing readiness, and so on, along with the extent of the effects (e.g., magnitude, amount of variability, duration or latency of effects, etc.). Thus, the models can learn the typical progressions of readiness both in the process of achieving readiness in the first instance and for maintaining readiness thereafter. Indeed, some actions or training steps may be assessed for their impact on both readiness acquisition and readiness maintenance. For example, some training actions may promote achieving readiness quickly, but in a manner that readiness is not as stable or prolonged. This may be taken into account so the computer system 110 prioritizes other actions that may lead to slower but more lasting acquisition of readiness in recommendations. Similarly, some actions for maintaining or acquiring readiness for one set of criteria (e.g., for a first task or skill) may provide benefits for achieving readiness for another set of criteria (e.g., for a second task or skill). Thus, the computer system 110 can give priority to actions that maintain the readiness for one set of criteria and which also maintain and improve readiness for one or more other set of readiness criteria that are not applicable or required at the current time, such as criteria for an potential future job role, another task, or a new capability that the subject may need to meet in the future.

The data collected by the computer system 110 and used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected and used by the computer system 110 (e.g., to generate feature values, to train models, to identify and select actions to improve readiness, etc.) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteom ics, phylogenomics, phylotranscriptom ics, phytom ics, postgenom ics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., IsopropyI$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

In the claims, the term "or" is generally intended to be inclusive, not exclusive. For example, the phrase "A or B" should be interpreted as encompassing (1) A only, (2) B only, and (3) A and B together. Thus, absent any modifying word or phrase to specify exclusivity (e.g., "either A or B" or "only one of A or B"), listed items are not mutually exclusive.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a cathode ray tube or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method performed by one or more computers, the method comprising:

training, by the one or more computers, one or more models based on example data indicating patterns with which multiple subjects that have different attributes have acquired readiness to satisfy one or more readiness criteria, the one or more models being trained to predict a level of capability of a subject to satisfy the one or more readiness criteria based on input that indicates attributes of the subject, wherein the training uses the attributes of the subjects and the corresponding patterns of acquiring readiness indicated by the example data to customize readiness predictions according to attributes that are indicated by input to the one or more models;

accessing, by the one or more computers, a database to obtain status data that indicates attributes of a subject, the status data comprising data provided by an electronic device to the one or more computers over a communication network;

generating, by the one or more computers, a set of multiple readiness scores for the subject, each of the readiness scores in the set indicating a level of capability of the subject to satisfy the one or more readiness criteria at a different time, the set of multiple readiness scores being generated using the one or more models and indicating a trend of acquiring readiness for the subject;

accessing, by the one or more computers, data indicating multiple candidate actions for improving capability of the subject to satisfy one or more readiness criteria;

selecting, by the one or more computers, a subset of the candidate actions for the subject based on a comparison of (i) a trend of acquiring readiness by the subject that is indicated by the set of multiple readiness scores generated using the one or more models and (ii) trends observed for other subjects in acquiring readiness to satisfy the one or more readiness criteria; and providing, by the one or more computers, output configured to perform at least one of (i) causing one or more of the actions in the selected subset to be performed by the one or more computers or another system or (ii) causing an indication of one or more of the actions in the selected subset to be presented on a user interface of the one or more computers or another system.

2. The method of claim 1, wherein the one or more models comprise one or more machine learning models.

3. The method of claim 1, wherein the one or more readiness criteria comprise at least one of:
a physical state of the subject;
a functional state of the subject; or
a level of capability of the subject to perform a task.

4. The method of claim 1, wherein the one or more models comprise at least one of a neural network, a support vector machine, a classifier, a regression model, a clustering model, a decision tree, a random forest model, a genetic algorithm, a Bayesian model, or a Gaussian mixture model.

5. The method of claim 1, wherein the one or more models have been trained based on training data indicating (i) activities or attributes of other subjects and (ii) outcomes for the other subjects with respect to the readiness criteria,
wherein the training uses the respective progressions of readiness of the other subjects over time to configure the one or more models to predict readiness of subjects to satisfy one or more readiness criteria.

6. The method of claim 1, wherein the database comprises data generated for the subject over a period of time, the status data comprising information about activities or attributes of the subject at multiple points in time; and
wherein the one or more readiness scores are generated using the one or more models by providing, to the one or more models, a set of feature scores, derived from the status data, that comprises measures of the activities or attributes of the subject at each of the multiple points in time.

7. The method of claim 6, wherein the set of feature scores is based on sensor data that is acquired by one or more sensors during one or more activities of the subject or that indicates one or more attributes of the subject.

8. The method of claim 1, comprising:
determining (i) a plurality of training options for the subject and (ii) measures of how the respective training options are predicted to affect the readiness of the subject to satisfy the one or more readiness criteria;
wherein the selection is based at least in part on the measures.

9. The method of claim 1, wherein accessing the data indicating the multiple candidate actions comprises accessing data indicating candidate actions comprising at least one of:
changing a frequency, number, or intensity of planned training activities for the subject;
changing an allocation of resources for the subject;
changing a type of training for the subject;
changing an assignment of an individual to assist the subject in achieving readiness; or
providing, for output by a client device, a notification indicating the level of capability of the subject to satisfy one or more readiness criteria that is indicated by the one or more readiness scores.

10. The method of claim 1, wherein accessing the data indicating the multiple candidate actions comprises:
generating one or more candidate actions based on information indicating available resources for training the subject and at least one of:
information about the subject from the database;
data indicating actions taken to improve readiness of the subject; or
data indicating one or more planned future actions to improve readiness of the subject.

11. The method of claim 1, wherein selecting the subset of the candidate actions comprises:
determining a score for each of the candidate actions, the scores being indicative of a predicted effect of the respective candidate actions on readiness of the subject to satisfy the one or more readiness criteria; and
selecting the subset based on the scores for the candidate actions.

12. The method of claim 11, wherein the scores for the candidate actions are determined based on data indicating changes in attributes or capabilities of one or more other subjects after actions corresponding to the candidate actions are performed for the one or more other subjects.

13. The method of claim 11, wherein the scores for the candidate actions are determined based on data indicating previous activities of the subject and changes in attributes or capabilities of the subject after the previous activities.

14. The method of claim 1, wherein the scores for the candidate actions are determined based on (i) current attributes of the subject and (ii) planned or scheduled activities of the subject.

15. The method of claim 1, wherein the readiness scores indicate predicted measures of current capability of the subject to perform a particular activity.

16. The method of claim 1, wherein the readiness scores indicate predicted measures of future capability of the subject to perform a particular activity.

17. The method of claim 1, comprising determining, based on the comparison, that a progression of acquiring readiness by the subject deviates from a reference progression of acquiring readiness that is based on data indicating a progression of readiness measures over time for multiple subjects that successfully acquired readiness;
wherein selecting the subset of the candidate actions for the subject comprises selecting a subset of the candidate actions that is predicted to improve the subject's progression of acquiring readiness toward the reference progression of acquiring readiness.

18. The method of claim 1, comprising causing a device to display one or more scores indicative of a predicted change to the readiness of the subject to satisfy the one or more readiness criteria.

19. The method of claim 1, comprising generating visualization data to illustrate a timeline or trend indicating a progression of readiness of the subject to satisfy the one or more readiness criteria if one or more of the actions in the selected subset are performed; and
providing the visualization data to cause a device to display a visualization based on the visualization data.

20. The method of claim 1, comprising determining a composite reference trend representing a typical progression toward readiness, the composite reference trend being based on progressions toward readiness by multiple subjects that have successfully acquired readiness to achieve the one or more readiness criteria; and
determining that the trend indicated by the set of readiness scores for the subject deviates from the composite reference trend;
wherein selecting the subset of the candidate actions for the subject comprises, in response to determining that the trend indicated by the set of readiness scores for the subject deviates from the composite reference trend, selecting candidate actions to adjust the progression of readiness by the subject to align with the composite reference trend for subjects that have successfully acquired readiness to satisfy the one or more readiness criteria.

21. The method of claim 1, wherein the training uses the example data to learn relationships between different attributes of subjects and different outcomes in acquiring readiness to satisfy the one or more readiness criteria, the training updating the one or more models based on the learned relationships.

22. The method of claim 1, wherein the training updates the one or more models to generate predictions in which the presence of different attributes results in different levels of effect that training activities are predicted to have on acquiring readiness to satisfy the one or more readiness criteria.

23. The method of claim 1, wherein selecting the subset of candidate actions comprises:
evaluating a magnitude of predicted improvement to the readiness of the subject for the different candidate actions; and
filtering the multiple candidate actions such that the subset includes candidate actions predicted to provide the subject at least a minimum level of predicted improvement in acquiring readiness to satisfy the one or more readiness criteria.

24. The method of claim 1, wherein the subset of the candidate actions is selected based on the attributes of the subject.

25. A system comprising:
one or more computers; and
one or more computer-readable media storing instructions that, when executed, cause the one or more computers to perform operations comprising:
training, by the one or more computers, one or more models based on example data indicating patterns with which multiple subjects that have different attributes have acquired readiness to satisfy one or more readiness criteria, the one or more models being trained to predict a level of capability of a subject to satisfy the one or more readiness criteria based on input that indicates attributes of the subject, wherein the training uses the attributes of the subjects and the corresponding patterns of acquiring readiness indicated by the example data to customize readiness predictions according to attributes that are indicated by input to the one or more models;
accessing, by the one or more computers, a database to obtain status data that indicates attributes of a subject, the status data comprising data provided by an electronic device to the one or more computers over a communication network;
generating, by the one or more computers, a set of multiple readiness scores for the subject, each of the readiness scores in the set indicating a level of capability of the subject to satisfy the one or more readiness criteria at a different time, the set of multiple readiness scores being generated using the one or more models and indicating a trend of acquiring readiness for the subject;
accessing, by the one or more computers, data indicating multiple candidate actions for improving capability of the subject to satisfy one or more readiness criteria;
selecting, by the one or more computers, a subset of the candidate actions for the subject based on a comparison of (i) a trend of acquiring readiness by the subject that is indicated by the set of multiple readiness scores generated using the one or more models and (ii) trends observed for other subjects in acquiring readiness to satisfy the one or more readiness criteria; and
providing, by the one or more computers, output configured to perform at least one of (i) causing one or more of the actions in the selected subset to be performed by the one or more computers or another system or (ii) causing an indication of one or more of the actions in the selected subset to be presented on a user interface of the one or more computers or another system.

26. One or more non-transitory computer-readable media storing instructions that, when executed by one or more computers, cause the one or more computers to perform operations comprising:
training, by the one or more computers, one or more models based on example data indicating patterns with which multiple subjects that have different attributes have acquired readiness to satisfy one or more readiness criteria, the one or more models being trained to predict a level of capability of a subject to satisfy the one or more readiness criteria based on input that indicates attributes of the subject, wherein the training uses the attributes of the subjects and the corresponding patterns of acquiring readiness indicated by the example data to customize readiness predictions according to attributes that are indicated by input to the one or more models;
accessing, by the one or more computers, a database to obtain status data that indicates attributes of a subject, the status data comprising data provided by an electronic device to the one or more computers over a communication network;
generating, by the one or more computers, a set of multiple readiness scores for the subject, each of the readiness scores in the set indicating a level of capability of the subject to satisfy the one or more readiness criteria at a different time, the set of multiple readiness scores being generated using the one or more models and indicating a trend of acquiring readiness for the subject;
accessing, by the one or more computers, data indicating multiple candidate actions for improving capability of the subject to satisfy one or more readiness criteria;
selecting, by the one or more computers, a subset of the candidate actions for the subject based on a comparison of (i) a trend of acquiring readiness by the subject that is indicated by the set of multiple readiness scores generated using the one or more models and (ii) trends observed for other subjects in acquiring readiness to satisfy the one or more readiness criteria; and
providing, by the one or more computers, output configured to perform at least one of (i) causing one or more of the actions in the selected subset to be performed by the one or more computers or another system or (ii) causing an indication of one or more of the actions in the selected subset to be presented on a user interface of the one or more computers or another system.

* * * * *

UNITED STATES PATENT AND TRADEMARK OFFICE
CERTIFICATE OF CORRECTION

PATENT NO. : 11,151,462 B2  
APPLICATION NO. : 16/781793  
DATED : October 19, 2021  
INVENTOR(S) : Praduman Jain et al.

Page 1 of 1

It is certified that error appears in the above-identified patent and that said Letters Patent is hereby corrected as shown below:

On the Title Page

Item (54) and in the Specification, Column 1, Lines 1-3, Delete "SYSTEMS AND METHODS FOR USING MACHINE LEARNING TO IMPROVE PROCESSES FOR ACHIEVING READINESS" and insert -- AUTOMATED PERSONALIZED INTERVENTIONS FOR CLINICAL RESEARCH AND HEALTHCARE --, therefor.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*